US008084041B2

(12) United States Patent
Jacobs, Jr. et al.

(10) Patent No.: US 8,084,041 B2
(45) Date of Patent: Dec. 27, 2011

(54) USE OF MYCOBACTERIAL VACCINES IN CD4+ OR CD8+ LYMPHOCYTE-DEFICIENT MAMMALS

(75) Inventors: William R. Jacobs, Jr., Pelham, NY (US); Tsungda Hsu, Bronx, NY (US); Vasan Sambandamurthy, Singapore (SG); Sheldon Morris, Beltsville, MD (US); Stoyan Bardarov, Worcester, MA (US); Svetoslav Bardarov, legal representative, Worcester, MA (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 85 days.

(21) Appl. No.: 10/542,958

(22) PCT Filed: Jan. 23, 2004

(86) PCT No.: PCT/US2004/001773
§ 371 (c)(1),
(2), (4) Date: Jan. 30, 2007

(87) PCT Pub. No.: WO2004/066928
PCT Pub. Date: Aug. 12, 2004

(65) Prior Publication Data
US 2007/0202131 A1    Aug. 30, 2007

Related U.S. Application Data

(60) Provisional application No. 60/442,631, filed on Jan. 24, 2003.

(51) Int. Cl.
*A61K 39/04* (2006.01)
*A61K 39/02* (2006.01)
*C07H 21/04* (2006.01)

(52) U.S. Cl. ...... 424/248.1; 424/9.1; 424/9.2; 424/93.2; 424/184.1; 424/185.1; 424/190.1; 424/234.1; 435/243; 435/253.1; 435/440; 536/23.1; 536/23.7

(58) Field of Classification Search ............... 424/9.1, 424/9.2, 93.2, 184.1, 185.1, 190.1, 234.1, 424/248.1; 435/243, 253.1, 440; 536/23.1, 536/23.7
See application file for complete search history.

(56) References Cited

U.S. PATENT DOCUMENTS

| | | | |
|---|---|---|---|
| 5,750,384 A | 5/1998 | Jacobs, Jr. et al. |
| 5,837,732 A | 11/1998 | Sacchettini et al. |
| 5,955,077 A | 9/1999 | Andersen et al. |
| 5,968,733 A | 10/1999 | Bloom et al. |
| 5,972,700 A | 10/1999 | Jacobs, Jr. |
| 6,015,890 A | 1/2000 | Jacobs, Jr. et al. |
| 6,221,364 B1 | 4/2001 | Paveka et al. |
| 6,221,365 B1 | 4/2001 | Jones |
| 6,268,201 B1 | 7/2001 | Alland et al. |
| 6,271,034 B1 | 8/2001 | Bardarov et al. |
| 6,290,966 B1 | 9/2001 | Cox et al. |
| 6,387,694 B1 | 5/2002 | McKinney et al. |
| 6,423,545 B1 | 7/2002 | Pavelka, Jr. et al. |
| 6,562,348 B2 | 5/2003 | Hondalus et al. |
| 6,566,121 B1 | 5/2003 | Jacobs, Jr. et al. |
| 6,733,761 B2 | 5/2004 | McKinney et al. |
| 6,752,994 B2 | 6/2004 | Jacobs, Jr. et al. |
| 6,821,769 B2 | 11/2004 | Alland et al. |
| 2003/0059441 A1 | 3/2003 | Pavelka et al. |
| 2004/0001866 A1 | 1/2004 | Jacobs et al. |
| 2005/0260232 A1 | 11/2005 | Sambandamurthy et al. |

FOREIGN PATENT DOCUMENTS

| | | |
|---|---|---|
| WO | WO 03/070164 A2 | 8/2003 |
| WO | WO 2006/076343 A1 | 7/2006 |
| WO | WO 2006/076517 A1 | 7/2006 |
| WO | WO 2006/076519 A2 | 7/2006 |

OTHER PUBLICATIONS

Waters.W.R. Failure of a *Mycobacterium tuberculosis* deltaRD1 deltapanCD double deletion mutant in a neonatal calf aerosol *M. bovis* challenge model: Comparisons to responses elicited by *M. bovis* bacille Calmette Guerin. Vaccine, vol. 25, pp. 7832-7840, 2007.*

Sambandamurthy, V.K., et al., Vaccine, vol. 24, pp. 6309-6320, 2006.*

Andersen, P., "Host Responses and Antigens Involved in Protective Immunity to *Mycobacterium tuberculosis*"; Scand. J. Immunol. 1997, pp. 115-131, vol. 45.

Andersen, P., et al., "Proteins Released from *Mycobacterium tuberculosis* during Growth"; Infection and Immunity, Jun. 1991, pp. 1905-1910, vol. 59, No. 6.

Behr, M.A., et al., "Comparative Genomics of BCG Vaccines by Whole-Genome DNA Microarray"; Science, May 28, 1999, pp. 1520-1523, vol. 284.

Camacho, L.R., et al., "Identification of a virulence gene cluster of *Mycobacterium tuberculosis* by signature-tagged transposon mutagenesis"; Molecular Microbiology, 1999, pp. 257-267, vol. 34.

Chambers, M.A., et al., "Identification of a *Mycobacterium bovis* BCG Auxotrophic Mutant That Protects Guinea Pigs against *M. bovis* and Hematogenous Spread of *Mycobacterium tuberculosis* without Sensitization to Tuberculin"; Infection and Immunity, Dec. 2000, pp. 7094-7099, vol. 68, No. 12.

Cole, S.T., et al., "Deciphering the biology of *Mycobacterium tuberculosis* from the complete genome sequence"; Nature, Jun. 11, 1998, pp. 537-544 + table pages, vol. 393.

Cox, J., et al., "Complex lipid determines tissue-specific replication of *Mycobacterium tuberculosis* in mice"; Nature, Nov. 4, 1999, pp. 79-83, vol. 402.

Dascher C.C. et al., "Immunization with a mycobacterial lipid vaccine improves pulmonary pathology in the guinea pig model of tuberculosis"; International Immunology, Aug. 2003, pp. 915-925, vol. 15, No. 8.

(Continued)

Primary Examiner — Rodney P. Swartz
(74) Attorney, Agent, or Firm — Amster, Rothstein & Ebenstein LLP

(57) ABSTRACT

Methods of treating a mammal that is deficient in CD4+ and/or CD8+ lymphocytes are provided. The methods comprise inoculating the mammal with an attenuated mycobacterium in the *M. tuberculosis* complex. In these methods, the mycobacterium comprises two deletions, wherein a virulent mycobacterium in the *M. tuberculosis* complex having either deletion exhibits attenuated virulence. Use of these mycobacteria for the manufacture of a medicament for the treatment of mammals deficient in CD4+ and/or CD8+ lymphocytes is also provided.

9 Claims, 27 Drawing Sheets

OTHER PUBLICATIONS

De Voss, J.J., et al. "The salicylate-derived mycobactin siderophores of *Mycobacterium tuberculosis* are essential for growth in macrophages"; PNAS, Feb. 1, 2000, pp. 1252-1257, vol. 97, No. 3.

Glickman, M.S., et al., "The *Mycobacterium tuberculosis* cmaA2 Gene Encodes a Mycolic Acid trans-Cyclopropane Synthetase"; The Journal of Biological Chemistry, Jan. 19, 2001, pp. 2228-2233, vol. 276, No. 3.

Gordon, S.V., et al., "Genomics of *Mycobacterium bovis*"; Tuberculosis, 2001, pp. 157-163, vol. 81(1/2).

Guleria, I., et al., "Auxotrophic vaccines for tuberculosis"; Nature Medicine, Mar. 1996, pp. 334-337, vol. 2, No. 3.

Harboe M. et al., "Evidence for Occurance of the ESAT-6 Protein in *Mycobacterium tuberculosis* and Virulent *Mycobacterium bovis* and for Its Absence in *Mycobacterium bovis* BCG"; Infection and Immunity, Jan. 1996, pp. 16-22, vol. 64, No. 1.

Hernandez-Pando R. et al., "Pathogenesis of Tuberculosis in Mice Exposed to Low and High Doses of an Environmental Mycobacterial Saprophtye before Infection"; Infection and Immunity, Aug. 1997, pp. 3317-3327, vol. 65, No. 8.

Hondalus, M.K., et al., "Attenuation of and Protection Induced by a Leucine Auxotroph of *Mycobacterium tuberculosis*"; Infection and Immunity, May 2000, pp. 2888-2898, vol. 68, No. 5.

Hsu, T., et al., "The primary mechanism of attenuation of bacillus Calmette-Guérin is a loss of secreted lytic function required for invasion of lung interstitial tissue"; PNAS, Oct. 2003, pp. 1240-1225, vol. 100, No. 21.

Jackson, M., et al., "Persistence and Protective Efficacy of a *Mycobacterium tuberculosis* Auxotroph Vaccine"; Infection and Immunity, Jun. 1999, pp. 2867-2873, vol. 67, No. 6.

Ladel, C.H., et al., "Immune response to *Mycobacterium bovis* bacille Calmette Guérin infection in major histocompatibility complex class I- and II-deficient knock-out mice: contribution of CD4 and CD8 T cells to acquired resistance"; Eur. J. Immunol., 1995, pp. 377-384, vol. 25.

Mahairas, G.G., et al., "Molecular Analysis of Genetic Differences between *Mycobacterium bovis* BCG an Virulent *M. bovis*"; Journal of Bacteriology, Mar. 1996, pp. 1274-1282, vol. 178, No. 5.

Manca, C., et al., "Virulence of a *Mycobacterium tuberculosis* clinical isolate in mice is determined by failure to induce Th1 type immunity and is associated with induction of IFN-alpha/beta"; PNAS, May 8, 2001, pp. 5752-5757, vol. 98, No. 10.

McKinney, J.D., et al., "Persistence of *Mycobacterium tuberculosis* in macrophages and mice requires the glyoxylate shunt enzyme isocitrate lyase"; Nature, Aug. 17, 2000, pp. 735-738, vol. 406.

Mogues, T., et al., "The Relative Importance of T Cell Subsets in Immunity and Immunopathology of Airborn *Mycobacterium tuberculosis* Infection in Mice"; J. Exp. Med., Feb. 2001, pp. 271-280, vol. 193, No. 3.

Moreira A.L. et al., "Mycobacterial Antigens Exacerbate Disease Manifestations in *Mycobacterium tuberculosis*-Infected Mice"; Infection and Immunity, Apr. 2002, pp. 2100-2107, vol. 70, No. 4.

Pavelka, Jr., M.S. and Jacobs, Jr., W.R., "Comparison of the Construction of Unmarked Deletion Mutations in *Mycobacterium smegmatis*, *Mycobacterium bovis*, Bacillus Calmette-Guerin, and *Mycobacterium tuberculosis* H37Rv by Allelic Exchange", Journal of Bacteriology, Aug. 1999, pp. 4780-4789, vol. 181, No. 16.

Sambandamurthy V.K. et al., "A pantothenate auxotroph of *Mycobacterium tuberculosis* is highly attenuated and protects mice against tuberculosis"; Nature Medicine, Oct. 2002, pp. 1171-1174, vol. 8, No. 10.

Sambandamurthy V.K. et al., "Long-Term Protection against Tuberculosis following Vaccination with a Severely Attenuated Double Lysine and Pantothenate Auxotroph of *Mycobacterium tuberculosis*"; Infection and Immunity, Feb. 2005, pp. 1196-1203, vol. 73, No. 2.

Sampson S.L. et al., "Protection Elicited by a Double Leucine and Pantothenate Auxotroph of *Mycobacterium tuberculosis* in Guinea Pigs"; Infection and Immunity, May 2004, pp. 3031-3037, vol. 72, No. 5.

Skinner M.A. et al., "A DNA prime-live vaccine boost strategy in mice can augment IFN-gamma responses to mycobacterial antigens but does not increase the protective efficacy of two attenuated strains of *Mycobacterium bovis* against bovine tuberculosis"; Immunology, Apr. 2003, pp. 548-555, vol. 108, No. 4.

Slyshenkov, V.S., et al., "Pantothenic Acid and Its Derivatives Protect Ehrlich Ascites Tumor Cells Against Lipid Peroxidation"; Free Radical Biology & Medicine, 1995, pp. 767-772, vol. 19, No. 6.

Smith, D.A., et al. "Characterization of Auxotrophic Mutants of *Mycobacterium tuberculosis* and Their Potential as Vaccine Candidates"; Infection and Immunity, Feb. 2001, pp. 1142-1150, vol. 69, No. 2.

Taylor, J.L., et al., "Pulmonary Necrosis Resulting from DNA Vaccination against Tuberculosis"; Infection and Immunity, Apr. 2003, pp. 2192-2198, vol. 71, No. 4.

Weber, I., et al., "Anaerobic nitrate reductase (narGHJI) activity of *Mycobacterium bovis* BCG in vitro and its contribution to virulence in immunodeficient mice"; Molecular Microbiology, 2000, pp. 1017-1025, vol. 35, No. 5.

International Search Report (3 pages) for related application PCT/US2004/001773 with an international filing date of Jan. 23, 2004.

Written Opinion (5 pages) for related application PCT/US2004/001773 with an international filing date of Jan. 23, 2004.

Amendment in Response to Dec. 8, 2008 Office Action for U.S. Appl. No. 10/351,452, filed Feb. 3, 2009.

Co-pending U.S. Appl. No. 10/351,452, filed Jan. 24, 2003.

Co-pending U.S. Appl. No. 11/109,056, filed Apr. 19, 2005.

\* cited by examiner

US 8,084,041 B2

USE OF MYCOBACTERIAL VACCINES IN CD4+ OR CD8+ LYMPHOCYTE-DEFICIENT MAMMALS

CROSS-REFERENCE TO RELATED APPLICATIONS

This application is a National Stage of International Application No. PCT/US2004/001773, filed Jan. 23, 2004, which claims the benefit of U.S. Provisional Application No. 60/442,631, filed Jan. 24, 2003.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided by the terms of AI26170 awarded by National Institutes of Health.

BACKGROUND OF THE INVENTION (1) Field of the Invention

The present invention generally relates to live bacterial vaccines. More specifically, the invention is related to novel *Mycobacterium* sp. compositions, and the use of those compositions to protect mammals against disease caused by virulent *Mycobacterium* sp.

(2) Description of the Related Art

REFERENCES CITED

Abiko, Y. in *Metabolic Pathways*. D. M. Greenburg, Ed. (Academic Press, New York, 1975).

Afshar, K., Gonczy, P., DiNardo, S. & Wasserman, S. A. fumble encodes a pantothenate kinase homolog required for proper mitosis and meiosis in *Drosophila melanogaster*. Genetics 157, 1267-76. (2001).

Altare, F., Lammas, D., Revy, P., Jouanguy, E., Doffinger, R., Lamhamedi, S., Drysdale, P., Scheel-Toellner, D., Girdlestone, J., Darbyshire, P., Wadhwa, M., Dockrell, H., Salmon, M., Fischer, A., Durandy, A., Casanova, J. L. & Kumararatne, D. S. (1998) J Clin Invest 102, 2035-40.

Andersen, P. Host responses and antigens involved in protective immunity to *Mycobacterium tuberculosis*. Scand. J. Immunol. 45, 115-31 (1997).

Andersen, P., Askgaard, D., Ljungqvist, L., Bennedsen, J. & I. Heron. Proteins released from *Mycobacterium tuberculosis* during growth. Infect. Immun. 59, 1905-10. (1991).

Balasubramanian, V., et al. Allelic exchange in *Mycobacterium tuberculosis* with long linear recombination substrates. J. Bacteriol. 178, 273-9 (1996).

Baldwin, S. L. et al. Evaluation of new vaccines in the mouse and guinea pig model of *tuberculosis*. Infect. Immun. 66, 2951-2959 (1998).

Bardarov, S. et al. Conditionally replicating mycobacteriophages: a system for transposon delivery to *Mycobacterium tuberculosis*. Proc. Natl. Acad. Sci. USA 94, 10961-6. (1997).

Bardarov, S. et al. Microbiology 148, 3007-17 (2002).

Behar, S. M., et al. Susceptibility of mice deficient in CD1D or TAP1 to infection with *Mycobacterium tuberculosis*. J. Exp. Med. 189, 1973-80 (1999).

Behr, M. A. et al. Comparative genomics of BCG vaccines by whole-genome DNA microarray [see comments]. Science 284, 1520-3 (1999).

Behr, M. A. & Small, P. M. (1997) Nature 389, 1334.

Behr, M. A., Wilson, M. A., Gill, W. P., Salamon, H., Schoolnik, G. K., Rane, S. & Small, P. M. (1999) Science 284, 1520-3.21. Gordon, S. V., Brosch, R., Billault, A., Garnier, T., Eiglmeier, K. & Cole, S. T. (1999) Mol Microbiol 32, 643-55.

Bermudez, L. E., Sangari, F. J., Kolonoski, P., Petrofsky, M. and J. Goodman. Infect. Immun. 71, 140-146 (2002)

Berthet, F. X., Rasmussen, P. B., Rosenkrands, I., Andersen, P. & B. A. Gicquel. *Mycobacterium tuberculosis* operon encoding ESAT-6 and a novel low-molecular-mass culture filtrate protein (CFP-10). Microbiology 144, 3195-203. (1998).

Bloom, B. R. (1989) Nature 342, 115-20.

Bloom, B. R. & P. Fine, in Tuberculosis pathogenesis, protection, and control (ed. Bloom, B. R.) (American Society for Microbiology, Washington, D.C., 1994).

Calmette, A. & C. Guerin. Origine intestinale de la tuberculose pulmonaire. Ann. Inst. Pasteur 19, 601-618 (1905).

Brandt, L., Feino Cunha, J., Weinreich Olsen, A., Chilima, B., Hirsch, P., Appelberg, R. & Andersen, P. (2002) Infect Immun 70, 672-8.

Braun, M. M. & Cauthen, G. (1992) Pediatr Infect Dis J 11, 220-7.

Buller, R. M., Holmes, K. L., Hugin, A., Frederickson, T. N. & Morse, H. C., 3rd (1987) Nature 328, 77-9.

Calmette, A. & C. Guerin. C. R. Acad. Sci. 149, 716 (1909).

Calmette, A. & C. Guerin. Ann. Inst. Pasteur 34, 553 (1920).

Calmette, A. & H. Plotz. Protective inoculation against *tuberculosis* with BCG. Am. Rev. Tuberc. 19, 567-572 (1929).

Camacho, L. R., Ensergueix, D., Perez, E., Gicquel, B. & Guilhot, C. Identification of a virulence gene cluster of *Mycobacterium tuberculosis* by signature-tagged transposon mutagenesis. Mol Microbiol 34, 257-67. (1999).

Canaday, D. H. et al. Activation of human CD8+ alpha beta TCR+ cells by *Mycobacterium tuberculosis* via an alternate class I MHC antigen-processing pathway. J. Immunol. 162, 372-9 (1999).

Cardin, R. D., Brooks, J. W., Sarawar, S. R. & Doherty, P. C. (1996) J Exp Med 184, 863-71.

Carriere, C. et al. Conditionally replicating luciferase reporter phages: improved sensitivity for rapid detection and assessment of drug susceptibility of *Mycobacterium tuberculosis*. J. Clin. Microbiol. 35, 3232-9. (1997).

Caruso, A. M., Serbina, N., Klein, E., Triebold, K., Bloom, B. R. & Flynn, J. L. (1999) J Immunol 162, 5407-16.

Casanova, J. L., Jouanguy, E., Lamhamedi, S., Blanche, S. & Fischer, A. (1995) Lancet 346, 581.

Chambers, M. A. et al. Identification of a *Mycobacterium bovis* BCG auxotrophic mutant that protects guinea pigs against *M. bovis* and hematogenous spread of *Mycobacterium tuberculosis* without sensitization to tuberculin. Infect. Immun. 68, 7094-9 (2000).

Cho, S. et al. Antimicrobial activity of MHC class I-restricted CD8+ T cells in human *tuberculosis*. Proc. Natl. Acad. Sci. USA 97, 12210-5 (2000).

Cirillo, J. D. et al. A novel transposon trap for mycobacteria: isolation and characterization of IS1096. J. Bacteriol. 173, 7772-80 (1991).

Colditz G. A. et al. Pediatrics 96, 29-35. (1995).

Cole, S. T. et al. Deciphering the biology of *Mycobacterium tuberculosis* from the complete genome sequence [see comments] [published erratum appears in Nature 1998 Nov. 12; 396(6707):190]. Nature 393, 537-44 (1998).

Collins, F. M. Protection to mice afforded by BCG vaccines against an aerogenic challenge by three mycobacteria of decreasing virulence. Tubercle 66, 267-76. (1985).

Collins, F. M. Antituberculous immunity: new solutions to an old problem. Rev Infect Dis. 13, 940-50 (1991).

Cooper, A. M., Dalton, D. K., Stewart, T. A., Griffin, J. P., Russell, D. G. & Orme, I. M. (1993) J Exp Med 178, 2243-7.

Corbett, E. L., Watt, C. J., Walker, N., Maher, D., Williams, B. G., Raviglione, M. C. & Dye, C. (2003) Arch Intern Med 163, 1009-21.

Cowley, S. C. & Elkins, K. L. (2003) J Exp Med 198, 379-389.

Cox, J. S., Chen, B., McNeil, M. & W. R. Jacobs, Jr. Complex lipid determines tissue-specific replication of *Mycobacterium tuberculosis* in mice. Nature 402, 79-83 (1999).

de Jong, R., Altare, P., Haagen, I. A., Elferink, D. G., Boer, T., van Breda Vriesman, P. J., Kabel, P. J., Draaisma, J. M., van Dissel, J. T., Kroon, F. P., Casanova, J. L. & Ottenhoff, T. H. (1998) Science 280, 1435-8.

de la Calle-Marin, O. et al. (2001) J. Clin. Invest. 108, 117-123

D'Souza, C. D. et al. An anti-inflammatory role for gamma delta T lymphocytes in acquired immunity to *Mycobacterium tuberculosis*. J. Immunol. 158, 1217-21 (1997).

D'Souza, C. D. et al. A novel nonclassic beta2-microglobulin-restricted mechanism influencing early lymphocyte accumulation and subsequent resistance to *tuberculosis* in the lung. Am. J. Respir. Cell. Mol. Biol. 23, 188-93 (2000).

De Voss, J. J. et al. The salicylate-derived mycobactin siderophores of *Mycobacterium tuberculosis* are essential for growth in macrophages. Proc Natl Acad Sci USA 97, 1252-7. (2000).

Delogu, G. et al. Infect. Immun. 70, 293-302 (2002).

Dobos, K., Spotts, E., Quinn, F., & C. King. Infect. Immun. 68, 6300-6310 (2000).

Dolin, P. J., Raviglione, M. C. & A. Kochi. Global *tuberculosis* incidence and mortality during 1990-2000. Bull. World Health Organ. 72, 213-220 (1994).

Dubos, R. & W. Schaefer. Am. Rev. Tuberculous Pulm. Dis. 74, 541-551 (1956).

Dunn, P. L. & North, R. J. (1991) J Infect Dis 164, 869-877.

Dye, C., Scheele, S., Dolin, P., Pathania, V. & M. C. Raviglione. Consensus statement. Global burden of *tuberculosis*: estimated incidence, prevalence, and mortality by country. WHO Global Surveillance and Monitoring Project. JAMA 282, 677-686 (1999).

Elgert, K. D. Immunology, Wiley Liss, Inc., (1996).

Feng, C. G. et al. Increase in gamma interferon-secreting CD8(+), as well as CD4(+), T cells in lungs following aerosol infection with *Mycobacterium tuberculosis*. Infect. Immun. 67, 3242-7 (1999).

Fine, P. E. Lancet 346, 1339-45. (1995).

Fine, P. M. & Rodrigues, L. C. Modern vaccines: mycobacterial disease. Lancet 335, 1016-1020 (1990).

Finlay, B. B. & S. Falkow. Microbiol. Mol. Biol. Rev. 61, 136-69. (1997).

Flynn, J. L. & Chan, J. (2001) Annu Rev Immunol 19, 93-129.

Flynn, J. L., Chan, J., Triebold, K. J., Dalton, D. K., Stewart, T. A. & Bloom, B. R. (1993) J Exp Med 178, 2249-54.

Fritz, C., Maass, S., Kreft, A. & F. C. Bange. Infect. Immun 70, 286-91. (2002).

Gennaro, Ed. Remington's Pharmaceutical Sciences, 17th Edition, (Mack Publishing Co., Easton, Pa., 1985).

Gheorghiu, M. in Vaccinia, Vaccination, and Vaccinology: Jenner, Pasteur and their successors (eds. Plotkin, S. A. & Fantini, B.) 87-94 (Elsevier, Paris, 1996).

Glickman, M. S., Cox, J. S. & W. R. Jacobs, Jr. A novel mycolic acid cyclopropane synthetase is required for coding, persistence, and virulence of *Mycobacterium tuberculosis*. Mol. Cell. 5, 717-27 (2000).

Glickman, M. S., Cahill, S. M. & W. R. Jacobs, Jr. The *Mycobacterium tuberculosis* cmaA2 gene encodes a mycolic acid trans-cyclopropane synthetase. J. Biol. Chem. 276, 2228-33. (2001).

Gordon, S. V. et al. Genomics of *Mycobacterium bovis*. Tuberculosis 81, 157-63 (2001).

Grange, J. M., Gibson, J., Osborn, T. W., Collins, C. H. & M. D. Yates. What is BCG? Tubercle 64, 129-39. (1983).

Guleria, I. et al. Auxotrophic vaccines for *tuberculosis*. Nat. Med. 2, 334-7 (1996).

Hart, P. D. & I. Sutherland. BCG and vole *bacillus* vaccines in the prevention of *tuberculosis* in adolescence and early life. Br. Med. J. 22, 2293-2295 (1977).

Hepper, K. P. & F. M. Collins. Immune responsiveness in mice heavily infected with *M. kansasii*. Immunol. 53, 357-364 (1984).

Hernandez-Pando, R., Schon, T., Orozco, R., Serafin, J. & I. Estrada-Garcia. Exp. Tox. Path. 53, 257-265 (2001).

Homchampa, P., Strugnell, R. A. and B. Adler. Molecular analysis of the aroA gene of *Pasteurella multocida* and vaccine potential of a constructed aroA mutant. Mol Microbiol. 6, 3585-93 (1992).

Hondalus, M. K. et al. Attenuation of and protection induced by a leucine auxotroph of *Mycobacterium tuberculosis*. Infect. Immun. 68, 2888-98 (2000).

Honer zu Bentrup, K. & D. G. Russell. Trends Microbiol. 9, 597-605. (2001).

Hsu, T., Hingley-Wilson, S. M., Chen, B., Morin, P., Marks, C. B., Goulding, C., Gingery, M., Eisenberg, D., Russell, R. G., Derrick, S. C., Collins, F. M., Morris, S. L., King, C. H. & Jacobs Jr, W. R., Jr. (2003) Proc Natl Acad Sci USA 100, 12420-25.

Hubbard, R. D., Flory, C. M., Cocito, C. & F. M. Collins. Immunization of mice with antigen A60 of *Mycobacterium bovis* BCG. Clin. Exp. Immunol. 88, 129-131 (1992).

Hutter, B. & T. Dick. FEMS Microbiol. Lett 178, 63-9. (1999).

Jackowski, S. & J. H. Alix. J. Bacteriol. 172, 3842-8. (1990).

Jackowski, S. in *Escherichia coli and Salmonella typhimurium: Cellular and Molecular Biology*. F. C. Neidhardt, R. Curtiss, et al., Eds. (American Society for Microbiology, Washington, D.C., ed. Second, 1996).

Jackson, M. et al. Infect. Immun. 67, 2867-73. (1999).

Jacobs, W. R., Jr., Tuckman, M. & B. R. Bloom. Introduction of foreign DNA into mycobacteria using a shuttle phasmid. Nature 327, 532-5. (1987).

Jones, B. B. et al. Relationship of the manifestations of *tuberculosis* to CD4 cell counts in patients with human immunodeficiency virus infection. Am. Rev. Respir. Dis. 148, 1292-7 (1993).

Kalpana, G. V., Bloom, B. R. & W. R. Jacobs, Jr. Insertional mutagenesis and illegitimate recombination in mycobacteria. Proc. Natl. Acad. Sci. USA 88, 5433-7 (1991).

Kanai, K. & K. Yanagisawa. Jpn. J. Med. Sci. Biol. 8, 115-127 (1955).

Kaufmann, S. H., Ladel, C. H. & I. E. Flesch. T cells and cytokines in intracellular bacterial infections: experiences with Mycobacterium bovis BCG. Ciba Found. Symp. 195, 123-32 (1995).

Kaushal, D. et al. Reduced immunopathology and mortality despite tissue persistence in a *Mycobacterium tuberculosis* mutant lacking alternative sigma factor, SigH. Proc. Natl. Acad. Sci. USA 99, 8330-5. (2002).

Kirby, J. E., Vogel, J. P., Andrews, H. L. & R. R. Isberg. Mol. Microbiol. 27, 323-336 (1998).

Koch, R. Die Aetiologie der Tuberculos. Ber. Klin. Wochenschr. 19, 221-253 (1882).

Ladel, C. H., Daugelat, S. & Kaufmann, S. H. (1995) Eur J Immunol 25, 377-84.

Lalvani, A. et al. Human cytolytic and interferon gamma-secreting CD8+ T lymphocytes specific for *Mycobacterium tuberculosis*. Proc. Natl. Acad. Sci. USA 95, 270-5 (1998).

Lalvani, A. et al. J. Infect. Dis. 183, 469-477 (2001).

Lashuel, H. A. et al. Nature 418, 291 (2002).

Lee, M. H., Pascopella, L., Jacobs, W. R., Jr. & G. F. Hatfull. Site-specific integration of mycobacteriophage L5: integration-proficient vectors for *Mycobacterium smegmatis, Mycobacterium tuberculosis*, and bacille Calmette-Guerin. Proc. Natl. Acad. Sci. USA 88, 3111-5. (1991).

Lewis, K. N., Liao, R., Guinn, K. M., Hickey, M. J., Smith, S., Behr, M. A. & Sherman, D. R. (2003) J Infect Dis 187, 117-23.

Lewinsohn, D. M. et al. *Mycobacterium tuberculosis*-reactive CD8+ T lymphocytes: the relative contribution of classical versus nonclassical HLA restriction. J. Immunol. 165, 925-30 (2000).

Mahairas, G. G., Sabo, P. J., Hickey, M. J., Singh, D. C. & C. K. Stover. Molecular analysis of genetic differences between *Mycobacterium bovis* BCG and virulent *M. bovis*. J. Bacteriol 178, 1274-82 (1996).

Manca, C. et al. Virulence of a *Mycobacterium tuberculosis* clinical isolate in mice is determined by failure to induce Th1 type immunity and is associated with induction of IFN-alpha/beta. Proc. Natl. Acad. Sci. USA 98, 5752-7. (2001).

McAdam, R. A., et al. In vivo growth characteristics of leucine and methionine auxotrophic mutants of *Mycobacterium bovis* BCG generated by transposon mutagenesis. Infect. Immun. 63, 1004-12 (1995).

P. J. McGuire, P. J. et al. Appl. Env. Micro. 68, 4646-9 (2002).

McDonough, K. A. & Y. Kress. Infect. Immun. 63, 4802-4811 (1995).

McKenney, D. et al. Science 284, 1523-7. (1999).

McKinney, J. D. et al., Nature 406, 735-8. (2000).

Mintern, J. D., Davey, G. M., Belz, G. T., Carbone, F. R. & Heath, W. R. (2002) J Immunol 168, 977-80.

Mogues, T., et al. The relative importance of T cell subsets in immunity and immunopathology of airborne *Mycobacterium tuberculosis* infection in mice. J. Exp. Med. 193, 271-80 (2001).

Mohagheghpour, N., et al. CTL response to *Mycobacterium tuberculosis*: identification of an immunogenic epitope in the 19-kDa lipoprotein. J. Immunol. 161, 2400-6 (1998).

Morita, C. T., R. A. Mariuzza & M. B. Brenner. Antigen recognition by human gamma delta T cells: pattern recognition by the adaptive immune system. Springer Semin. Immunopathol. 22, 191-217 (2000).

Mukadi, Y., et al. Spectrum of immunodeficiency in HIV-1-infected patients with pulmonary *tuberculosis* in Zaire. Lancet 342, 1436 (1993).

Muller, I., et al. Impaired resistance to *Mycobacterium tuberculosis* infection after selective in vivo depletion of L3T4+ and Lyt-2+ T cells. Infect. Immun. 55, 2037-41 (1987).

Murray, C. J. & J. A. Salomon. Proc. Natl. Acad. Sci. USA 95, 13881-6. (1998).

Nassi, S. et al. Biochemistry 41, 1445-1450 (2002).

North, R. J., Ryan, L., LaCource, R., Mogues, T. & Goodrich, M. E. (1999) Infect Immun 67, 5483-5.

Opie, E. L. & J. Freund J. An experimental study of protective inoculation with heat killed tubercule bacilli. J. Exp. Med. 66, 761-788 (1937).

Ottenboff, T. H., Kumararatne, D. & Casanova, J. L. (1998) Immunol Today 19, 491-4.

Pablos-Mendez, A., Raviglione, M. C., Laszlo, A., Binkin, N., Rieder, H. L., Bustreo, F., Cohn, D. L., Lambregts-van Weezenbeek, C. S., Kim, S. J., Chaulet, P. & Nunn, P. (1998) N Engl J Med 338, 1641-9. pp. 531-557.

Pallen, M. Trends in Microbiol. 10, 209-212 (2002).

Parish, T. & N. G. Stoker. Use of a flexible cassette method to generate a double unmarked *Mycobacterium tuberculosis* tlyA plcABC mutant by gene replacement. Microbiol. 146, 1969-1975 (2000).

Pascopella, L. et al. Use of in vivo complementation in *Mycobacterium tuberculosis* to identify a genomic fragment associated with virulence. Infect. Immun. 62, 1313-9. (1994).

Pavelka, M. S., Jr. & W. R. Jacobs, Jr. Comparison of the construction of unmarked deletion mutations in *Mycobacterium smegmatis, Mycobacterium bovis* bacillus Calmette-Guerin, and *Mycobacterium tuberculosis* H37Rv by allelic exchange. J. Bacteriol. 181, 4780-9 (1999).

Pedrazzini, T., Hug, K. & J. A. Louis Importance of L3T4+ and Lyt-2+ cells in the immunologic control of infection with *Mycobacterium bovis* strain *bacillus* Calmette-Guerin in mice. Assessment by elimination of T cell subsets in vivo. J. Immunol. 139, 2032-7 (1987).

Pelicic, V., Reyrat, J. M. & B. Gicquel. Generation of unmarked directed mutations in mycobacteria, using sucrose counter-selectable suicide vectors. Mol. Microbiol. 20, 919-25. (1996).

Pelicic, V. et al. Efficient allelic exchange and transposon mutagenesis in *Mycobacterium tuberculosis*. Proc. Natl. Acad. Sci. USA 94, 10955-60 (1997).

Pethe, K. et al. Nature 412, 190-194 (2001).

Petroff, S. A., Branch, A. & W. Steenken, Jr. A study of *Bacillus* Calmette-Guerin. 1. Biological characteristics, cultural 'dissociation' and animal experimentation. Am. Rev. Tuberc. 9, 46 (1929).

Prasad, P. D. et al. J. Biol. Chem. 273, 7501-6. (1998).

Prasad, P. D. & V. Ganaphthy. Curr. Opin. Clin. Nutr. Metab. Care 3, 263-6. (2000).

Pym, A. S. et al. Mol. Microbio. 46, 709-717 (2002).

Raman, S. et al. The alternative sigma factor SigH regulates major components of oxidative and heat stress responses in *Mycobacterium tuberculosis*. J. Bacteriol. 183, 6119-25. (2001).

Renshaw, P. et al. J. Biol. Chem. 277, 21598-21603 (2002).

Rodrigues, L. C., Gill, N. & Smith, P. G. BCG vaccination in the first year of life protects children of Indian subcontinent ethnic origin against *tuberculosis* in England. J. Epidemiol. 45, 78-80 (1991).

Rodrigues, L. C., Diwan, V. K & Wheeler, J. G. (1993) Int J Epidemiol 22, 1154-8.

Rosat, J. P. et al. CD1-restricted microbial lipid antigen-specific recognition found in the CD8+ alpha beta T cell pool. J. Immunol. 162, 366-71 (1999).

Saliba, K. J. & K. Kirk. J. Biol. Chem. 276, 18115-21 (2001).

Sambandamurthy, V. K. et al. Nature Med. 10, 1171-4 (2002).

Scanga, C. A. et al. Depletion of CD4(+) T cells causes reactivation of murine persistent *tuberculosis* despite continued expression of interferon gamma and nitric oxide synthase 2. J. Exp. Med. 192, 347-58 (2000).

Seder, R. A. & Hill, A. V. (2000) Nature 406, 793-8.

Serbina, N. V. and J. L. Flynn. CD8(+) T cells participate in the memory immune response to *Mycobacterium tuberculosis*. Infect. Immun. 69, 4320-8 (2000).

Shen, Y. et al. Antiretroviral agents restore Mycobacterium-specific T-cell immune responses and facilitate controlling a fatal *tuberculosis*-like disease in Macaques coinfected with simian immunodeficiency virus and *Mycobacterium bovis* BCG. J. Virol. 75, 8690-6 (2001).

Shen, Y., Zhou, D., Chalifoux, L., Simon. M., Shen, L., Li, P., Sehgal, P. K., Letvin, N. L. & Z. W. Chen. Induction of an simian immunodeficiency virus-related *tuberculosis*-like disease in macaques: An animal model for AIDS virus/mycobacterium coinfection. Infect. Immun. 70, 869-77 (2001).

Silva, C. L. & D. B. Lowrie. Identification and characterization of murine cytotoxic T cells that kill *Mycobacterium tuberculosis*. Infect. Immun. 68, 3269-74 (2000).

Skjot, R. et al., Infect. Immun. 68, 214-220 (2000).

Slyshenkov, V. S., Rakowska, M., Moiseenok., A. G. & L. Wojtczak. Free Radic. Biol. Med. 19, 767-72. (1995).

Slyshenkov, V. S., Moiseenok, A. G. & Wojtczak, L. Noxious effects of oxygen reactive species on energy-coupling processes in Ehrlich ascites tumor mitochondria and the protection by pantothenic acid. Free Radic Biol Med 20, 793-800 (1996).

Slyshenkov, V. S., Piwocka, K., Sikora, E. & L. Wojtczak. Free Radic. Biol. Med. 30, 1303-10. (2001).

Smith, D. A., Parish, T. Stoker, N. G. & G. J. Bancroft, Infect. Immun. 69, 1142-50. (2001).

Snapper, S. B. et al. Lysogeny and transformation in mycobacteria: stable expression of foreign genes. Proc. Natl. Acad. Sci. USA 85, 6987-91. (1988).

Sousa, A. O. et al. Relative contributions of distinct MHC class I-dependent cell populations in protection to *tuberculosis* infection in mice. Proc. Natl. Acad. Sci. USA 97, 4204-8 (2000).

Sousa, A. O., Mazzaccaro, R. J., Russell, R. G., Lee, F. K., Turner, O. C., Hong, S., Van Kaer, L. & Bloom, B. R. (2000) Proc Natl Acad Sci USA 97, 4204-8.46. Serbina, N. V. & Flynn, J. L. (2001) Infect Immun 69, 4320-8.

Stenger, S. et al. Differential effects of cytolytic T cell subsets on intracellular infection. Science 276, 1684-7 (1997).

Stites et al. Basic & Clinical Immunology; 7th Ed., Appleton & Lange, (1991).

Stevenson, P. G., Belz, G. T., Altman, J. D. & Doherty, P. C. (1998) Proc Natl Acad Sci USA 95, 15565-70.

Steyn, A. J. et al. *Mycobacterium tuberculosis* WhiB3 interacts with RpoV to affect host survival but is dispensable for in vivo growth. Proc. Natl. Acad. Sci. USA 99, 3147-52. (2002).

Talbot, E. A., Perkins, M. D., Silva, S. F. & Frothingham, R. (1997) Clin Infect Dis 24, 1139-46.

Teitelbaum, R. et al. Immun. 10, 641-50 (1999).

Theuer, C. P. et al. Human immunodeficiency virus infection in *tuberculosis* patients. J Infect Dis. 162, 8-12 (1990).

Tuberculosis Prevention Trial. Trial of BCG vaccines in South India for *tuberculosis* prevention. Indian J. Med. Res. 72, 1-74 (1980).

Vallari, D. S. & C. O. Rock. J. Bacteriol. 164, 136-42. (1985).

van Pinxteren, L. et al. Clin. Diagn. Lab. Immunol. 7, 155-160 (2000a).

van Pinxteren, L. A., Cassidy, J. P., Smedegaard, B. H., Agger, E. M. & Andersen, P. (2000b) Eur J Immunol 30, 3689-98.

Wang, B., Norbury, C. C., Greenwood, R., Bennink, J. R., Yewdell, J. W. & Frelinger, J. A. (2001) J Immunol 167, 1283-9.

Weltman, A. C. & Rose, D. N. (1993) Aids 7, 149-57.

Weber, I., Fritz, C., Ruttkowski, S., Kreft, A. & Bange, F. C. (2000) Mol Microbiol 35, 1017-25. 32. Dalton, D. K., Pitts-Meek, S., Keshav, S., Figari, I. S., Bradley, A. & Stewart, T. A. (1993) Science 259, 1739-42.

Weber, I., Fritz, C., Ruttkowski, S., Kreft, A. & F. C. Bange. Mol. Microbiol. 35, 1017-25. (2000).

Weill-Halle, B. & Turpin, R. Premiers essais de vaccination antituberculeuse de l'enfant par le bacille Calmette-Guerin (BCG). Bulletins et Memories de la Societe Medicale des Hopitaux de Paris 49, 1589 (1925).

Whalen, C. C., Nsubuga, P., Okwera, A., Johnson, J. L., Hom, D. L., Michael, N. L., Mugerwa, R. D. & Ellner, J. J. (2000) Aids 14, 1219-28.

Wild, J., Grusby, M. J., Schirinbeck, R. & Reimann, J. (1999) J Immunol 163, 1880-7.

Wuthrich, M., Filutowicz, H. I., Warner, T., Deepe, G. S., Jr. & Klein, B. S. (2003) J Exp Med 197, 1405-16.

U.S. Pat. No. 6,271,034.

U.S. Pat. No. 5,504,005.

There exists an urgent need for a novel *tuberculosis* (TB) vaccine as there are more than 8 million new cases of *tuberculosis* and more than 2 million deaths reported each year by the WHO (Dye et al., 1999). The discovery of the causative agent of TB, *Mycobacterium tuberculosis*, by Robert Koch in 1882 opened up the possibility for a novel vaccine (Koch, 1882). Since then, numerous attempts to develop attenuated vaccines against *tuberculosis* have failed, including tuberculin (a protein extract of killed tubercle bacilli) developed by Dr. Koch himself. This failure of tuberculin to protect led to a "firm conviction that immunity could only be established by inducing a definite, albeit limited, *tuberculosis* process" (Grange et al., 1983). Thus, numerous labs set out to follow the example of Dr. Louis Pasteur for viruses and enrich attenuated mutants of the tubercle *bacillus* following repeated passaging.

In order to test the hypothesis that a tubercle bacillus isolated from cattle (now known as *M. bovis*) could transmit pulmonary tuberculosis following oral administration, Drs. Calmette and Guerin developed a medium containing beef bile that enabled the preparation of fine homogenous bacillary suspensions (Calmette and Guerin, 1905). An *M. bovis* strain obtained from Dr. Norcard, was passaged every 21 days in this medium and after the 39th passage, the strain was found to be unable to kill experimental animals (Gheorghiu, 1996). "Between 1908 and 1921, the strain showed no reversion to virulence after 230 passages on bile potato medium" (Id.), which is consistent with the attenuating mutation being a deletion mutation. In the animal studies that followed, the strain ('BCG') was found to be attenuated but it also protected animals receiving a lethal challenge of virulent tubercle bacilli (Calmette and Guerin, 1920). BCG was first used as a vaccine against tuberculosis in 1921. From 1921 to 1927, BCG was shown to have protective efficacy against TB in a study on children (Weill-Halle and Turpin, 1925; Calmette and Plotz, 1929) and adopted by the League of Nations in 1928 for widespread use in the prevention of tuberculosis. By the 1950's after a series of clinical trials, the WHO was encouraging widespread use of BCG vaccine throughout the world (Fine and Rodrigues, 1990). Although an estimated 3 billion doses have been used to vaccinate the human population against tuberculosis, the mechanism that causes BCG's attenuation remains unknown.

Mahairas et al. (1996) first compared the genomic sequences of BCG and *M. bovis* using subtractive hybridization and found that there were three major deletions (named RD1, RD2, and RD3) present in the genome of *M. bovis*, but missing in BCG. Behr et al. (1999) and others (Gordon et al., 2001) later identified 16 large deletions, including RD1 to RD3, present in the BCG genome but absent in *M. tuberculosis*. These authors concluded that 11 of these 16 deletions were unique to *M. bovis*, while the remaining 5 deletions were unique to BCG. They also found that one of these 5 deletions, designated RD1 (9454 bp), is present in all of the BCG substrains currently used as TB vaccines worldwide and concluded that the deletion of RD1 appeared to have occurred very early during the development of BCG, probably prior to 1921 (Behr et al., 1999).

The development of insertional mutagenesis systems for BCG and *M. tuberculosis* (Kalpana et al., 1991), transposon mutagenesis systems (Cirillo et al., 1991; McAdam et al., 1995; Bardarov et al., 1997) and allelic exchange systems (Balasubramanian et al., 1996; Pelicic et al., 1997) led to the isolation of the first auxotrophic (nutrient-requiring) mutants of these slow-growing mycobacteria. Auxotrophic mutants of BCG and *M. tuberculosis* have been shown to confer protection to *M. tuberculosis* challenges with variable efficacies (Guleria et al., 1996; Smith et al., 2001). However, a head-to-head comparison of BCG to a leucine auxotroph of BCG showed that a single immunization elicited no positive skin-test and imparted little immunity to challenges with *M. tuberculosis* or *M. bovis* (Chambers et al., 2000). In contrast, a methionine auxotroph of BCG that grows in vivo did confer significant protection to challenge to both *M. tuberculosis* and *M. bovis* (Id.). A single dose of a leucine auxotroph of *M. tuberculosis* failed to elicit protection as good as BCG in BALB/c mice (Hondalus et al., 2000). These results suggest that optimal immunity against *M. tuberculosis* requires some growth of the immunizing strain. Double mutants of *M. tuberculosis* have also been created (Parish and Stoker, 2000), but whether such mutants are improved over single attenuating mutants in protecting mammals against challenge with a virulent mycobacterium, particularly when the host is immunocompromised, has not been established.

It is also worth noting that in the study of Chambers et al. (2000), both BCG and the BCG mutants seemed to protect better against *M. bovis* challenge than *M. tuberculosis*. If we assume the reverse correlate is true, we could hypothesize that optimal immunity against *M. tuberculosis* could be achieved with a *M. tuberculosis*-derived mutant that grew in the mammalian host.

Based on the above, there remains a need for improved live mycobacterial vaccines having attenuated virulence, that confer protection from virulent mycobacteria, particularly *M. tuberculosis*. The need is particularly acute for immunocompromised individuals. The instant invention satisfies that need.

SUMMARY OF THE INVENTION

The present invention is based on the discovery that mycobacteria having two attenuating mutations are safe and protect mammals that are deficient in CD4+ and/or CD8+ lymphocytes from challenge by virulent mycobacteria.

Thus, the present invention is directed to methods of treating a mammal that does not have severe combined immune deficiency but is deficient in CD4+ lymphocytes. The methods comprise inoculating the mammal with an attenuated *mycobacterium* in the *Mycobacterium tuberculosis* (*M. tuberculosis*) complex. In these embodiments, the mycobacterium comprises two deletions, where a virulent mycobacterium in the *M. tuberculosis* complex having either deletion exhibits attenuated virulence.

The invention is also directed to methods of treating a mammal that does not have severe combined immune deficiency but is deficient in CD8+ lymphocytes. The methods comprise inoculating the mammal with an attenuated mycobacterium in the *Mycobacterium tuberculosis* (*M. tuberculosis*) complex. In these embodiments, the mycobacterium comprises two deletions, where a virulent mycobacterium in the *M. tuberculosis* complex having either deletion exhibits attenuated virulence.

Additionally, the invention is directed to the use of an attenuated mycobacterium in the *Mycobacterium tuberculosis* (*M. tuberculosis*) complex for the manufacture of a medicament for treatment of a mammal that is that does not have severe combined immune deficiency but is deficient in CD4+ lymphocytes. In these embodiments, the mycobacterium comprises two deletions, where a virulent mycobacterium in the *M. tuberculosis* complex having either deletion exhibits attenuated virulence.

In other embodiments, the invention is directed to the use of an attenuated mycobacterium in the *Mycobacterium tuberculosis* (*M. tuberculosis*) complex for the manufacture of a medicament for treatment of a mammal that does not have severe combined immune deficiency but is deficient in CD8+ lymphocytes. In these embodiments, the mycobacterium comprises two deletions, where a virulent mycobacterium in the *M. tuberculosis* complex having either deletion exhibits attenuated virulence.

DETAILED DESCRIPTION OF THE INVENTION

Figure 1:
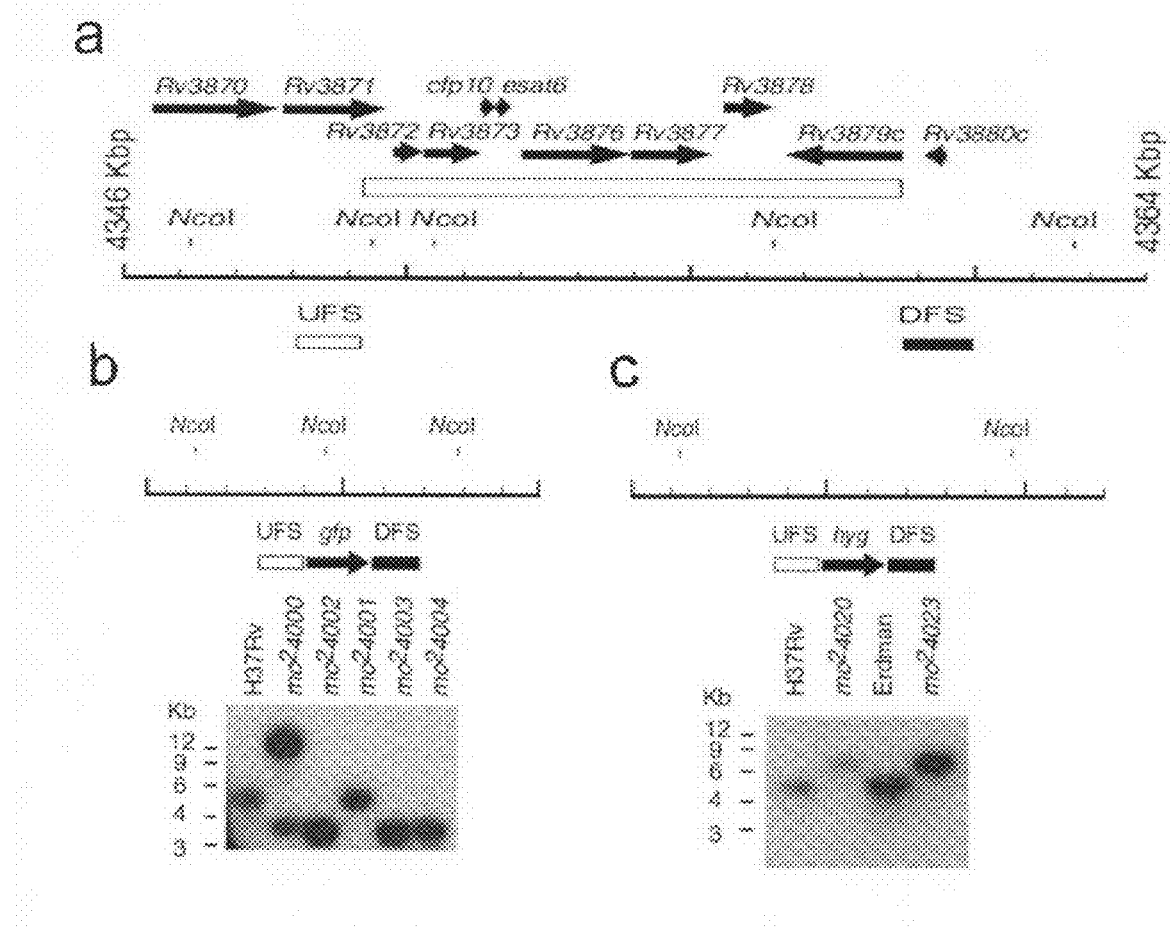
FIG. 1 shows maps and autoradiographs pertaining to the construction of ΔRD1 mutants of *M. tuberculosis*. Panel a, *M. tuberculosis* H37Rv published sequence between 4346 kb and 4364 kb, showing predicted NcoI sites. Arrows on the top represent the genes in the RD1 region. The RD1 region deleted from *M. bovis* BCG is represented by an open bar spanning from Rv3871 to Rv3879c. Upstream and downstream flanking sequences, UFS and DFS respectively, are indicated as closed bars underneath the grid line. Panel b, Southern hybridization of *M. tuberculosis* H37Rv ΔRD1 created using two-step sequential homologous recombination. Panel c, Southern hybridization of *M. tuberculosis* H37Rv and Erdman ΔRD1 strains created using specialized transduction.

The present invention is based on the discovery that mycobacteria having two attenuating mutations are safe and protect mammals that are deficient in CD4$^+$ lymphocytes from challenge by virulent mycobacteria. See Examples 6 and 7. This anti-mycobacterial immunity also does not depend on CD8$^+$ cells (Example 7).

Thus, the present invention is directed to methods of treating a mammal that does not have severe combined immune deficiency but is deficient in CD4$^+$ lymphocytes. The methods comprise inoculating the mammal with an attenuated mycobacterium in the *Mycobacterium tuberculosis* (*M. tuberculosis*) complex. In these embodiments, the mycobacterium comprises two deletions, where a virulent mycobacterium in the *M. tuberculosis* complex having either deletion exhibits attenuated virulence. The mammal in these embodiments can have CD8$^+$ lymphocytes that are elevated (as can occur in AIDS patients), normal or deficient (see Example 7).

The protection afforded by those double mutants in mammals deficient in CD4$^+$ lymphocytes is surprising because it was previously believed that CD4$^+$ lymphocytes were crucial in establishing immunity against *tuberculosis* (Jones et al., 1993; Scanga et al., 2000). The instant discovery establishes that such mutants would be expected to be safe and effective in providing protection against *tuberculosis* in individuals with highly compromised immunity, such as individuals with HIV infection or those taking immunosuppressant drugs (e.g., transplant patients).

As used herein, a mammal that is deficient in CD4$^+$ lymphocytes has less than about 500 CD4$^+$ cells per mm$^3$ of blood. The CD4$^+$ deficient mammal can also have less than about 350 or 200 or 100 or 50 cells per mm$^3$ of blood. The CD4$^+$ deficient mammal can even be devoid of CD4$^+$ lymphocytes. A mammal that is deficient in CD8$^+$ lymphocytes has less than about 200 CD8$^+$ cells per mm$^3$ of blood. The CD8$^+$ deficient mammal can also have less than about 100 or 50 or 25 CD8$^+$ cells per mm$^3$ of blood. The CD4$^+$ deficient mammal can also be devoid of CD4$^+$ lymphocytes.

The mammal can be inoculated with the mycobacteria in the methods of the present invention by any of a number of ways known in the art. Non-limiting examples include oral ingestion, gastric intubation, or broncho-nasal-ocular spraying. Other methods of administration include intravenous, intramuscular, intramammary, or, preferably, subcutaneous or intradermal injection. The immunization dosages required can be determined without undue experimentation. One or two dosages of avirulent mycobacteria at 1-2×10$^6$ colony forming units (CFU) have previously been used, but other dosages are contemplated within the scope of the invention. Multiple dosages can be used as needed to provide the desired level of protection from challenge.

The above-described mycobacterial compositions can be formulated without undue experimentation for administration to a mammal, including humans, as appropriate for the particular application.

Accordingly, the mycobacterial compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral administration, the mycobacterial compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The mycobacterial compositions of the present invention can easily be administered parenterally such as for example, by intravenous, intramuscular, intrathecal or subcutaneous injection. Parenteral administration can be accomplished by incorporating the mycobacterial compositions of the present invention into a suspension. Such suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the mycobacterial compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

The present invention also includes nasally administering to the mammal a therapeutically effective amount of the mycobacterial composition. As used herein, nasally administering or nasal administration includes administering the composition to the mucous membranes of the nasal passage or nasal cavity of the patient. As used herein, mycobacterial compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

It is well known in the art that in order to elicit an immune response with a live vaccine such as an avirulent mycobacteria, it is preferred that the vaccine organism can sustain an infection in the immunized host, to provide a sustained exposure of the host's immune system to the organism. Therefore, in various preferred embodiments, the mycobacteria used in the methods of the invention are capable of sustaining an infection in the host. The ability to sustain infection can be measured without undue experimentation by any of a number of ways described in the art. With the mycobacteria used in the methods of the present invention, a preferred way of measuring sustained infection is by determining whether viable mycobacteria of the inoculated strain will remain resident in an immunocompetent mouse (e.g., BALB/c or C57BL/6 strain) for more than four weeks. More preferably, the inoculated mycobacteria will remain resident in the mouse for at least ten weeks. In the most preferred embodiments, viable mycobacteria of the inoculated strain will remain resident in the mouse for at least 20 weeks.

Preferably, the attenuated mycobacteria used in the methods of the invention are capable of protecting a mammal from challenge by a virulent *M. tuberculosis* complex mycobacteria. This ability can be determined by any of a number of ways provided in the literature. A preferred method is aerogenically treating an immunocompetent mouse with the virulent mycobacteria, as described in Examples 1 and 2. Aerogenic challenge is preferred because that most closely mimics natural infection. The skilled artisan would understand that the ability of an avirulent mycobacterium to protect a mouse from challenge from a virulent mycobacterium is indicative of the ability of the avirulent mycobacterium to protect a human, including a human child, from *tuberculosis* infection. A more stringent test of an avirulent mycobacterium to prevent infection by a virulent challenge is to use an immunocompromised mammal, e.g. a SCID mouse or a mouse deficient in CD4 or interferon γ production.

The scope of the present invention includes the use of mycobacteria in the *M. tuberculosis* complex that comprise two attenuating deletions, where at least one of the attenuating deletion was made using genetic engineering. As discussed above, examples of such deletions include deletions of an RD1 region, deletions of a region controlling production of a vitamin, and deletions of a region controlling production of an amino acid. These mycobacteria include any in the *M. tuberculosis* complex, including *M. africanum, M. bovis* including the BCG strain and the subspecies *caprae, M. canettii, M. microti, M. tuberculosis* and any other mycobacteria within the *M. tuberculosis* complex, now known or later discovered. Preferred species are *M. bovis*, including the BCG strain, and *M. tuberculosis*, since those species are the most important as causes of mammalian diseases, such as *tuberculosis* in humans and *M. bovis* infection in cows.

In some aspects of these embodiments, at least one of the two deletions is of the RD1 region (see Example 1). Strains with these deletions can be determined by any means in the art, preferably by molecular genetic means, for example by hybridization methods (e.g., Southern blot using a probe from the RD1 region) or by amplification methods (e.g., PCR using primers to amplify a portion of the RD1 region). An example of an *M. tuberculosis* RD1 region (from H37Rv) is provided herein as SEQ ID NO:1. The skilled artisan could identify analogous RD1 regions from other mycobacteria in the *M. tuberculosis* complex without undue experimentation. Those RD1 regions would be expected to have strong homology to SEQ ID NO:1, at least 80% homologous to SEQ ID NO:1. However, it is to be understood that virulent mycobacteria in the *M. tuberculosis* complex can be rendered avirulent by deletions in a portion of the RD1 region. Therefore, use of non-naturally occurring mycobacteria in the *M. tuberculosis* complex that have a partial deletion in the RD1 region are envisioned as within the scope of the invention, provided the deletion can cause a virulent *M. tuberculosis* to become avirulent. It is expected that such *M. tuberculosis* with partial RD1 deletions can still sustain an infection in a mammal and protect against challenge by a virulent *M. tuberculosis*.

In embodiments where at least one of the deletions is in a region controlling production of a vitamin, the deletion can be in any genetic element leading to loss of production of the vitamin, including structural genes for enzymes involved in the biosynthesis of the vitamin, and genetic control elements such as promoters, enhancers, etc.

Deletion of a region controlling production of any essential vitamin or their precursors is contemplated as within the scope of the invention. As used herein, an essential vitamin is defined by its normal usage, that is, a small molecular weight compound that is required as a cofactor for the efficient function of an essential enzyme or enzymes. Nonlimiting examples include vitamin A, thiamin (B1), riboflavin (B2), nicotinic acid (niacin)/nicotinamide/nicotinamide adenine dinucleotide (NAD)/nicotinamide adenine dinucleotide phosphate (NADP/coenzyme II), pantothenate (pantothenic acid/B5), pyridoxine (B6), folic acid, B12, biotin, C, D, E and K. Preferred vitamin targets for deletion include nicotinamide and pantothenate (see Example 2). Methods for determining whether a mycobacterium has deletions leading to the loss of production of any of these vitamins are within the scope of the art.

Deletions leading to the loss of any of these vitamins would be expected to lead to attenuated virulence of an otherwise virulent mycobacterium in the *M. tuberculosis* complex. Any of those strains would also be expected to sustain an infection in a mammal.

Preferred vitamin targets are pantothenate and nicotinamide adenine dinucleotide (NAD)(see Example 2). A preferred pantothenate deletion is of structural genes in the pantothenate biosynthetic operon, most preferably the pan C and D genes, the combined mutation being ΔpanCD. An example of a deletion of those genes is the deletion of the sequence from *M. tuberculosis* H37Rv provided herein as SEQ ID NO:2. Similarly, a preferred NAD deletion is in the structural genes of the NAD biosynthetic operon, most preferably the nadB and nadC genes, the combined mutation being ΔnadBC. An example of a deletion in those genes is the deletion of the sequence from *M. tuberculosis* H37Rv provided herein as SEQ ID NO:3.

In other embodiments, at least one of the attenuating deletions is of a region controlling production of an amino acid. Preferred examples include deletions of a region controlling production of proline, tryptophan, leucine or lysine. When the amino acid is lysine, a preferred deletion is a ΔlysA deletion, e.g., SEQ ID NO:4.

The mycobacterium deletions can be made by serial in vitro passage of a virulent *M. tuberculosis* (as the well-known *M. bovis* BCG was made) and selection for the desired deletion. More preferably, however, the deletion is made by genetic engineering, since such genetic methods allow precise control of the deletion being made.

Various methods of making deletions in mycobacteria are known in the art. Nonlimiting examples include specialized transduction (see, e.g., U.S. Pat. No. 6,271,034, Example 1 and Example 2), and sequential two-step recombination (see Example 1). The latter method can usefully employ a sacB selective marker (Example 1).

Since, in preferred embodiments of the invention, the mycobacteria exhibit attenuated virulence and can sustain an infection in a mammal, these mycobacteria can usefully further employ a foreign DNA stably integrated into the genome of the mycobacteria, such that the mycobacteria can express a gene product coded by the foreign DNA. See, e.g., U.S. Pat. No. 5,504,005.

Thus, the present invention has wide applicability to the development of effective recombinant vaccines in mammals deficient in $CD4^+$ lymphocytes against bacterial, fungal, parasite or viral disease agents in which local immunity is important and might be a first line of defense. Non-limiting examples are recombinant vaccines for the control of bubonic plague caused by *Yersinia pestis*, of gonorrhea caused by *Neisseria gonorrhoeae*, of syphilis caused by *Treponema pallidum*, and of venereal diseases or eye infections caused by *Chlamydia trachomatis*. Species of *Streptococcus* from both group A and group B, such as those species that cause sore throat or heart disease, *Neisseria meningitidis, Mycoplasma pneumoniae, Haemophilus influenzae, Bordetella pertussis, Mycobacterium leprae, Streptococcus pneumoniae, Brucella abortus, Vibrio cholerae, Shigella* spp., *Legionella pneumophila, Borrelia burgdorferi, Rickettsia* spp., *Pseudomonas aeruginosa*, and pathogenic *E. coli* such as ETEC, EPEC, UTEC, EHEC, and EIEC strains are additional examples of microbes within the scope of this invention from which foreign genes could be obtained for insertion into mycobacteria of the invention. Recombinant anti-viral vaccines, such as those produced against influenza viruses, are also encompassed by this invention. Recombinant anti-viral vaccines can also be produced against viruses, including RNA viruses such as Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae or Retroviridae; or DNA viruses such as Hepadnaviridae, Paroviridae, Papovaviridae, Adenoviridae, Herpesviridae or Poxyiridae.

The use of these methods for administering recombinant vaccines to protect against infection by pathogenic fungi, protozoa or parasites are also contemplated by this invention.

The avirulent microbes used in the methods of the present invention are also contemplated for use to deliver and produce foreign genes that encode pharmacologically active products that might stimulate or suppress various physiological functions (i.e., growth rate, immune-stimulating cytokines, blood pressure, etc.) in $CD4^+$-deficient mammals. In such microbes, the recombinant gene encodes said pharmacologically active products.

By immunogenic agent is meant an agent used to stimulate the immune system of an individual, so that one or more functions of the immune system are increased and directed towards the immunogenic agent. Immunogenic agents include vaccines.

An antigen or immunogen is intended to mean a molecule containing one or more epitopes that can stimulate a host immune system to make a secretory, humoral and/or cellular immune response specific to that antigen.

In preferred embodiments, the foreign DNA encodes an antigen, an enzyme, a lymphokine, an immunopotentiator, or a reporter molecule. Preferred examples include antigens from *Mycobacterium leprae, Mycobacterium tuberculosis*, malaria sporozoites, malaria merozoites, diphtheria toxoid, tetanus toxoids, *Leishmania* spp., *Salmonella* spp., *Mycobacterium africanum, Mycobacterium intracellulare, Mycobacterium avium, Treponema* spp., Pertussis, Herpes virus, Measles virus, Mumps virus, *Shigella* spp., *Neisseria* spp., *Borrelia* spp., rabies, polio virus, human immunodeficiency virus, snake venom, insect venom, and *Vibrio cholera*; steroid enzymes; interleukins 1 through 7; tumor necrosis factor α and β; interferon α, β, and γ; and reporter molecules luciferase, β-galactosidase, β-glucuronidase and catechol dehydrogenase.

It has also been discovered that the attenuated mycobacteria discussed above can safely be used to inoculate mammals deficient in $CD8^+$ lymphocytes, for example mammals that are immunosuppressed, or mammals that have a mutation in a CD8 gene (see, e.g., de la Calle-Marin et al., 2001). See Example 7.

Thus, the invention is also directed to methods of treating a mammal that does not have severe combined immune deficiency but is deficient in $CD8^+$ lymphocytes. The methods comprise inoculating the mammal with an attenuated mycobacterium in the *Mycobacterium tuberculosis* (*M. tuberculosis*) complex. In these embodiments, the mycobacterium comprises two deletions, where a virulent mycobacterium in the *M. tuberculosis* complex having either deletion exhibits attenuated virulence. The mammals in these methods can have normal levels of $CD4^+$ lymphocytes, or have deficient or elevated levels of $CD4^+$ lymphocytes.

These embodiments are entirely analogous to the embodiments discussed above relating to the treatment of mammals deficient in $CD4^+$ lymphocytes. This includes the use of any of the above-described attenuated *M. tuberculosis* strains and any of the inoculation methods described above. The methods can also be used in any mammal, including humans, such as adults or children.

Additionally, the invention is directed to the use of an attenuated mycobacterium in the *Mycobacterium tuberculosis* (*M. tuberculosis*) complex for the manufacture of a medicament for treatment of a mammal that does not have severe combined immune deficiency but is deficient in $CD4^+$ lymphocytes, or $CD8^+$ lymphocytes. In these embodiments, the mycobacterium is as described for the embodiments discussed above, i.e., it comprises two deletions, where a virulent mycobacterium in the *M. tuberculosis* complex having either deletion exhibits attenuated virulence. Methods of manufacture of such medicaments, including formulations as vaccines, are well known in the art and would not require undue experimentation. These uses are suitable for any mammal, including humans, such as adults or children.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I-IV Ausubel, R. M., ed. (1997); and "Cell Biology: A Laboratory Handbook" Volumes I-III J. E. Celis, ed. (1994).

EXAMPLE 1

Mycobacterium Tuberculosis Having an RD1 Deletion has Attenuated Virulence and Protects Against Tuberculosis This example describes experimental methods and results that establish that deleting the RD1 region from a virulent M. tuberculosis attenuates the virulence of the M. tuberculosis in both immunocompetent and immunocompromised mice, and protects against subsequent challenge by a virulent M. tuberculosis.

Materials and Methods

Media and Cultures. The mycobacterial strains M. tuberculosis H37Rv, M. tuberculosis Erdman and M. bovis BCG Pasteur were obtained from the Trudeau Culture Collection (Saranac Lake, N.Y.). They were cultured in Middlebrook 7H9 broth and 7H10 agar supplemented with 10% OADC, 0.5% glycerol, and 0.05% Tween 80. Cyclohexamide, which does not affect mycobacterial growth, was added to the 7H10 agar medium at 0.1% to avoid fungal contamination. To examine the colony morphology of mycobacteria, Tween 80 was not added to 7H10 agar medium. The acriflavin resistant strain (Hepper and Collins, 1984) of M. tuberculosis Erdman grew in the presence of 20 μg of acriflavin per ml of medium.

DNA manipulation and construction of M. tuberculosis ΔRD1. The following four primers were used to amplify upstream and downstream flanking sequences (UFS and DFS, respectively) for the construction of the RD1 deletion mutants. UFS was amplified using TH201: GGGGGCG-CACCTCAAACC (SEQ ID NO:5) and TH203: ATGTGC-CAATCGTCGACCAGAA (SEQ ID NO:6). DFS was amplified using TH203: CACCCAGCCGCCCGGAT (SEQ ID NO:7), and TH204: TTCCTGATGCCGCCGTCTGA (SEQ ID NO:8). Recognition sequences for different restriction enzymes were included at the ends of each primer to enable easier manipulation.

The unmarked deletion mutant of M. tuberculosis H37Rv, mc²4004, was generated by transformation (Snapper et al., 1988) using a sacB counterselection (Pelocic et al., 1996; Pavelka and Jacobs, 1999). Specifically, the plasmid pJH508 was created by first cloning UFS into KpnI and XbaI sites, then cloning DFS into EcoRI and HindIII sites of pJH12, a pMV261-derived E coli-Mycobacteria shuttle plasmid, to create pJH506 in which UFS and DFS flanked a green fluorescent protein gene (GFPuv, Clonetech) whose expression was driven by the M. leprae promoter 18 Kd. The UFS-gfp-DFS cassette was sub-cloned into the EcoRV site of plasmid pYUB657 to create pJH508. The first homologous recombination involved the identification of hygromycin resistant colonies, resulting from the transformation of M. tuberculosis with pJH508. Southern analysis of the NcoI digested DNA isolated from hygromycin resistant colonies probed with UFS or DFS, confirmed the presence of a single copy of pJH508 inserted into the M. tuberculosis genome. The transformant identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

Specialized transduction (Bardarov and Jacobs, 1999), a mycobacteriophage-based method for the delivery of homologous DNA constructs using conditionally replicating shuttle phasmids (Jacobs et al, 1987; Bardarov and Jacobs, 1999; Carriere et al., 1997), has been used successfully for M. tuberculosis (Glickman et al., 2000; Glickman et al., 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature sensitive mycobacteriophage derived from TM4. The transduction was performed by growing M. tuberculosis to an $O.D._{600}$ of 0.8, washing twice with MP buffer, re-suspending into an equal volume of MP buffer and mixing with the transducing phage phAEKO1 at an MOI of 10. The mixtures were incubated at 37° C. overnight, then plated on 7H10 plates supplemented with hygromycin at 50 μg/ml. Hygromycin resistant colonies were analyzed by PCR and Southern hybridization, as described above, to confirm the deletion of RD1.

Complemetation analyses was performed using the integration proficient cosmids (Pascopella et al., 1994; Lee et al., 1991) pYUB412 made by S. Bardarov, a library made by F. Bange, and cosmid identified and generously provided by S.T. Cole.

Results

Genetic engineering of M. tuberculosis mutants with RD1 deletions. The RD1 (region of difference) region has been defined as the specific 9454 bp of DNA that is present in virulent M. tuberculosis and M. bovis, but absent in BCG (Mahairas et al., 1996). The annotation of RD1 predicts that the deletion would disrupt 9 genes encoding ORF's (Id.; Cole et al., 1998). Five of the 9 ORF's have no known functions (Rv3871, Rv3876, Rv3877, Rv3878 and Rv3879c), two genes encode members of the PE/PPE family (Rv3872/Rv3873), and two genes encode the secreted proteins Cfp10 (Berhet et al., 1998) and Esat6 (Andersen et al., 1991) (Rv3875) (FIG. 1). To test if the RD1 region is essential for virulence in M. tuberculosis, it was necessary to 1) delete the RD1 region from virulent M. tuberculosis strains, 2) demonstrate loss of virulence and 3) restore virulence by complementation with the RD1 DNA. The RD1 deletion (ΔRD1) was successfully introduced into M. tuberculosis by two different techniques, utilizing both a plasmid that allows two-step sequential recombination to make an unmarked deletion, and specialized transduction (FIG. 1a-c). For both methods, the same 1200 bp on each side of the RD1 deletion were cloned into the appropriate plasmid or phage vector and then introduced into M. tuberculosis H37Rv by transformation or phage infection. An unmarked RD1 deletion mutant of M. tuberculosis H37Rv, mc²4004, was constructed, purified, and has the advantage that additional mutations can be readily added to it. In addition, the RD1 deletion was successfully engineered in the H37Rv and Erdman strains of *M. tuberculosis* using a specialized transducing phage. Since TM4 phages have been shown to infect over 500 clinical *M. tuberculosis* isolates (Jacobs et al., 1987), it should be possible to introduce the RD1 deletion into any *M. tuberculosis* isolate of interest.

Figure 2:
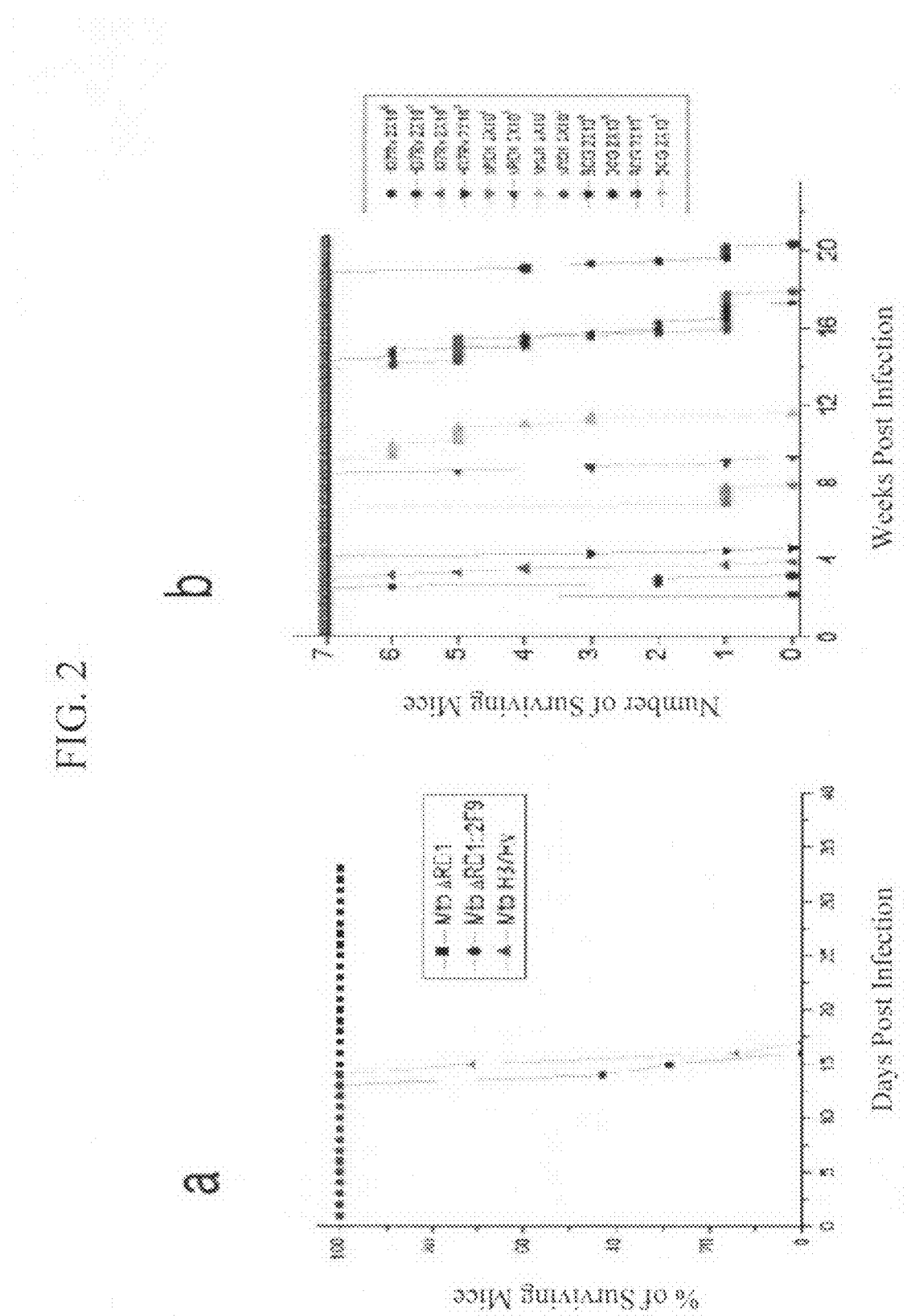
FIG. 2 shows graphs summarizing experiments establishing that *M. tuberculosis* H37Rv ΔRD1 is attenuated in SCID mice. Panel a, Seven female SCID mice were infected intravenously with $2 \times 10^6$ CFU *M. tuberculosis* H37Rv, *M. tuberculosis* H37Rv ΔRD1, and *M. tuberculosis* H37Rv ΔRD1::2F9 per mouse. The number of surviving mice was recorded post infection. Panel b, Mice were infected with different doses of *M. tuberculosis* H37Rv, *M. tuberculosis* H37Rv ΔRD1, and *M. bovis* BCG. For each strain, infection doses of $2 \times 10^6$ CFU, $2 \times 10^5$ CFU, $2 \times 10^4$ CFU, and $2 \times 10^3$ CFU per mouse, were administered via tail intravenous injection.

*M. tuberculosis* H37Rv ΔRD1 is attenuated for virulence. To test if the RD1 deletion causes an attenuating phenotype in *M. tuberculosis*, the *M. tuberculosis* H37Rv ΔRD1 (mc$^2$4004) was introduced into immunocompromised mice possessing the SCID (severe combined immunodeficiency) mutation. Groups of ten mice were injected intravenously with either $2\times10^6$ *M. tuberculosis* H37Rv or *M. tuberculosis* H37Rv ΔRD1 and three mice per group were sacrificed 24 hours later to verify the inoculation doses. All of the SCID mice infected with the parental *M. tuberculosis* H37Rv strain died within 14 to 17 days post infection (FIG. 2a). In contrast, the SCID mice infected with the same dose of *M. tuberculosis* H37Rv ΔRD1 were all alive at 35 days post-infection demonstrating a marked attenuation of the strain. To prove that the attenuation was due to the RD1 deletion, mc$^2$4004 was transformed with an integrating plasmid containing the RD1 region from *M. tuberculosis* H37Rv. SCID mice injected intravenously with $2\times10^6$ of the transformed strain died 13 to 16 days post-infection (FIG. 2a), thereby, establishing that the genes in the RD1 deletion complemented the attenuating phenotype.

To further characterize the attenuating phenotype of the RD1 deletion in mc$^2$4004, we compared the virulence of *M. tuberculosis* H37Rv and BCG-Pasteur to *M. tuberculosis* H37Rv ΔRD1 with time-to-death experiments in SCID mice following injections with 10-fold varying inocula. Groups of 10 mice were injected intravenously, each mouse receiving from $2\times10^3$ to $2\times10^6$ CFU. FIG. 2b shows that the SCID mice succumbed to the infection with all three mycobacterial strains. However, the SCID mice succumbed to an *M. tuberculosis* H37Rv intravenous infection within 2 to 5 weeks, in a dose dependent manner. In the same time frame, the SCID mice did not succumb to infection with *M. tuberculosis* H37Rv ΔRD1 until week 7, and only then, with the high dose of $2\times10^6$ CFU. Mice receiving $2\times10^3$ CFU *M. tuberculosis* H37Rv ΔRD1 survived longer than 14 weeks post infection, the survival rate of which coincided with the mice receiving $2\times10^6$ CFU of *M. bovis* BCG. Thus, these experiments established that *M. tuberculosis* H37Rv ΔRD1 was significantly more attenuated than its parent, but not as attenuated as BCG-Pasteur in the immunocompromised mice.

Figure 3:
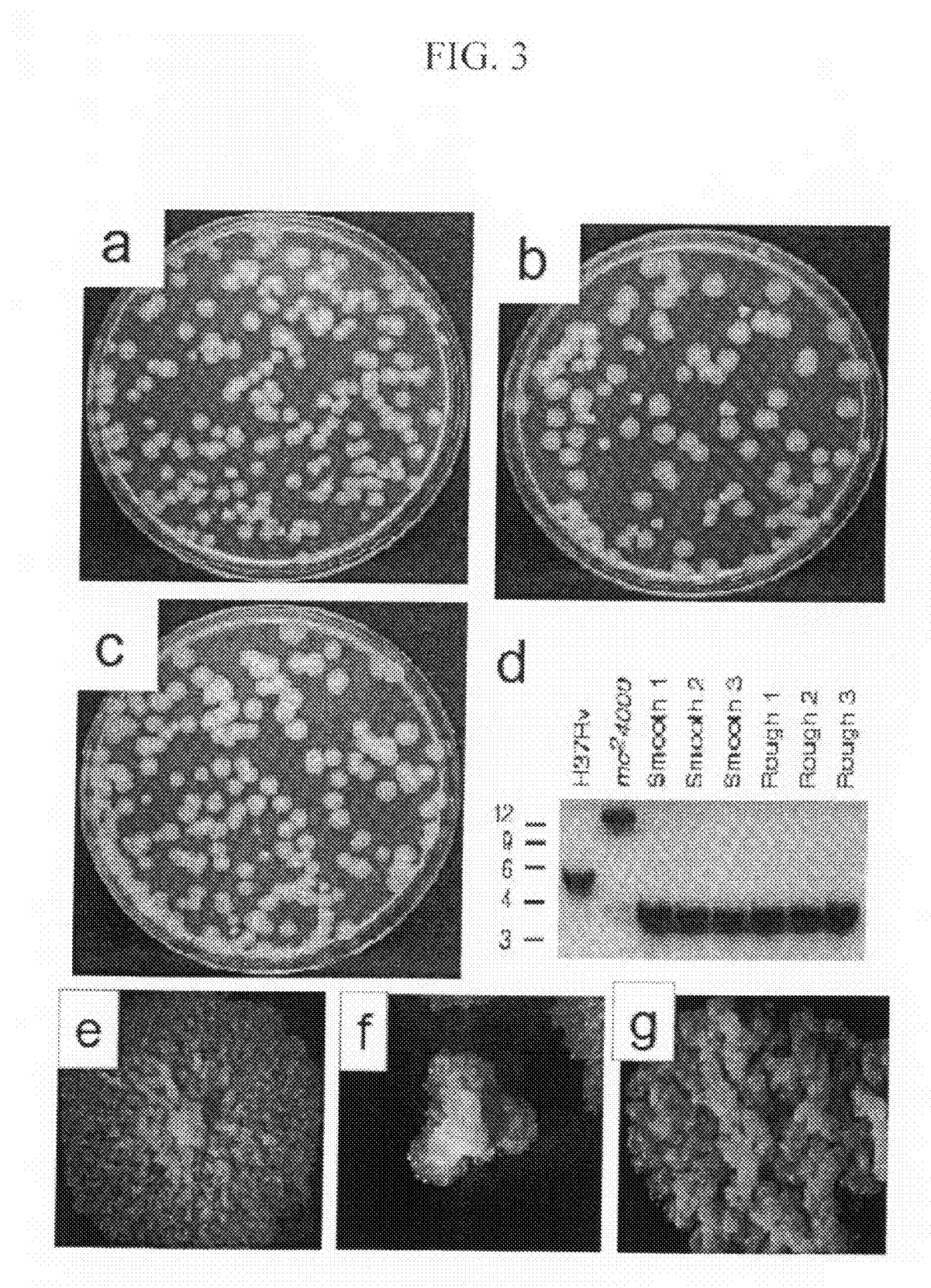
FIG. 3a-3g are photographs, micrographs and autoradiographs showing that the *M. tuberculosis* H37Rv ARD1 mutant exhibits two distinct colonial morphotypes. Panel a, *M. tuberculosis* H37Rv. Panel b, *M. tuberculosis* H37Rv ΔRD1. Panel c, *M. tuberculosis* H37Rv ΔRD1::2F9. Panel d, Southern analysis of *M. tuberculosis* H37Rv ΔRD1 NcoI-digested genomic DNA, isolated from three smooth and three rough colonies and probed with DFS. Panels e-g, Colonial morphotypes at higher magnification. e, Smooth morphotype at week 4. f, Rough morphotype at week 4. g, Rough morphotype at week 6.

Colonial morphotypes of *M. tuberculosis* H37Rv ΔRD1. The *M. tuberculosis* H37Rv ΔRD1 mutant was generated independently three times from the single crossover construct (mc$^2$4000) and upon subculturing, consistently yielded a 20 to 50% mixture of two colonial morphotypes on Middlebrook medium without Tween 80 (FIG. 3a). One morphotype was a smooth (S) phenotype that was flat and corded (like the parental *M. tuberculosis* H37Rv strain) and the second was a rough and raised (R) phenotype. Repeated subculturing of either the R or S colonies continued to yield both colonial morphotypes, but with a distribution of approximately 80% smooth and 20% rough colonies. The distinction of these two types of morphology could be noted even when the colonies were less than two weeks old as the rough colonies were constricted and elevated with only a small portion of the base of the colony attached to the agar, while the smooth colonies tends to be flattened and spread out. When colonies grew older, e.g. 6 weeks old, the rough colonies remained more constricted compared to those of smooth colonies. The rough colonies exhibited large folds on the surface (FIG. 3f, g), as compared to those of the smooth colonies that exhibited small wrinkles (FIG. 3e).

Interestingly, in 1929, Petroff et al. reported a similar property for an early-derived BCG strain (Petroff et al., 1929) and proposed that the attenuation phenotype of BCG was not stable. Calmette disputed that the avirulent phenotype reverted and postulated that Petroff et al. had acquired a contaminating virulent strain. Southern analysis of R and S colonies revealed each morphotype has the same RD1-deleted genotype (FIG. 3d). Furthermore, complementation of *M. tuberculosis* H37Rv ΔRD1 with the RD1 region restored the mutant phenotype back to the homogenous parental S phenotype (FIG. 3a-c). These results suggest that the variable morphotypes resulted directly from the RD1 deletion thus dissociating a direct correlation of virulence with morphotype.

Figure 4:
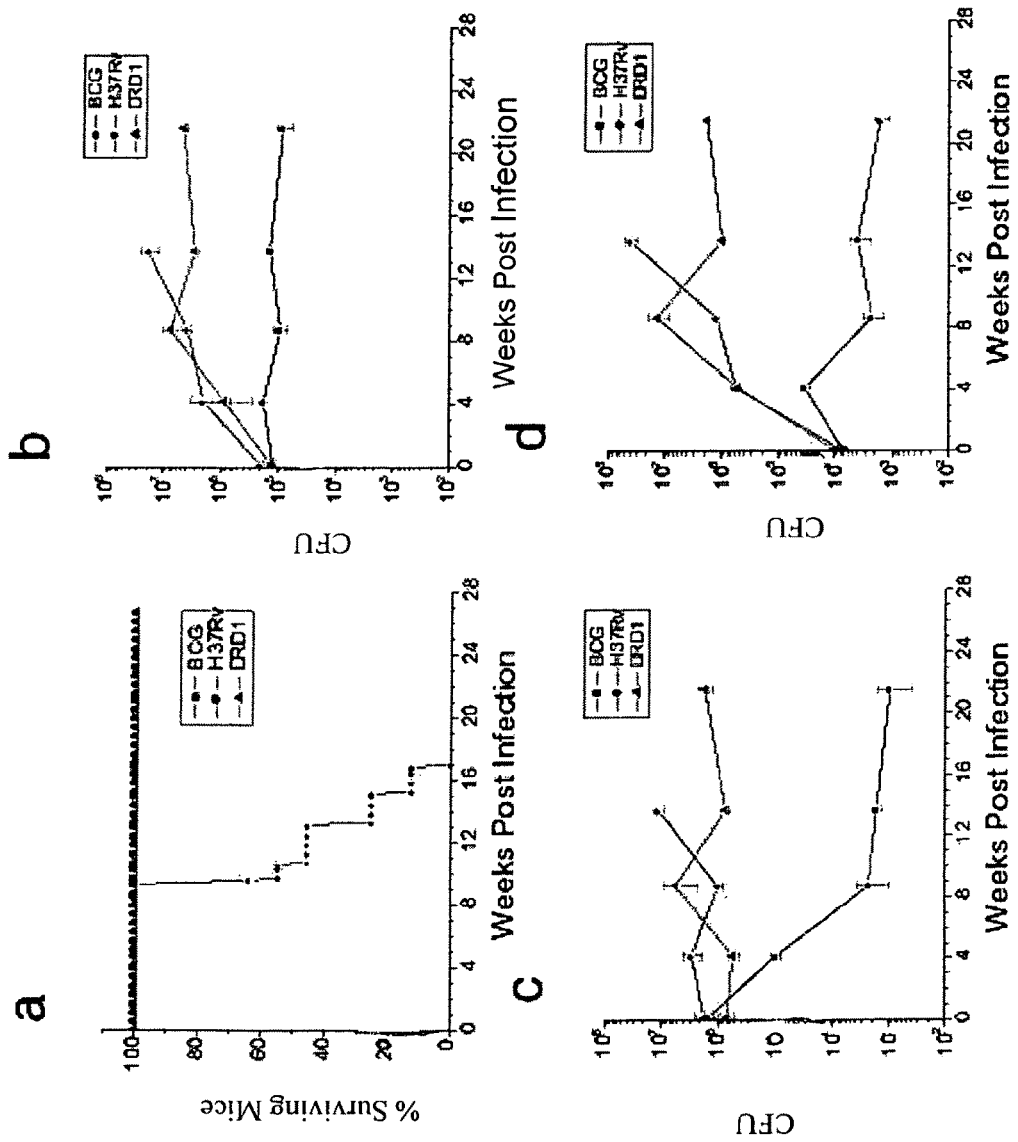
FIG. 4a-4d are graphs showing the growth kinetics of M. tuberculosis H37Rv ΔRD1 in BALB/c mice. Mice were infected with $2 \times 10^6$ CFU through tail injection. Time to death was noted and at day 1, week 4, 8, 14, and 22 post-infection, mice were sacrificed to determine the mycobacterial burden in the spleen, liver, and lung. The numbers represent the means of CFUs in organs derived from three animals. The error bars represent the standard errors of the means. Panel a, Time to death assay in BALB/c mice. Panel b, Spleen. Panel c, Liver. Panel d, Lung.

The *M. tuberculosis* H37Rv ΔRD1 is highly attenuated in immunocompetent BALB/c mice. To further assess the pathogenicity, survival, growth kinetics, and the histopathological analysis of the *M. tuberculosis* H37Rv ΔRD1 mutant, we compared the parental *M. tuberculosis* H37Rv to BCG-Pasteur strains in BALB/c mice. In survival studies, greater than 50% BALB/c mice had died at 14 weeks post i.v. infection with $2\times10^6$ CFUs of *M. tuberculosis* H37Rv strain (FIG. 4a). In contrast, all mice infected with a similar dose of either BCG or *M. tuberculosis* H37Rv ΔRD1 survived for longer than 22 weeks. These results were substantiated in a separate experiment in which a group of 11 BALB/c mice were infected with $1\times10^5$ CFU of *M. tuberculosis* H37RY ΔRD1 and 9 of 11 mice (81%) survived greater than 9 months post-infection (data not shown). While BCG and *M. tuberculosis* H37Rv ΔRD1 showed similar survival results, the growth relative kinetics in mouse organs differed substantially. BCG grew in a limited fashion in lungs, liver and spleen in BALB/c mice and was cleared to undetectable levels by week 12 (FIG. 4b-d). In contrast, the *M. tuberculosis* H37Rv ΔRD1 strain grew in a fashion indistinguishable from the parental *M. tuberculosis* H37Rv in all mouse organs for the first 8 weeks. Thereafter, mice infected with the parental *M. tuberculosis* failed to contain the infection leading to mortality. Strikingly, mice infected with the *M. tuberculosis* H37Rv ΔRD1 showed a definite control over infection resulting in significantly prolonged survival of mice (FIG. 4b-d).

Figure 5:
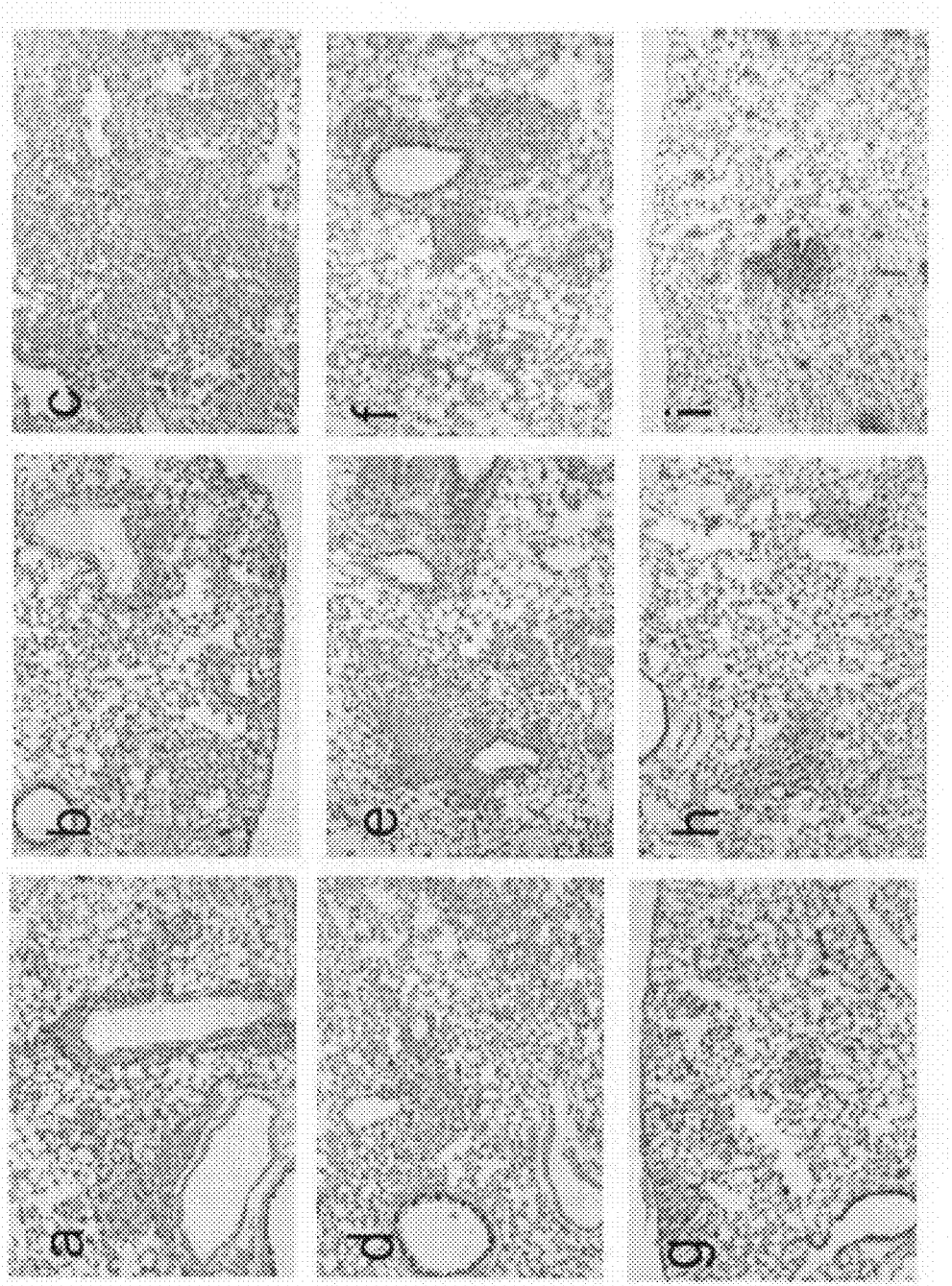
FIG. 5a-5i are micrographs from pathological studies of infected BALB/c mice. Panels a-c, Lungs from mice infected with 2×10$^6$ CFU of M. tuberculosis H37Rv examined at 4, 8 and 14 weeks post-infection. The mild to moderate pneumonia at 4 and 8 weeks (a and b) progressed to severe consolidating granulomatous pneumonia at 14 weeks post infection (c). Panels d-f, Lungs from mice infected with 2×10$^6$ CFU of M. tuberculosis H37Rv ΔRD1 examined at 4, 8 and 22 weeks post-infection showing moderate pneumonia at 8 weeks post-infection (e) and persistent bronchitis and multifocal pneumonitis at 22 weeks post-infection (f). Panels (g)-(i), Mild lung lesions from mice infected with 2×10$^6$ CFU of BCG at 4, 8 and 22 weeks post-infection. Mild focal granulomas scattered widely in the lung at each time point with predominately lymphocytic accumulations in foci at 22 weeks post-infection.

The differing survival data of the three strains was clearly substantiated by histopathological analysis. *M. tuberculosis* H37Rv ΔRD1 caused less severe organ damage in the lung, liver and spleen than the highly virulent parent strain *M. tuberculosis* H37Rv. *M. bovis* BCG was the least virulent of the three strains. Based on histopathological evaluation, the mortality in mice infected with the wild type *M. tuberculosis* H37Rv (documented above and in FIG. 4a) was caused by worsening pneumonia, hepatitis and splenitis (FIG. 5a-c). Mice examined at 14 weeks post-infection had developed severe lobar granulomatous pneumonia. Acid fast staining demonstrated large numbers of *M. tuberculosis* H37Rv, often in clumps, throughout the lung. The livers and spleens showed a severe diffuse granulomatous inflammation.

Histopathological examination further demonstrated that *M. tuberculosis* H37Rv ΔRD1 was attenuated in virulence compared to the parent strain *M. tuberculosis* H37Rv (FIG. 5d-f). In contrast to the rapidly progressive infection with the parent strain *M. tuberculosis* H37Rv, the lung lesions caused by *M. tuberculosis* H37Rv ΔRD1 were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again at 22 weeks post-infection, the lungs showed peribronchial and perivascular inflammatory cell accumulations and focal, generally non-confluent, granulomas now with a prominent lymphocytic infiltration. The numbers of acid fast organisms were reduced. Liver lesions consisted of low numbers of scattered granulomas. Spleens were smaller, with persistent granulomas in the red pulp.

Mice infected with M. bovis BCG showed mild lesions in the lung, liver and spleen at all time points (FIG. 5g-i). At longer time intervals post-infection the lesions were fewer in number, smaller with prominent lymphocytic infiltrations. At 14 weeks post-infection, M. bovis BCG was below the level of detection by acid fast staining. In summary, whereas M. tuberculosis H37Rv ΔRD1 initially grew in a manner similar to the parental M. tuberculosis H37Rv, this RD1 mutant was limited in the extent of spread of infection, particularly in the lung. This contrasted to the extensive and severe damage caused by the parent strain. The subsequent resolving granulomas, localization of the lesions and changes in the composition of the inflammatory cell infiltrations suggested that the mice mounted an effective immune response to combat M. tuberculosis H37Rv ΔRD1 infection and thereby reduced the numbers of viable organisms.

M. tuberculosis H37Rv ΔRD1 protects mice against aerosolized M. tuberculosis challenge. To test the potential of M. tuberculosis H37Rv ΔRD1 to immunize mice and protect against tuberculous challenge, we used the model of subcutaneous immunization followed by aerosol challenge with virulent M. tuberculosis. Our initial studies in C57BL/6 mice monitored the growth the M. tuberculosis H37Rv ΔRD1 strain over an 84-day period. Groups of mice (5 mice per group) were vaccinated subcutaneously (sc) either once or twice, 6 weeks apart, with $10^6$ CFU M. tuberculosis H37Rv ΔRD1 organisms. Additional mice were infected intravenously (iv) with the same dose of the RD1-deleted strain in order to examine the pathogenicity in C57BL/6 mice.

As seen in Table 1, M. tuberculosis H37Rv ΔRD1 persisted in the lungs, liver, and spleen for 3 months at moderate levels of infection but the organisms failed to grow substantially in the lungs and spleens of mice that had been inoculated iv. In contrast, reduced persistence and decreased concentrations of M. tuberculosis H37Rv ΔRD1 organisms were detected in organ homogenates prepared from mice that had been vaccinated sc. For the groups of mice that had been immunized with only one dose sc., low levels of M. tuberculosis H37Rv ΔRD1 bacilli were recovered from the spleen after 28 and 56 days post-vaccination; however, no splenic mycobacteria were detected 84 days after the sc. injection. Importantly, the concentration of M. tuberculosis H37Rv ΔRD1 organisms in the lungs after the sc. immunizations was below the threshold of detection (<100 CFUs per organ) for the CFU assay at nearly all time points during the three month study.

Three months after the sc. vaccinations with the ΔRD1 strain, groups of mice were challenged aerogenically with a low dose (50 CFUs) of an acriflavin-resistant strain of M. tuberculosis Erdman. The use of a drug-resistant challenge strain permitted the differentiation of the challenge organisms from the sensitive vaccine population. As controls, other groups of mice were immunized Sc. with $10^6$ CFUs of BCG Pasteur. The protective responses induced by the M. tuberculosis H37Rv ΔRD1 vaccination were evaluated by assessing the relative growth of the acriflavin-resistant challenge organisms in naïve, BCG vaccinated, and M. tuberculosis H37Rv ΔRD1 immunized mice and by comparing the relative post-challenge lung pathology in the experimental groups and the naive controls. As seen in Table 2, the growth of the drug-resistant challenge organisms was substantially lower in the lungs of animals vaccinated with BCG or the M. tuberculosis H37Rv ΔRD1 vaccine. Significant reductions in the lung CFU values in the vaccinated animals (relative to naive controls) could be detected both 28 and 56 days after the challenge. Dissemination to the spleen was also significantly limited in all of the vaccination groups with the most substantial differences (−1.4 $\log_{10}$ CFUs compared to the naives) being detected during the first month post-challenge. While significant differences in the growth of the mycobacterial challenge was identified between unvaccinated and vaccinated mice, the rate of proliferation of the acriflavin-resistant challenge strain in all the experimental groups (BCG sc or M. tuberculosis H37Rv ΔRD1 1 or 2 doses sc) was nearly identical and not statistically different.

TABLE 2

M. tuberculosis ΔRD1 and BCG protect C57BL/6 mice from areosol challenge with M. tuberculosis Erdman

| | Lung (Log CFU) | | Spleen (Log CFU) | |
|---|---|---|---|---|
| | Day 28 | Day 56 | Day 28 | Day 56 |
| Naive | 4.77 ± 0.06 | 4.11 ± 0.05 | 3.57 ± 0.21 | 3.20 ± 0.16 |
| BCG (1×) | 3.96 ± 0.20 | 3.80 ± 0.08 | 2.18 ± 0.18 | 2.48 ± 0.23 |
| ARD1 (1×) | 3.97 ± 0.39 | 3.71 ± 0.06 | 2.12 ± 0.12 | 2.60 ± 0.25 |
| ARD1 (2×) | 3.96 ± 0.15 | 3.66 ± 0.09 | 2.21 ± 0.15 | 2.22 ± 0.16 |

Immunizations were performed subcutaneously once (1×) or twice (2×) with 2 × $10^6$ CFUs of the vaccinating strains. Three months later, vaccinated animals were aerogenically challenged with 50 CFUs/mouse of acriflavin resistant M. tuberculosis Erdman. The growth of the bacterial challenge was monitored 28 and 56 days post infection by plating on Middlebrook 7H11 plates containing 20 μg/ml acriflavin and using procedures previously described (Delogu et al., 2002).

Discussion

The M. tuberculosis H37Rv ΔRD1 mutant strain shares significant properties with BCG including: 1) a significant attenuation of virulence in mice, 2) the ability to generate variable colonial morphotypes, and 3) the ability to protect mice against aerogenic tuberculosis challenge. These properties, and the observation that RD1 is the only deletion common to all BCG substrains, makes it likely that the RD1

TABLE 1

Growth kinetics in C57BL/6 mice.

| | Lung (Log CFU) | | | Spleen (Log CFU) | | |
|---|---|---|---|---|---|---|
| Weeks | i.v. | s.c. | s.c. (2×) | i.v. | s.c. | s.c. (2×) |
| 4 | 5.86 ± 0.10 | <2 | not done | 5.73 ± 0.05 | 2.41 ± 0.26 | not done |
| 8 | 5.79 ± 0.07 | <2 | 2.52 ± 0.34 | 5.37 ± 0.04 | 3.12 ± 0.40 | 3.62 ± 0.29 |
| 12 | 5.61 ± 0.09 | <2 | <2 | 5.40 ± 0.05 | <2 | 3.52 ± 0.22 |

Mice were infected with $10^6$ M. tuberculosis H73Rv ΔRD1 by different routes. The data are presented as mean ± standard error of the mean.

deletion is the primary attenuating mutation. It remains to be determined if a single gene or a number of genes in this region causes the attenuated phenotype. The variable colonial morphotype switch does suggest that a protein regulating cell wall biogenesis is affected. Notably, defined mutations affecting the cyclopropanation of mycolic acids (Glickman et al., 2000) or the synthesis or export of phthiocerol dimycoseroate (Cox et al., 1999) have been found to correlate with decreased virulence and altered colony morphotypes in *M. tuberculosis* and thus represent attractive candidate genes that might be regulated by an RD1-encoded gene. The *M. tuberculosis* ΔRD1 mutant provides a precisely defined background strain by which to determine virulence and colony morphology related genes.

BCG is currently the only antituberculous vaccine available for use in humans. In many animal models, BCG has been shown to induce protective immunity against *M. tuberculosis* challenge (Opie and Freund, 1937; Hubbard et al., 1992; Baldwin et al., 1998) and in addition, has demonstrated protection against the most severe and fatal form of TB in children (Rodrigues et al., 1991). However, BCG has shown variable efficacy in protecting adults from pulmonary TB (Tuberculosis Prevention Trial, 1980; Hart and Sutherland, 1977; Bloom and Fine, 1994). Due to the uncertain efficacy of BCG, particularly in TB-endemic countries, the development of improved *tuberculosis* vaccines has become an international research priority.

Our challenge studies have demonstrated that the protective immune responses elicited by immunization with *M. tuberculosis* H37Rv ΔRD1 in mice are at least as strong as the protective responses induced by vaccination with BCG. The *M. tuberculosis* H37Rv ΔRD1 mutant also retains the BCG-associated property of limited spread to the lung following subcutaneous immunization. Restricted dissemination of the ΔRD1 mutant to the lung suggests it should have a favorable overall safety profile. Also, the unmarked mutant of *M. tuberculosis* H37Rv ΔRD1 provides a single deletion strain whereby other attenuating mutations can be readily engineered. Since the risk of reversion to wild-type virulence decreases substantially with each additional attenuating mutation, *M. tuberculosis* mutants harboring deletions in two or three separate genetic loci should provide a much safer vaccine for long term use.

*M. tuberculosis* mutants with RD1 deletions represent attractive candidates as novel vaccines for TB prevention. These mutants, derived from a single mutagenic event from the parental *M. tuberculosis* strain, replicate more efficiently in vivo than BCG, especially early in infection. This enhanced rate of proliferation for the RD1-deleted strains, relative to BCG, may lead to the induction of increased protective immunity in humans, after vaccination with *M. tuberculosis* H37Rv ΔRD1. Moreover, they could also be more immunogenic as there exist at least 129 ORFs present in *M. tuberculosis* H37Rv that are absent from *M. bovis* (Behr et al., 1999). Since some of these ORFs are likely to encode regulatory proteins affecting the expression of other genes, there could be hundreds of antigens expressed in *M. tuberculosis*-infected cells that are absent from BCG-infected cells. Thus, RD1 deletion mutants constructed from human tubercle bacilli could protect humans against disease substantially better than BCG.

EXAMPLE 2

Vitamin Auxotrophs of *Mycobacterium Tuberculosis* are Attenuated and Protect Against Tuberculosis This example describes experimental methods and results that establish that deleting genes that control vitamin production in a virulent *M. tuberculosis* causes the *M. tuberculosis* to become avirulent and sustain an infection in mammals, and protect the mammal against challenge with a virulent *M. tuberculosis*.

Given the importance of NAD and nicotinamide (vitamin B3) and pantothenate (vitamin B5) as cofactors involved in carbon utilization, energy transduction (Abiko, 1975; Jackowski, 1996) and the biosynthesis of the complex lipid cell wall of *M. tuberculosis*, we hypothesized that mutations in the biosynthetic pathways for NAD and pantothenate could lead to the generation of mutant strains that retain a limited ability to replicate and subsequently get cleared within the host tissues. In *M. tuberculosis*, the nadABC operon controls the de novo biosynthesis of NAD. Similarly, the panC and panD genes that are organized in an operon control the rate-limiting step in the de novo biosynthesis of pantothenate. We constructed deletion mutants of *M. tuberculosis* in the nadBC and panCD genes using specialized transduction, as described in Example 1. The mutant strains mc$^2$3122 (ΔnadBC) and mc$^2$6001 (ΔpanCD) were auxotrophic for nicotinamide and pantothenate respectively. The in vitro reversion frequencies of the respective mutations were found to be less than $10^{-10}$ events per generation.

Figure 6:
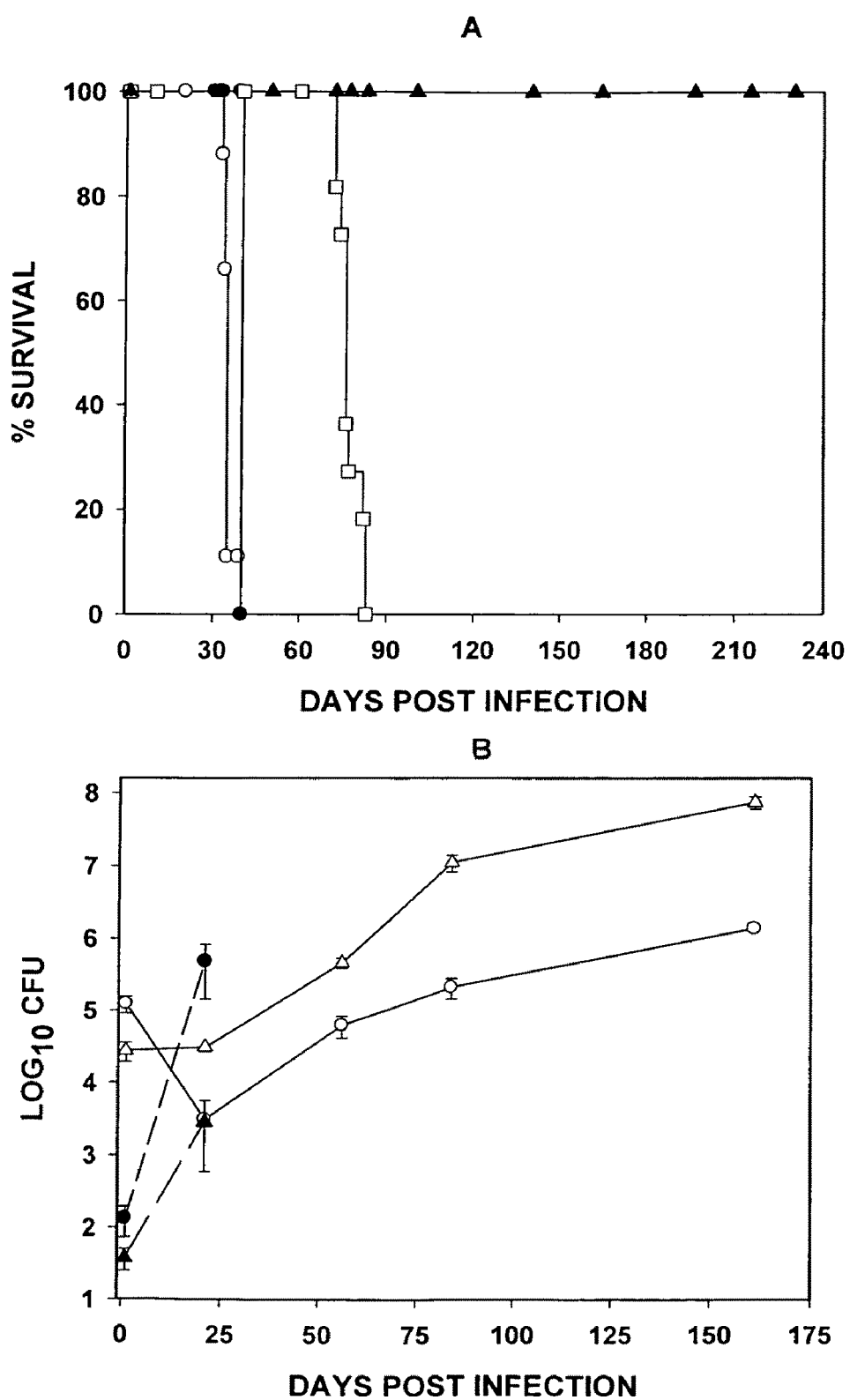
FIG. 6 shows graphs summarizing experiments establishing that pantothenate auxotrophy leads to attenuation of M. tuberculosis Δpan intravenously with 2×10⁶ CFU mycobacteria. Panel A, SCID mice infected with *M. tuberculosis* H37Rv (■), *M. tuberculosis* H37Rv ΔRD1 (□), *M. tuberculosis* Erdman (●), *M. tuberculosis* Erdman ΔRD1 (○), *M. tuberculosis* CDC1551 (▲), *M. tuberculosis* CDC1551 ΔRD1 (Δ), *M. bovis* Ravenel (♦), *M. bovis* Ravenel ΔRD1 (▽); Panel B, SCID mice infected intravenously with *M. tuberculosis* H37Rv (●), *M. tuberculosis* ΔRD1 (■), *M. tuberculosis* ΔRD1::2F9 (▲), *M. bovis* Ravenel (○), *M. bovis* Ravenel ΔRD1 (□), and *M. bovis* BCG (Δ); Panel C, BALB/c mice were infected with *M. tuberculosis* H37Rv (○), *M. tuberculosis* ΔRD1 (Δ), and *M. bovis* BCG (□).

The safety and attenuation of ΔnadBC and ΔpanCD auxotrophic mutants were assessed by infection of immune-compromised SCID mice. SCID mice infected with wild-type *M. tuberculosis* and the ΔnadBC mutant succumbed to infection in about 5 weeks (data not shown). This result clearly indicates that in the absence of T-cell immunity, intermediates of NAD biosynthetic pathway, such as nicotinamide, are readily available in the macrophages to support the growth of the ΔnadBC mutant. In contrast all mice infected with the ΔpanCD mutant survived longer than 30 weeks, demonstrating the severe attenuation of this mutant strain. The full virulence phenotype was restored when the panCD wild type alleles were integrated into the chromosome of the ΔpanCD mutant in single copy, suggesting the observed attenuation in ΔpanCD to be due to the requirement of pantothenate for growth and not due to polar effects of the mutation on downstream genes. SCID mice infected with the same dose of conventional BCG-Pasteur vaccine strain succumbed to infection within 80 days (FIG. 6A) in accordance with earlier reports (Guleria, 1996). Enumeration of bacterial burdens in SCID mice infected with wild type *M. tuberculosis* H37Rv and the complementing strain (panCD in single copy integrated into the chromosome) showed a rapid increase in bacterial numbers in spleen, liver and lung before they succumbed to infection. In contrast, mice infected with ΔpanCD mutant, showed an initial drop in bacterial numbers in spleen and liver followed by a steady increase to reach $10^8$ in the lungs at 160 days, at which time all mice were still alive (FIG. 6B).

Figure 7:
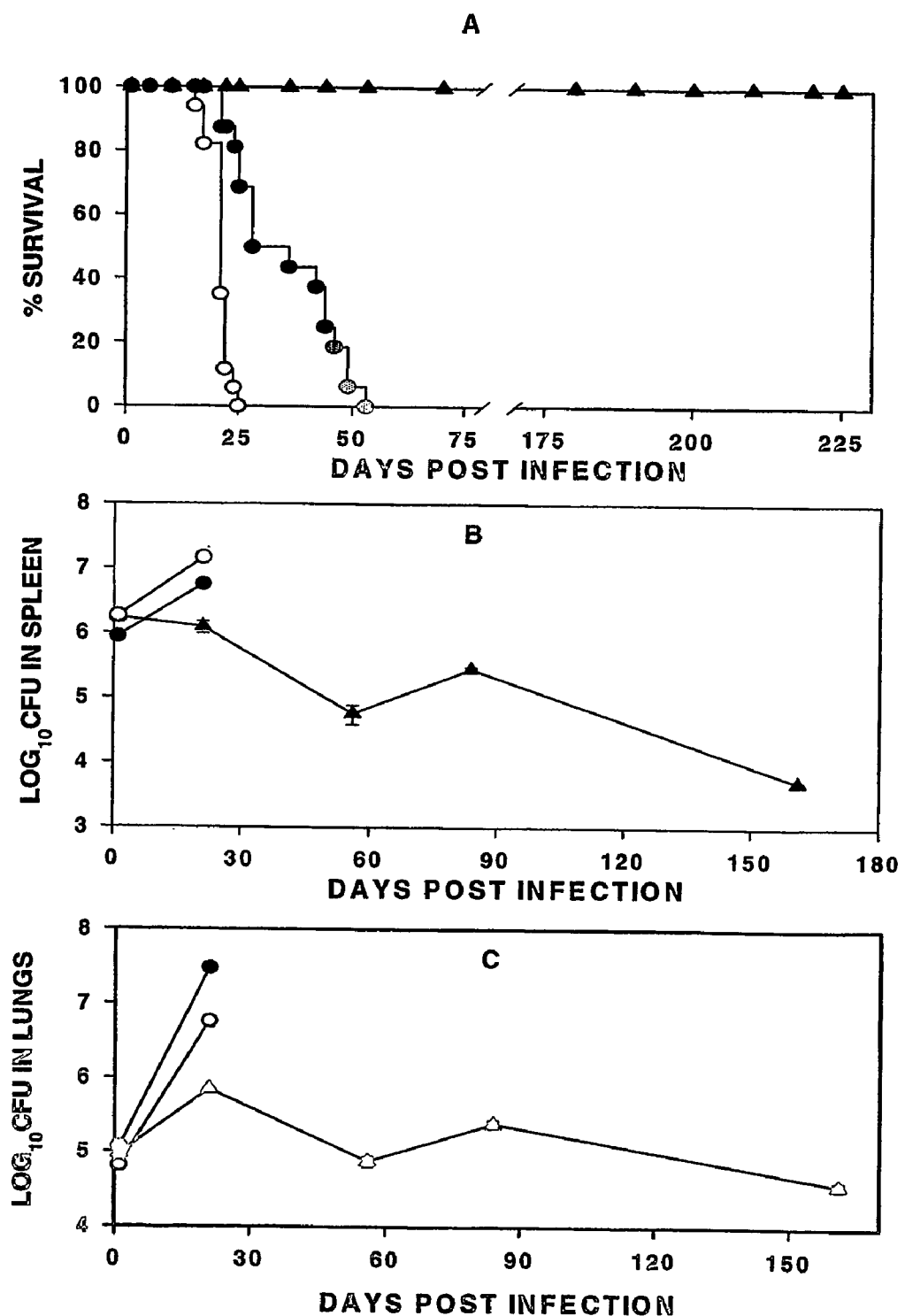

Having demonstrated the significant attenuation of ΔpanCD mutant, we sought to address the in vivo growth characteristics of this mutant in immune-competent BALB/c mice. All BALB/c mice infected with H37Rv succumbed to infection by day 25 with a MST of 22 days. Similarly, mice infected with the panCD-complemented strain were highly virulent with 100% mortality between 3-8 weeks post-infection similar to the wild type strain, with a MST of 28 days. In contrast, all mice infected with ΔpanCD mutant survived for over 33 weeks demonstrating the severe attenuation phenotype of this mutant in immune-competent mice (FIG. 7A). Interestingly, bacterial enumeration at three weeks post infection showed 1 log increase in the ΔpanCD numbers in lungs followed by a state of persistence with the onset of adaptive immune response. This growth characteristic was observed only in the lung but not in spleen or liver (FIG. 7B,C). A desirable trait of an effective live attenuated vaccine strain is its ability to grow within the host in a limited fashion in order to produce in vivo all the important protective antigens (McKenney, 1999; McKenny, 2000; Kanai, 1955). The ΔpanCD mutant exhibits this characteristic in the lung, which is the primary site of infection in humans and does not get cleared over a prolonged period in all the three organs. The earlier auxotrophs of M. tuberculosis failed to grow in any of the organs and hence failed to adequately protect against experimental challenge in guinea pigs (Jackson, 1999), or mice.

The ability of the ΔpanCD mutant to exhibit limited growth in the lung until the onset of adaptive immune response suggests that an unidentified putative pantothenate permease is able to transport this nutrient into resting macrophages, as in the SCID mice. A sodium-dependent pantothenate permease actively transports pantothenate into the cell of *Escherichia coli* (Vallari and Rock, 1985; Jackowski and Alix, 1990), *Plasmodium falciparum* (Saliba and Kirk, 2001) and mammals. Subsequent activation of macrophages leads to restricted supply of this nutrient within the phagosome resulting in growth arrest of the mutant. Pantothenic acid or its derivatives have been reported to confer resistance to radiation and oxidative stress by virtue of their role in biosynthesis of CoA and also by indirectly increasing the cellular supply of glutamate, a precursor of glutathione (Slyshenkov, 1995). Pantothenate kinase (PanK) mutants of *Drosophila* display membrane defects and improper mitosis and meiosis due to decreased phospholipid biosynthesis (Afshar et al., 2001). The disruption of de novo pantothenate biosynthesis causes an increased susceptibility of the ΔpanCD mutant to reactive oxygen and nitrogen intermediates that are released within activated macrophages.

Figure 8:
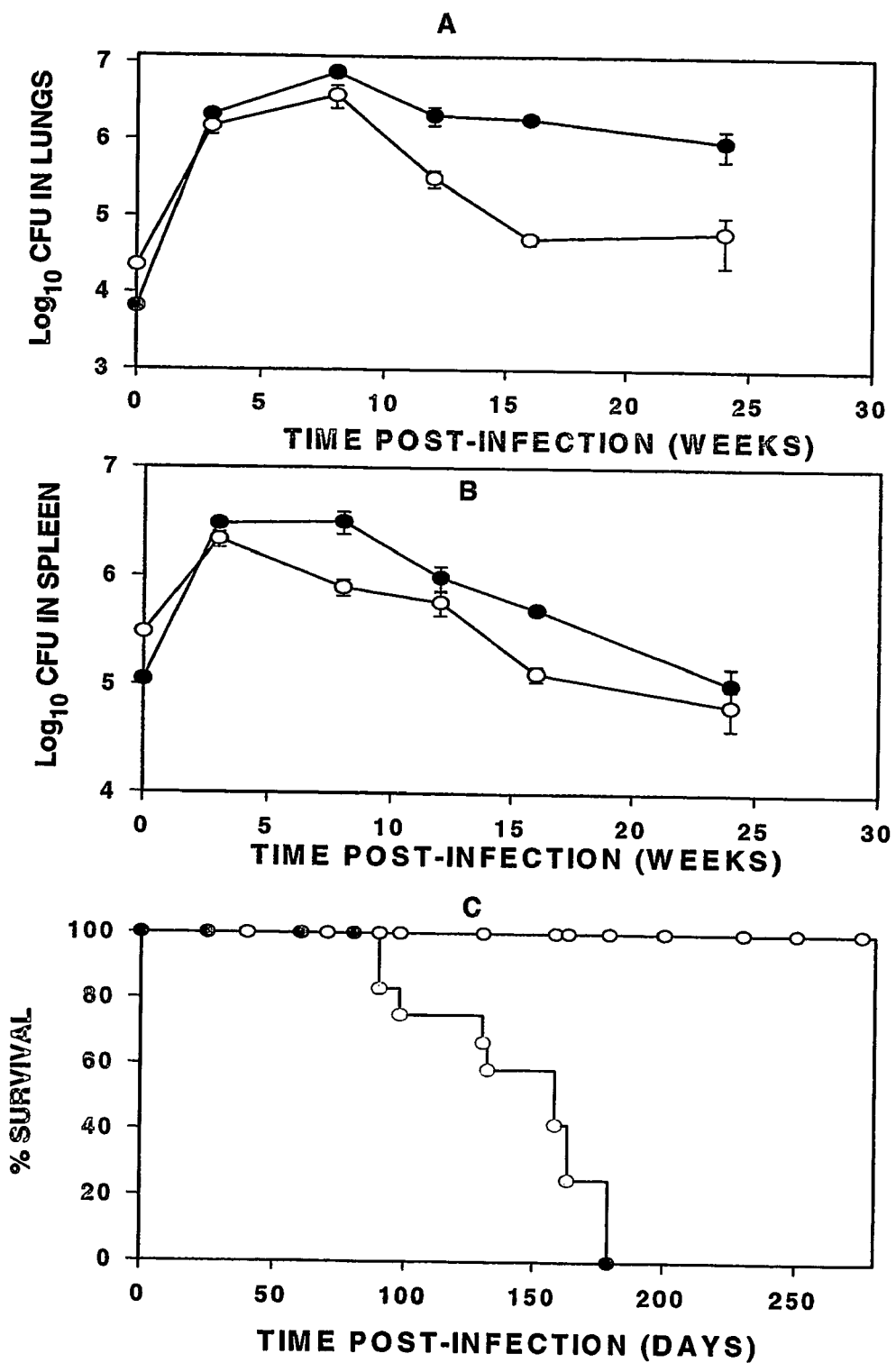
Figure 9:
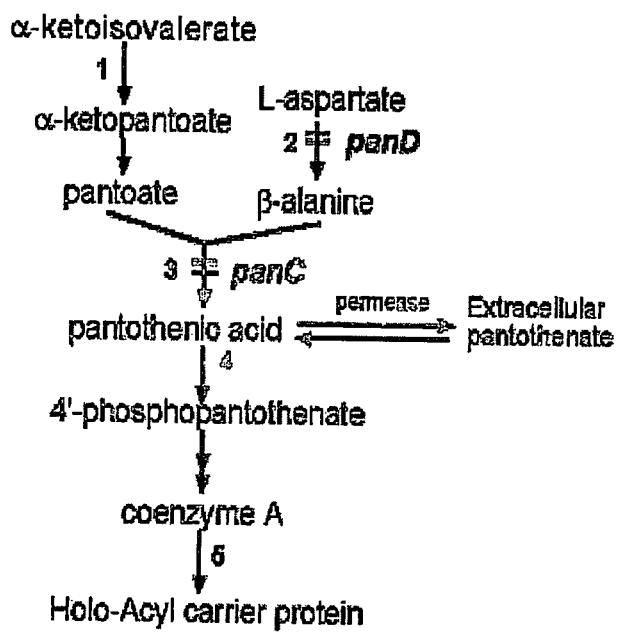
Figure 9:
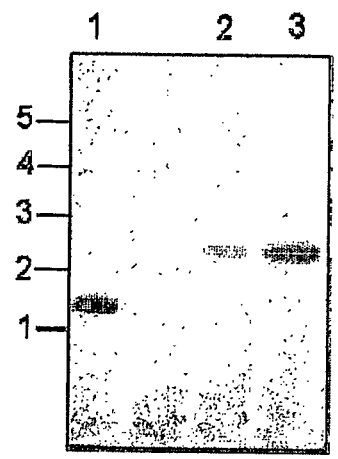
Figure 9:
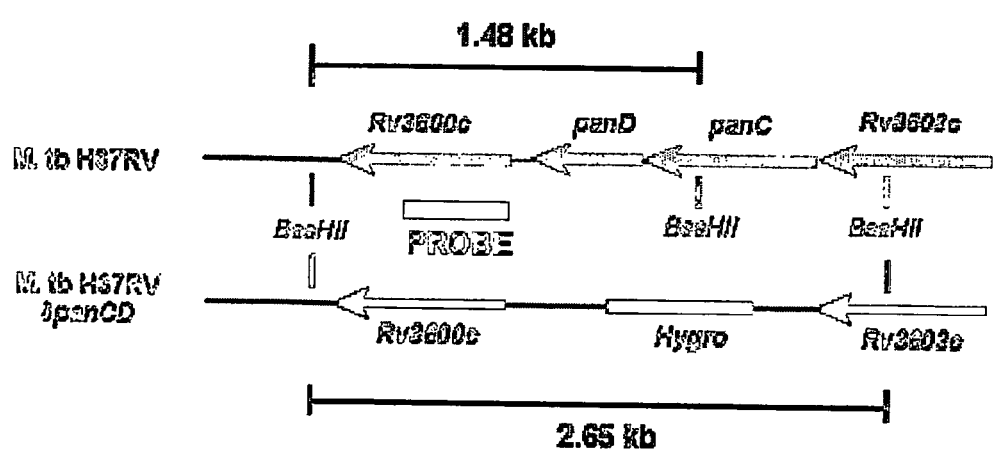

Having observed the ΔnadBC mutant to be non-attenuated in SCID mice, we chose to study the in vivo growth kinetics of this mutant in the more resistant C57BL/6 mice background. During the first three weeks of infection, the number of wild type and mutant bacteria recovered from all three organs showed little or no difference. Their numbers gradually increased in the lungs to reach $10^6$. However, with the onset of adaptive immune response at three weeks, when the growth of bacteria in the lungs of mice infected with H37Rv became constant and tightly controlled, bacterial load in the lungs of mice infected with ΔnadBC mutant showed a constant tendency for clearance to reach more than 1.5 log drop in the bacterial numbers compared to mice infected with wild type strain (FIG. 8A). This difference was preserved up to 24 weeks following infection.

The reduced ability of the ΔnadBC mutant to sustain an infection was accompanied by attenuated virulence clearly seen from the survival experiment (FIG. 8C). While all mice infected with the wild type strain succumbed to infection between day 90 and 179 (MST 116 days) all mice infected with the ΔnadBC mutant (n=12) remain alive for a period of more than 8 months (FIG. 8C).

Our observation of the attenuation phenotype of ΔnadBC mutant became obvious only after the onset of immune response, suggesting that once the macrophages become activated, they restrict the amount of available NAD or NAD intermediates causing a restricted growth of the mutant strain. This would be in agreement with the recently reported observations that a significant part of antimicrobial function of the macrophages could be attributed to the IFN-γ promoted enhanced expression of indolamine 2-oxygenase (IDO), the inducible enzyme controlling L-tryptophan catabolic pathway causing an almost complete depletion of L-tryptophan pool. The enhanced catabolism of L-tryptophan leads to increased de novo biosynthesis of NAD needed to protect the cells from the free radicals formed as a result of macrophage activation. Recently, several studies have demonstrated the involvement of the tryptophan catabolism in the antimicrobial mechanisms of the activated macrophages. Induction of IDO was found responsible for the inhibition of intracellular growth of *Toxoplasma, Leishmania, Legionella* and *Chlamydia*. The restricted intracellular growth of ΔnadBC mutant could be explained with the very little amount of free NAD or NAD intermediates available within the activated macrophages.

Having established the safety and persistence of ΔpanCD and ΔnadBC in immunocompetent mice, the protective efficacy of these mutants were evaluated using an aerosol challenge model with virulent *M. tuberculosis*, using the methods described in Example 1. The aerosol route of infection was chosen, as this is the natural route of infection in humans. To assess the capacity of the auxotrophic vaccines to restrict growth of virulent *M. tuberculosis* in the organs of infected mice, bacterial numbers were enumerated one month post-infection in lung and spleen. See Table 3. In the unimmunized controls, bacterial numbers rose rapidly in the spleen and lungs, in contrast mice infected with a single dose of ΔpanCD displayed significant reduction in bacterial numbers in the spleen and lung ($p<0.05$, in comparison to unimmunized controls). Mice given two doses of ΔpanCD displayed a statistically significant reduction in the bacterial numbers to 4.5 log units in the lung ($p<0.01$) and 3.7 log units in the spleen ($p<0.05$). Mice vaccinated with BCG showed comparable reduction in bacterial burden in the lung and spleen to 3.3 log units and 4.7 log units respectively ($p<0.01$). Mice immunized with one or two doses of ΔnadBC mutant conferred statistically significant protection ($p<0.01$ in comparison to unimmunized group) that is comparable to the protection afforded by BCG vaccination. Interestingly, mice immunized with the ΔnadBC mutant showed no detectable CFUs in the spleen suggesting that the vaccination completely prevented the hematogenous spread of wild type *M. tuberculosis* following aerosol challenge.

TABLE 3

Table 3. The attenuated *M. tuberculosis* ΔnadBC and ΔpanCD mutants protect against aerogenic challenge with *M. tuberculosis* Erdman. Groups of C57BL/6 mice (5 mice per group) were vaccinated subcutaneously either once or twice (6 weeks apart) with $10^6$ CFUs of mutant strains. Control mice were vaccinated subcutaneously with $10^6$ CFUs of BCG-Pasteur. Three months after the initial immunization with either ΔnadBC or ΔpanCD mutant or BCG, the mice were aerogenically challenged with approximately 100 CFUs of acriflavin-resistant *M. tuberculosis* Erdman (Ac$^r$MTB) strain as described earlier (Collins, 1985) After 28 days, the challenged mice were sacrificed, and the lungs and spleens of individual mice were removed aseptically and homogenized separately in 5 ml of Tween 80-saline using a Seward stomacher 80 blender (Tekmar, Cincinnati, OH). The homogenates were diluted serially in Tween 80 saline and plated on Middlebrook 7H11 agar with or without appropriate supplements as required. Samples from the BCG-vaccinated controls were plated on 7H11 agar containing 2 mg of thiophenecarboxylic acid hydrazide (Sigma Chemical Co., St Louis, MO) per ml to inhibit growth of any residual BCG. The CFU results were evaluated using the one-way ANOVA analysis of the GraphPad InStat program. The numbers in paranthesis represent the differences between naïve and vaccinated organ CFUs.

| Experimental Group | Lung CFUs ($\log_{10}$) | Spleen CFUs ($\log_{10}$) |
|---|---|---|
| | A | |
| Naive | 4.05 ± 0.21 | 3.94 ± 0.21 |
| ΔnadBC (1 × sc) | 3.37 ± 0.40 ** | <2 ** |
| ΔnadBC (2 × sc) | 3.6 ± 0.35 ** | <2 ** |
| BCG (1 × sc) | 3.46 ± 0.19 ** | <2 ** |

TABLE 3-continued

Table 3. The attenuated *M. tuberculosis* ΔnadBC and ΔpanCD mutants protect against aerogenic challenge with *M. tuberculosis* Erdman. Groups of C57BL/6 mice (5 mice per group) were vaccinated subcutaneously either once or twice (6 weeks apart) with $10^6$ CFUs of mutant strains. Control mice were vaccinated subcutaneously with $10^6$ CFUs of BCG-Pasteur. Three months after the initial immunization with either ΔnadBC or ΔpanCD mutant or BCG, the mice were aerogenically challenged with approximately 100 CFUs of acriflavin-resistant *M. tuberculosis* Erdman (Ac'MTB) strain as described earlier (Collins, 1985) After 28 days, the challenged mice were sacrificed, and the lungs and spleens of individual mice were removed aseptically and homogenized separately in 5 ml of Tween 80-saline using a Seward stomacher 80 blender (Tekmar, Cincinnati, OH). The homogenates were diluted serially in Tween 80 saline and plated on Middlebrook 7H11 agar with or without appropriate supplements as required. Samples from the BCG-vaccinated controls were plated on 7H11 agar containing 2 mg of thiophenecarboxylic acid hydrazide (Sigma Chemical Co., St Louis, MO) per ml to inhibit growth of any residual BCG. The CFU results were evaluated using the one-way ANOVA analysis of the GraphPad InStat program. The numbers in paranthesis represent the differences between naïve and vaccinated organ CFUs.

| Experimental Group | Lung CFUs ($\log_{10}$) | Spleen CFUs ($\log_{10}$) |
|---|---|---|
| B |  |  |
| Naive | 5.56 ± 0.05 | 4.35 ± 0.21 |
| ΔpanCD (1 × sc) | 4.99 ± 0.17 (−0.57) * | 3.65 ± 0.15 (−0.70) * |
| ΔpanCD (2 × sc) | 4.55 ± 0.09 (−1.01) ** | 3.73 ± 0.21 (−0.62) * |
| BCG (1 × sc) | 4.71 ± 0.21 (−0.85)  | 3.35 ± 0.20 (−1.00)  | p < 0.05 compared to naïve,
** p < 0.01 compared to naïve

Table 3. The attenuated *M. tuberculosis* ΔnadBC and ΔpanCD mutants protect against aerogenic challenge with *M. tuberculosis* Erdman. Groups of C57BL/6 mice (5 mice per group) were vaccinated subcutaneously either once or twice (6 weeks apart) with $10^6$ CFUs of mutant strains. Control mice were vaccinated subcutaneously with $10^6$ CFUs of BCG-Pasteur. Three months after the initial immunization with either ΔnadBC or ΔpanCD mutant or BCG, the mice were aerogenically challenged with approximately 100 CFUs of acriflavin-resistant *M. tuberculosis* Erdman (Ac'MTB) strain as described earlier (Collins, 1985) After 28 days, the challenged mice were sacrificed, and the lungs and spleens of individual mice were removed aseptically and homogenized separately in 5 ml of Tween 80-saline using a Seward stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg of thiophenecarboxylic acid hydrazide (Sigma Chemical Co., St Louis, Mo.) per ml to inhibit growth of any residual BCG. The CFU results were evaluated using the one-way ANOVA analysis of the Graph Pad InStat program. The numbers in parenthesis represent the differences between naïve and vaccinated organ CFUs.

In order to test the ability of the auxotrophic mutants to confer long lasting immunity, mice were challenged 7 months after an initial subcutaneous immunization with the ΔnadBC mutant. See Table 4. Mice immunized with ΔnadBC displayed significantly reduced numbers of the challenge organism in the lungs and no detectable numbers in the spleen comparable to the numbers seen in the BCG vaccinated mice. The results suggest that the ΔnadBC vaccine strain is able to persist within the mouse organs sufficiently long to mount a long lasting immunity to control subsequent infection.

TABLE 4

Table 4. Immunizations with the ΔnadBC mutant confer long-term protection against an aerosol challenge. Groups of C57BL/6 mice (5 mice per group) were vaccinated subcutaneously or intravenously either once or twice (6 weeks apart) with $10^6$ CFUs of ΔnadBC mutant. Control mice were vaccinated subcutaneously with $10^6$ CFUs of BCG-Pasteur. Seven months after the initial immunization with either ΔnadBC mutant or BCG, the mice were aerogenically challenged with approximately 50 CFUs of acriflavin-resistant *M. tuberculosis* Erdman (Ac'MTB) strain and the bacterial numbers at 28 days post challenge enumerated as described in Table 1.

| Experimental Group | Lung CFUs ($\log_{10}$) | Spleen CFUs ($\log_{10}$) |
|---|---|---|
| Naive | 4.61 ± 0.07 | 4.07 ± 0.20 |
| BCG | 4.00 ± 0.13* | 2 |
| NAD (1 × iv) | 3.28 ± 0.15** | <2 |
| NAD (2 × iv) | 2.95 ± 0.14** | <2 |
| NAD (1 × sc) | 4.05 ± 0.12* | <2 |
| NAD (2 × sc) | 3.94 ± 0.13* | <2 |

*P < 0.05;
**P < 0.01 by Dunnett's Multiple Comparison Test

To the best of our knowledge this is the first report of any *M. tuberculosis* auxotrophic vaccines administered subcutaneously to confer protection comparable to the conventional BCG vaccine strain in a mouse model of infection. Mice vaccinated with the ΔpanCD and ΔnadBC survived for over one year following the aerosol challenge indicating the protection and safety of these vaccine strains.

EXAMPLE 3

A Pantothenate Auxotroph of *Mycobacterium tuberculosis* is Highly Attenuated and Protects Mice Against Tuberculosis This Example is published as Sambandamurthy et al., 2002.

Example Summary

With the advent of HIV and the widespread emergence of drug resistant strains of *Mycobacterium tuberculosis*, newer control strategies in the form of a better vaccine could decrease the global incidence of *tuberculosis*. A desirable trait in an effective live attenuated vaccine strain is its ability to persist within the host in a limited fashion in order to produce important protective antigens in vivo (Kanai and Yanagisawa, 1955; McKenney et al., 1999). Rationally attenuated *M. tuberculosis* vaccine candidates have been constructed by deleting genes required for growth in mice (Jackson et al., 1999; Hondalus et al., 2000; Smith et al., 2001). These candidate vaccines failed to elicit adequate protective immunity in animal models, due to their inability to persist sufficiently long within the host tissues. Here we report that an auxotrophic mutant of *M. tuberculosis* defective in the de novo biosynthesis of pantothenic acid (vitamin B5) is highly attenuated in immunocompromised SCID mice and in immunocompetent BALB/c mice. SCID mice infected with the pantothenate auxotroph survived significantly longer than mice infected with either BCG vaccine or virulent *M. tuberculosis* (250 days, vs. 77 days, vs. 35 days). Subcutaneous immunization with this auxotroph conferred protection in C57BL/6J mice against an aerosol challenge with virulent *M. tuberculosis*, which was comparable to that afforded by BCG vaccination. Our findings highlight the importance of de novo pantothenate biosynthesis in limiting the intracellular survival and pathogenesis of *M. tuberculosis* without reducing its immunogenicity in vaccinated mice.

Materials and Methods.

Media and Strains. *M. tuberculosis* H37Rv, *M. tuberculosis* Erdman and *M. bovis* BCG Pasteur were obtained from the Trudeau Culture Collection (Saranac Lake, N.Y.) and cultured in Middlebrook 7H9 broth and 7H11 agar supplemented with 10% OADC, 0.5% glycerol, and 0.05% Tween 80. When required, pantothenate (24 μg/ml), hygromycin (50 μg/ml) or kanamycin (25 μg/ml) was added. Stock strains were grown in Middlebrook 7H9 broth in roller bottles and harvested in mid-logarithmic growth phase, before being stored in 1 ml vials at −70° C. until required.

Figure 10:
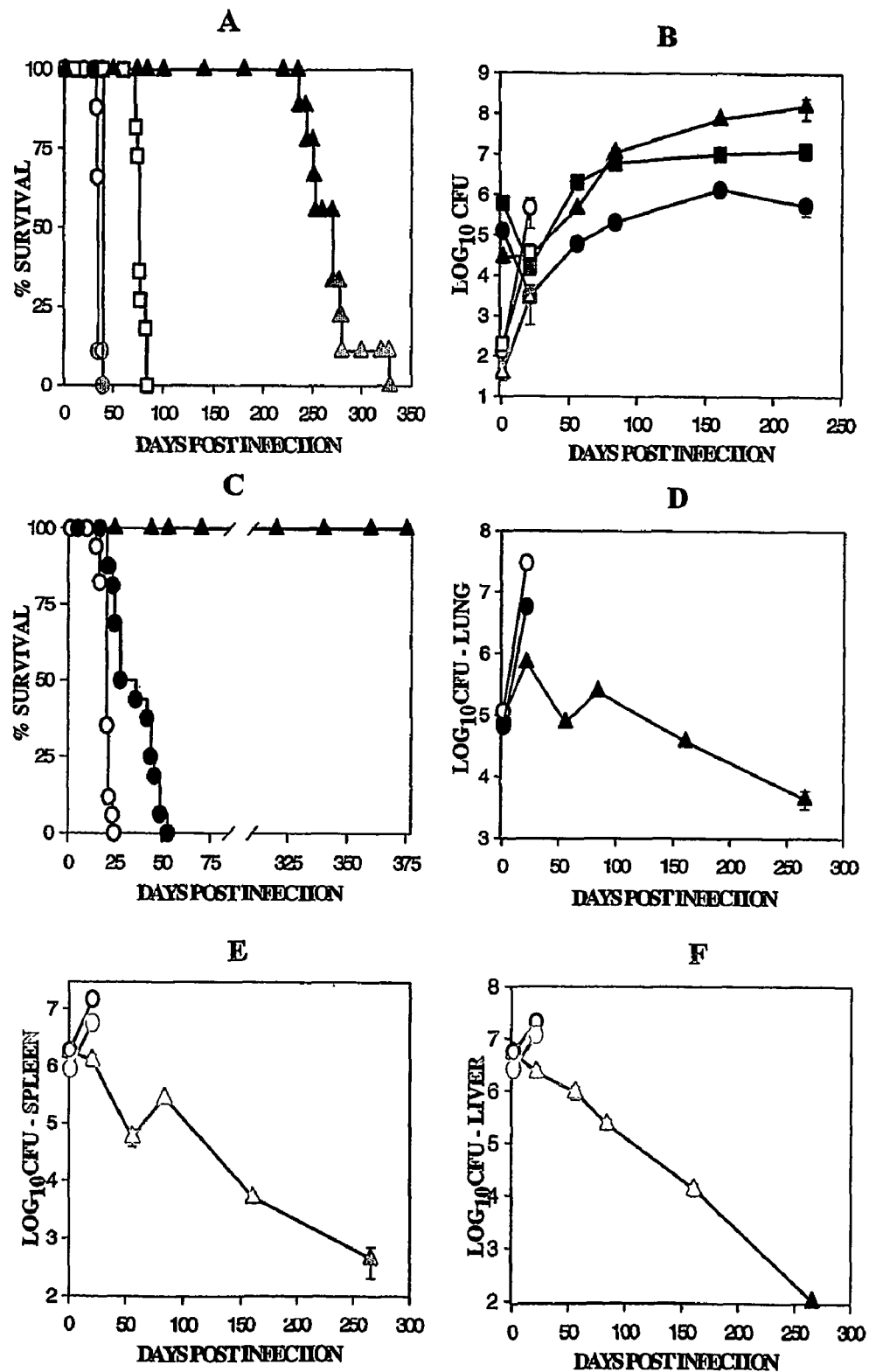
Figure 11:
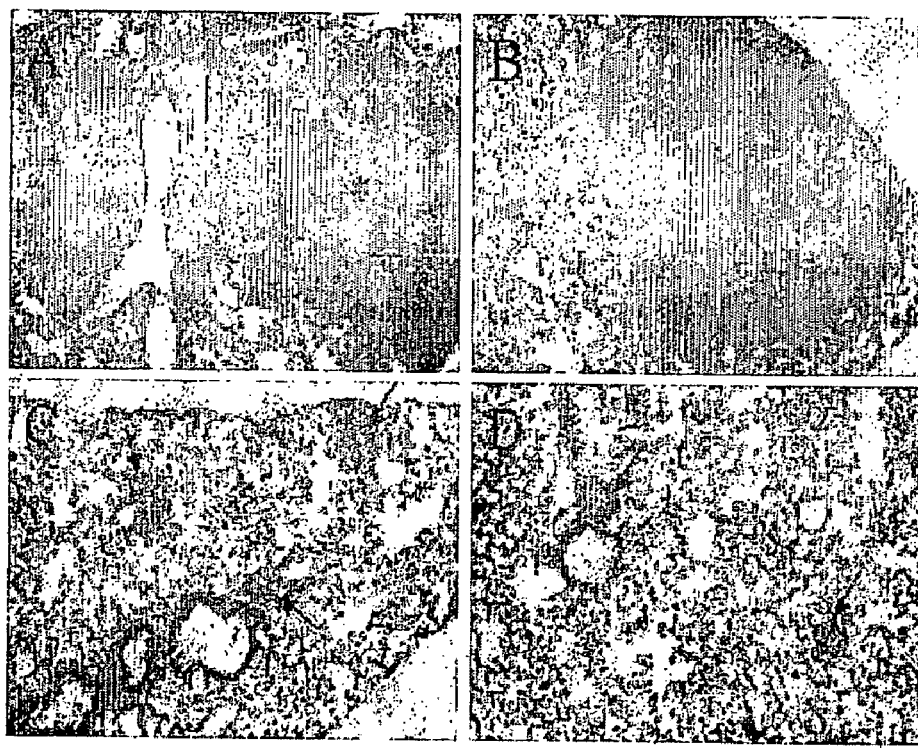
Figure 11:
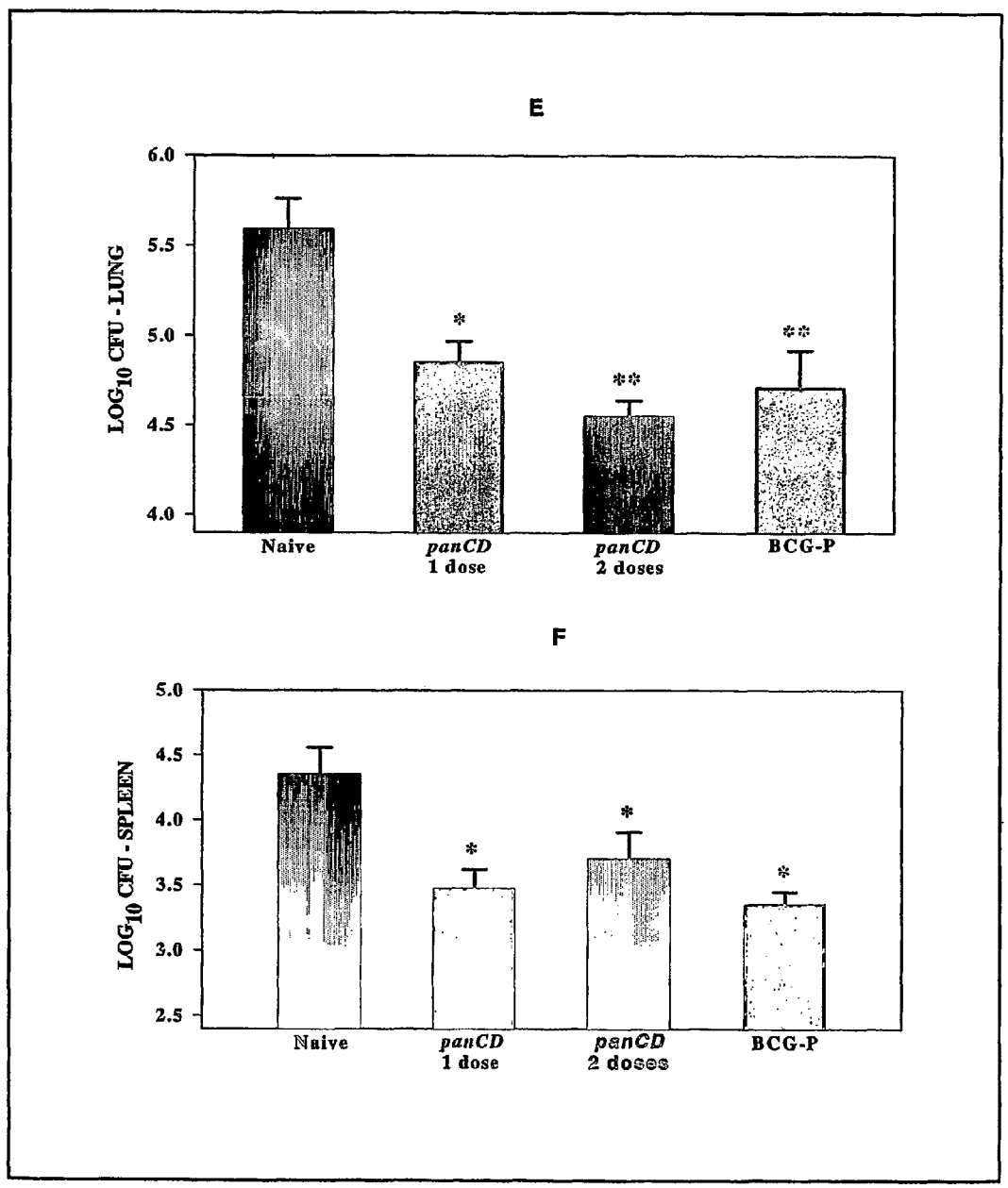

Disruption of panCD genes in *M. tuberculosis*. Specialized transduction was employed to disrupt the chromosomal copy of the panCD genes as described (U.S. Pat. No. 6,271,034). Briefly, the 823 bp region upstream to the panC gene was amplified using primers Pan1 (5'-GTGCAGCGCCATCTCTCA-3')(SEQ ID NO:9) and Pan2 (5'-GTTCACCGGGATGGAACG-3')(SEQ ID NO:10). A 716 bp region downstream to the panD gene was amplified using primers Pan3 (5'-CCCGGCTCGGTGTGGGAT-3')(SEQ ID NO:11) and Pan4 (5'-GCGCGGTATGCCCGGTAG-3')(SEQ ID NO:12). PCR products were cloned with the TOPO TA cloning kit (Invitrogen, CA), and sequenced. PCR products were subsequently cloned into pJSC347, flanking a hygromycin cassette to create pSKV1. PacI digested pSKV1 was ligated into the temperature-sensitive mycobacteriophage phAE159 derived from TM4 and transduced as described earlier (Glickman et al., 2000; Raman et al., 2001). Genomic DNAs from hygromycin-resistant and pantothenate-requiring colonies were digested with BssHII, and probed with a 716 bp downstream region, flanking the *M. tuberculosis* panCD operon to confirm the deletion. For complementation, the *M. tuberculosis* pan CD operon was amplified by PCR from genomic DNA with its putative promoter, cloned with TA cloning kit, sequenced, and subcloned into pMV306kan, a site-specific integrating mycobacterial vector.

Animal infections. C57BL/6, BALB/cJ and BALB/c SCID mice (6-8 weeks old) were purchased from Jackson Laboratories and were infected intravenously through the lateral tail vein. For time-to-death assays, BALB/c SCID mice were infected intravenously with $1\times10^2$ CFU of *M. tuberculosis* H37Rv, $1\times10^2$ CFU of panCD-complemented strain, $1\times10^5$ CFU of ΔpanCD mutant, or $1\times10^5$ CFU of *M. bovis* BCG-P. For mouse organ CFU assays, BALB/cJ mice were infected with $1\times10^6$ CFU of *M. tuberculosis* H37Rv or the panCD-complemented strain or the ΔpanCD mutant. At appropriate time points, groups of 4-5 mice were sacrificed and the selected organs were homogenized separately in PBS/0.05% Tween 80, and colonies were enumerated on 7H11 plates grown at 37° C. for 3-4 weeks (see McKinney et al., 2000). Pathological examination was performed on tissues fixed in 10% buffered formalin. The CFU results were evaluated using the one-way ANOVA analysis of the Graph Pad InStat program. All animals were maintained in accordance with protocols approved by the Albert Einstein College of Medicine Institutional Animal Care and Use Committee.

Vaccination Studies. Groups of C57BL/6 mice (5 mice per group) were vaccinated subcutaneously either once or twice (6 weeks apart) with $1\times10^6$ CFU of the ΔpanCD mutant strain. Control mice were vaccinated subcutaneously with $1\times10^6$ CFU of *M. bovis* BCG-P. Three months after the initial immunization with either the ΔpanCD mutant or BCG, the mice were aerogenically challenged with approximately 50-100 CFU of *M. tuberculosis* Erdman strain as described earlier. At 28 days following aerosol challenge, the challenged mice were sacrificed; the lungs and spleens of individual mice were removed aseptically and homogenized separately in 5 ml of Tween 80-saline using a Seward Stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg/ml of thiophene-2-carboxylic acid hydrazide (Sigma) to inhibit growth of any residual BCG. Results and Discussion.

Lipid biosynthesis and metabolism have been shown to play a pivotal role in the intracellular replication and persistence of *M. tuberculosis* (Cox et al., 1999; Camacho et al., 1999; Glickman et al., 2000; De Voss et al., 2000; Manca et al., 2001; McKinney et al., 2000). Therefore, we sought to globally impair the ability of this bacterium to synthesize lipids. Pantothenic acid (vitamin B 5) is an essential molecule required for the synthesis of coenzyme A (CoA) and acyl carrier protein (ACP), that play important roles as acyl group carriers in fatty acid metabolism, the tricarboxylic acid cycle, biosynthesis of polyketides and several other reactions associated with intermediary metabolism (Jackowski, 1996). Bacteria, plants and fungi synthesize pantothenate from amino acid intermediates, whereas it is a nutritional requirement in higher animals (FIG. 9*a*).

We constructed a double deletion mutant of *M. tuberculosis* in the panC and panD genes that are involved in the de novo biosynthesis of pantothenate (FIG. 9*b,c*). The ΔpanCD mutant was found to be auxotrophic for pantothenate with no detectable reversion to prototrophy when $1\times10^{10}$ cells were plated on minimal medium. The growth rate of the mutant was identical to wild type H37Rv in broth cultures in the presence of exogenous pantothenate (data not shown). The attenuation of the ΔpanCD mutant was assessed by infection of immunocompromised SCID mice. SCID mice infected intravenously with H37Rv succumbed to the resulting infection in about 5 weeks. In contrast, all mice infected with the ΔpanCD mutant survived for more than 36 weeks (average, 253 days) (FIG. 10*a*). This attenuation is due to pantothenate auxotrophy as the full virulence phenotype was restored when the panCD wild type genes were integrated into the chromosome of the ΔpanCD mutant in single copy. Enumeration of bacterial burdens in SCID mice infected with H37Rv and the ΔpanCD-complemented strain showed a rapid increase in bacterial numbers in the spleen, liver and lung, until they succumbed to infection. In contrast, mice infected with the ΔpanCD mutant showed an initial drop in bacterial numbers in the spleen and liver followed by a gradual increase in the number of viable bacteria, reaching $1\times10^6$ colony-forming units (CFU) by day 224 (FIG. 10B). Notably, the CFU values increased to $1\times10^8$ in the lungs of the infected mice. The ability of ΔpanCD-infected SCID mice to survive despite a substantial bacterial burden in their lungs emphasizes the extent of attenuation in this mutant and compares with the phenotype observed with the *M. tuberculosis* whiB3 and sigH mutants described recently (Steyn et al., 2000; Kaushal, 2000). Notably, SCID mice infected with bacille Calmette-Guerin-Pasteur (BCG-P) strain succumbed to infection by 83 days (Weber et al., 2000) in contrast to the prolonged survival observed in LpanCD-infected mice.

Studies in immunocompetent mice further demonstrate the attenuation of the ΔpanCD mutant. Survival studies showed that BALB/c mice infected with H37Rv succumbed to infection by day 25 (average, 21 days) and mice infected with an identical dose of the panCD-complemented strain succumbed to infection between days 21 to 53 (average, 37 days). Importantly, all mice infected with $1\times10^6$ CFU of the ΔpanCD mutant survived 375 days, when the experiment was terminated (FIG. 10C). At 3 weeks post infection, in contrast to the H37Rv strain, BALB/c mice infected with ΔpanCD mutant showed a 10-fold increase in bacterial numbers in the lungs followed by a gradual decline in viable numbers over the next 38 weeks of infection (FIG. 10D) and the bacterial burden gradually declined in the spleen and liver throughout the course of infection (FIG. 10E). Histopathologic examination of the lungs from mice infected with either H37Rv or the ΔpanCD-complemented strain, showed severe, diffuse lobar granulomatous pneumonia (FIG. 11A,B). The pneumonia affected more than 50% of the lung, and was pyogranulomatous with marked necrosis in the advanced consolidated areas, particularly in the lungs of mice challenged with H37Rv. Both of these strains caused severe granulomatous splenitis and widespread granulomatous hepatitis. At 3 weeks post-infection with the ΔpanCD mutant, low to moderate numbers of focal infiltrates of mononuclear cells scattered throughout the lung were seen (FIG. 11C). The spleen was moderately enlarged with scattered granulomas. Similarly, the liver showed numerous focal granulomas. At 24 weeks post-infection, consistent with the bacterial numbers, histological examination of the lungs from mice infected with the ΔpanCD mutant showed only occasional focal mild infiltrations, predominately lymphocytic (FIG. 11D). The spleen showed only mild histiocytic hyperplasia and there were fewer, focal, predominately lymphocytic accumulations in the liver.

The mechanisms that allow the persistence of the ΔpanCD mutant bacteria for over 8 months in the SCID mouse model remain unclear. We speculate the functional role of an unidentified permease in transporting adequate amount of pantothenate in the ΔpanCD mutant that allows its persistence but not the ability to cause disease. A pantothenate permease that transports pantothenate have been described in *Plasmodium falciparum* and *Escherichia coli* (Saliba and Kirk, 2001; Jackowski and Alix, 1990). In the lungs of immunocompetent mice, an initial growth of the ΔpanCD mutant during the first 3 weeks is followed by a steady decline in bacterial numbers following the onset of an adaptive immune response. The intracellular lifestyle of *M. tuberculosis* poses significant challenges to the bacterium in acquiring essential nutrients. Pantothenic acid or its derivatives have been shown to confer resistance to oxidative stress (Slyshenkov et al., 1996) and lack of pantothenate biosynthesis in the ΔpanCD mutant may render it more susceptible to such adverse effects. Likewise, a pantothenate kinase (panK) mutant of *Drosophila* was shown to display membrane defects and improper mitosis and meiosis due to decreased phospholipid biosynthesis (Afshar et al., 2001). Therefore, it is plausible that the pantothenate salvage pathway is inadequate in restoring full virulence of the ΔpanCD mutant in the absence of a functional de novo biosynthetic pathway.

As a test of vaccine potential, immunized mice were challenged with virulent *M. tuberculosis* Erdman by the aerosol route (Collins, 1985). Following subcutaneous immunization, the ΔpanCD mutant could not be detected in the spleens or lungs of mice at 8 and 12 weeks. In the naive controls, the bacterial CFU values increased 10.000-fold in the lung during the first month after challenge. Similarly, substantial dissemination and growth in the spleen was detected within one month of the challenge in naive controls. In contrast, mice immunized with single or double doses of the ΔpanCD mutant displayed statistically significant reductions ($P<0.05$) in lung and spleen CFU values relative to naive controls. Mice vaccinated with BCG showed similar reduction in organ bacterial burdens compared to the nonimmunized controls (FIG. 11E,F). In these aerogenic challenge studies, no significant differences were detected in the lung and spleen CFU values for mice vaccinated with either the ΔpanCD mutant strain or with BCG. At 28 days after the aerogenic challenge with virulent *M. tuberculosis*, histopathological examination of lungs of ΔpanCD immunized mice revealed a less severe infection relative to the unvaccinated control mice. In controls, severe bronchitis, moderate pneumonia, and spread of the infection to the adjacent lung parenchyma was observed. By comparison, the ΔpanCD vaccinated mice had milder bronchitis and smaller areas of mild interstitial pneumonitis, with localized areas of granulomatous pneumonia in some mice. Importantly, no lung pathology was detected in vaccinated mice at the time of challenge (data not shown). Two groups of mice that were vaccinated with one or two doses of the ΔpanCD mutant and then challenged with *M. tuberculosis* Erdman were active and healthy for more than one year following the virulent challenge. Histopathological analysis of lung sections from these mice showed only mild inflammation and fibrosis despite the chronic infection.

By creating a *M. tuberculosis* strain that is defective in pantothenate biosynthesis, we have taken a critical step in the rational development of an attenuated *M. tuberculosis* vaccine strain. We have shown that a functional pantothenate biosynthetic pathway, which is required for the synthesis of complex mycobacterial lipids, is essential for the virulence of *M. tuberculosis*. Although the precise mechanism of the reduced virulence is unclear, it is reasonable to speculate that this could be due to reduced synthesis of toxic polyketides and secreted lipids or a general slow down of metabolism. Tubercle bacilli lacking the two genes required to synthesize pantothenate failed to revert and were highly attenuated and less virulent than BCG vaccine when tested in the rigorous SCID mouse model of infection. Despite the reduced virulence associated with the deletion of the panCD genes, these vitamin auxotrophs remain persistent in vivo as shown by their ability to survive for at least eight months in immunocompetent mice. The persistence of this mutant strain undoubtedly contributes to the substantial immunogenicity seen in the mouse tuberculous challenge model. Overall, the ΔpanCD mutant has many of the characteristics necessary for a live vaccine candidate strain: it is attenuated by a non-reverting mutation and essentially avirulent while being persistent and immunogenic. Given the genetic differences between *M. bovis* and *M. tuberculosis* (Behr et al., 1999), one would predict that a rationally attenuated *M. tuberculosis* strain would have a more relevant repertoire of species-specific antigens and thus should elicit, in humans, more effective protective immune responses against tuberculous infections than BCG.

EXAMPLE 4

The Primary Mechanism of Attenuation of BCG is a Loss of Invasiveness Due to Host Cell Lysis Example Summary.

Tuberculosis remains a leading cause of death worldwide, despite the availability of effective chemotherapy and a vaccine. BCG, the *tuberculosis* vaccine, is an attenuated mutant of *M. bovis* that was isolated following serial subcultivations, yet the basis for this attenuation has never been elucidated. A single region (RD1), deleted in all BCG substrains, was deleted from virulent *M. bovis* and *M. tuberculosis* strains and the resulting three ΔRD1 mutants were significantly attenuated for virulence in both immunocompromised and immunocompetent mice. Like BCG, *M. tuberculosis* ΔRD1 mutants protect mice against aerosolized *M. tuberculosis* challenge and these mutants also consistently display altered colonial morphotypes. Interestingly, the ΔRD1 mutants failed to cause necrosis, via lysis, of pneumocytes, a phenotype that had been previously used to distinguish virulent *M. tuberculosis* from BCG. We conclude that the primary attenuating mechanism of BCG is the loss of cytolytic activity, resulting in reduced invasiveness.

Introduction.

BCG (bacille Calmette and Guerin), was first isolated from *M. bovis* following serial subculturing of *M. bovis* in 1908 (Calmette and Guerin, 1909). Drs. Calmette and Guerin set out to test the hypothesis that a bovine tubercle *bacillus* could transmit pulmonary *tuberculosis* following oral administration (Calmette and Guerin, 1905; Gheorghiu, 1996) and developed a medium containing beef bile that enabled the preparation of fine homogenous bacillary quspensions. After the 39th passage, the strain was found to be unable to kill experimental animals (Calmette and Guerin, 1909). Between 1908 and 1921, the strain showed no reversion to virulence after 230 passages on bile potato medium (Gheorghiu, 1996), which is consistent with the attenuating mutation being a deletion mutation. In the animal studies that followed, BCG was shown to be attenuated, but it also protected animals receiving a lethal challenge of virulent tubercle bacilli (Calmette and Guerin, 1920). BCG was first used as a vaccine against *tuberculosis* in a child in 1921 (Weill-Halle and Turpin, 1925). From 1921 to 1927, BCG was shown to have protective efficacy against TB in a study on children (Id.; Calmette and Plotz, 1929) and was adopted by the League of Nations in 1928 for widespread use in the prevention of *tuberculosis*. By the 1950's, after a series of clinical trials, the WHO was encouraging widespread use of BCG vaccine throughout the world (Fine and Rodrigues, 1990). Although an estimated 3 billion doses have been used to vaccinate the human population against *tuberculosis*; the mechanism that causes BCG's attenuation remains unknown.

Mahairas et al. (1996) first compared the genomic sequences of BCG and *M. bovis* using subtractive hybridization and found that there were three Regions of Difference (designated RD1, RD2, and RD3) present in the genome of *M. bovis*, but missing in BCG. Behr et al. (Behr et al., 1999) and others (Gordon et al., 2001) later identified 16 large deletions, including RD1 to RD3, present in the BCG genome but absent in *M. tuberculosis*. Eleven of these 16 deletions were unique to *M. bovis*, while the remaining 5 deletions were unique to BCG. One of these 5 deletions, designated RD1 (9454 bp), was absent from all of the BCG substrains currently used as TB vaccines worldwide and it was concluded that the deletion of RD1 appeared to have occurred very early during the development of BCG, probably prior to 1921 (Behr et al., 1999). It is reasonable to hypothesize that RD1 was the primary attenuating mutation first isolated by Calmette and Guerin to generate BCG from *M. bovis*. Attempts to restore virulence to BCG with RD1-complementing clones have been unsuccessful (Mahairas et al., 1996).

Results

Figure 12:
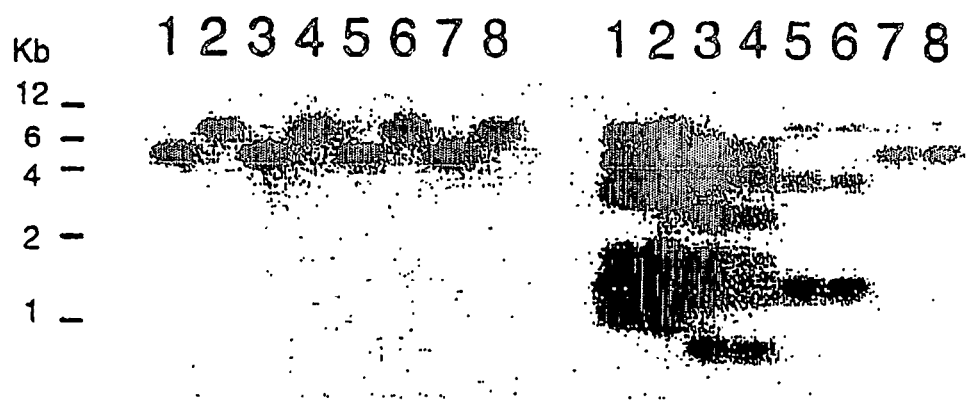

RD1 deletions of *M. bovis* and *M. tuberculosis* are attenuated for virulence in immunocompromised mice. To test if RD1 is essential for virulence in *M. bovis* and *M. tuberculosis*, it was necessary to delete the RD1 (FIG. 1a) from virulent strains, demonstrate loss of virulence, and then restore virulence by complementation with the RD1 DNA. Since the original *M. bovis* parent of BCG was lost in World War I (Grange et al., 1983), we initiated studies with virulent *M. bovis* Ravenel and a variety of virulent *M. tuberculosis* strains. Despite success in generating an unmarked deletion mutant of RD1 in *M. tuberculosis* with a plasmid transformation system[1,2], over 100 independent transformations failed to yield an RD1 deletion in *M. bovis*. As an alternative strategy, specialized transduction (Bardarov et al., 2002)[3] was successfully used to generate RD1 deletion mutants not only in *M. bovis* Ravenel, but also the H37Rv, Erdman, and CDC1551 strains of *M. tuberculosis* (FIG. 12). This deletion represents the largest deletion mutation generated by a targeted disruption in *M. tuberculosis* or *M. bovis* made to date and demonstrates the utility of the specialized transduction system. Moreover, since the parental specialized transducing phage has been shown to infect over 500 clinical *M. tuberculosis* isolates (Jacobs et al., 1987), it should be possible to introduce the RD1 deletion into any *M. tuberculosis* or *M. bovis* isolate of interest.

To determine if the RD1 deletion causes an attenuating phenotype in *M. bovis* and *M. tuberculosis*, the *M. tuberculosis* H37Rv ΔRD1 was inoculated intravenously into immunocompromised mice possessing the SCID (severe combined immunodeficiency) mutation. Groups of ten mice were injected intravenously with either $2 \times 10^6$ wild type or ΔRD1 strain of *M. tuberculosis* and *M. bovis*, and three mice per group were sacrificed 24 hours later to verify the inoculation doses. All of the SCID mice infected with the parental *M. tuberculosis* or *M. bovis* strain died within 14 to 16 days post-infection (FIG. 12A). In contrast, the SCID mice infected with equal doses of the ΔRD1 strains of *M. tuberculosis* or *M. bovis* were all alive at 25 to 41 days post-infection, demonstrating a highly significant attenuation of the virulence of both strains. It is important to note that BCG-Pasteur kills SCID mice approximately 70 days post-infection (FIG. 13B), suggesting that BCG substrains have acquired additional attenuating mutations which are consistent with the deletion analysis of BCG strains (Behr et al., 1999) and the previous failures to restore virulence with the RD1 region (Mahairas et al., 1996).

Figure 13:
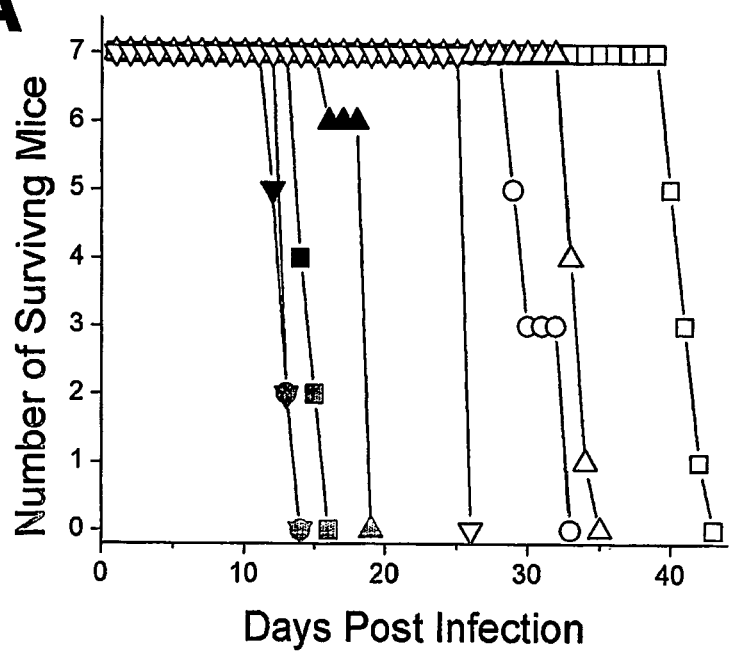
Figure 13:
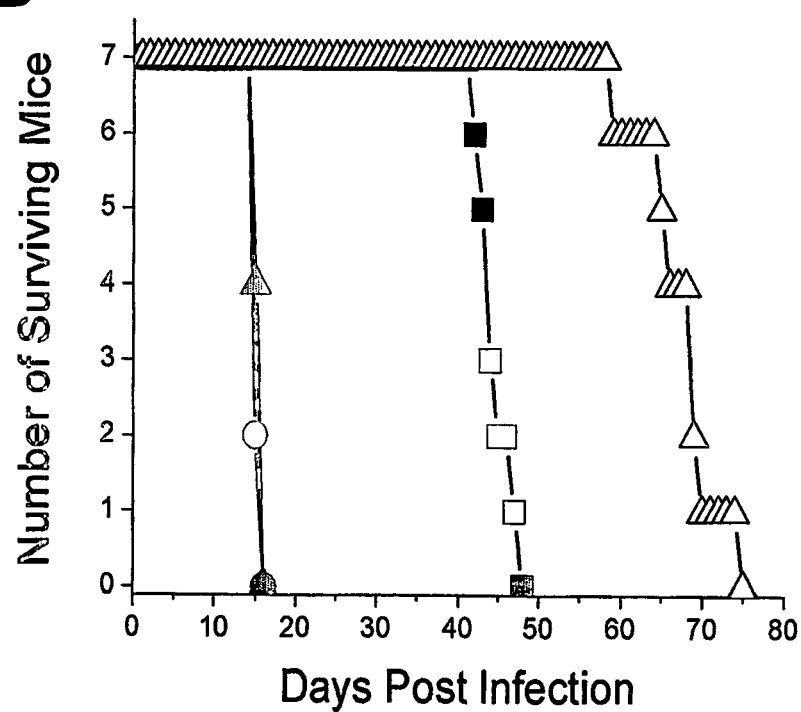

To prove that the attenuation of virulence was due to the RD1 deletion, the *M. tuberculosis* ΔRD1 was transformed with an integrating cosmid, 2F9, containing the RD1 region from *M. tuberculosis* H37Rv[4]. SCID mice were infected as described above and the attenuation for virulence was restored to the parental virulent phenotype (FIG. 13B). These results strongly suggest that the genes deleted from the RD1 region contribute to the virulence phenotype.

Figure 13C:
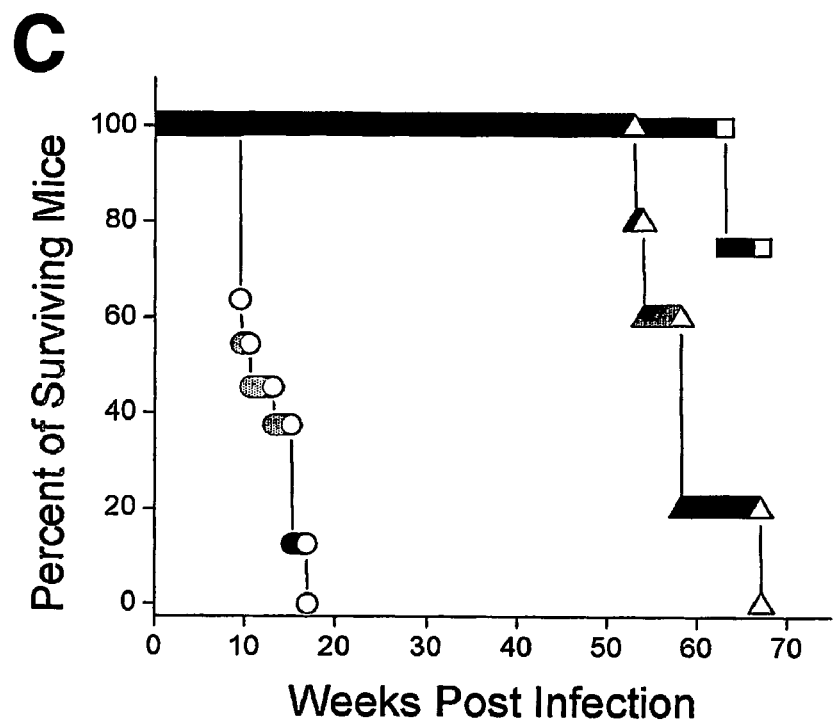

The *M. tuberculosis* ΔRD1 is highly attenuated in immunocompetent BALB/c mice. The virulence of the *M. tuberculosis* ΔRD1 mutant was further assessed by intravenous inoculation of immunocompetent BALB/c mice. While the virulent parent *M. tuberculosis* strain killed the BALB/c mice in 10 to 17 weeks post-infections, 100% of mice were alive at 48 weeks and 43 weeks post-infections in two independent experiments (FIG. 13C).

While infection with BCG and *M. tuberculosis* ΔRD1 yielded similar survival results in BALB/c mice, there were substantial differences in the growth kinetics in mice. BCG grew in a limited fashion in lungs, liver and spleen in BALB/c mice during the 22 weeks of the experiment (FIGS. 4b-d). In contrast, the *M. tuberculosis* ΔRD1 strain grew in a fashion indistinguishable from the parental *M. tuberculosis* H37Rv in all mouse organs for the first 8 weeks. Thereafter, mice infected with the parental *M. tuberculosis* failed to contain the infection leading to mortality. Strikingly, mice infected with the *M. tuberculosis* ΔRD1 showed a definite control over infection resulting in significantly prolonged survival of mice (FIG. 4b-d).

Histopathological examination further demonstrated that the mutant was attenuated in virulence compared to the parent strain H37Rv (FIG. 5d-f). In contrast to the rapidly progressive infection with the parent strain, the lung lesions caused by the mutant were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again, at 22 weeks post-infection, the lungs showed peribronchial and perivascular inflammatory cell accumulations and focal, generally non-confluent, granulomas now with a prominent lymphocytes infiltration. The numbers of acid fast bacilli were reduced. Liver lesions consisted of low numbers of scattered granulomas. Spleens were smaller, with persistent granulomas in the red pulp. Mice infected with *M. bovis* BCG showed mild lesions in the lung, liver and spleen at all time points (FIG. 5g-i). At longer time intervals post-infection the lesions were fewer in number, and smaller with prominent lymphocytic infiltrations. At 14 weeks post-infection, *M. bovis* BCG was below the level of detection by acid fast staining. In summary, whereas *M. tuberculosis* ΔRD1 initially grew in a manner similar to the parental *M. tuberculosis* H37Rv, this RD1 mutant was limited in the extent of spread of infection, particularly in the lung. This contrasts the extensive and severe damage caused by the parent strain. The subsequent resolving granulomas, localization of the lesions and changes in the composition of the inflammatory cell infiltrations suggested that the mice mounted an effective immune response to combat *M. tuberculosis* ΔRD1 infection and thereby reduced the numbers of viable organisms.

Early BCG properties: Altered colonial morphotypes and long-term immunogenicity.

While frozen stocks of the original BCG strain do not exist, written records do exist describing the early BCG strains, as Dr. Calmette sent the strains to many laboratories. In a study published in 1929, Petroff and colleagues reported that BCG displayed two distinct colony types (Petroff et al., 1929). One morphotype was a smooth (S) phenotype that was flat and corded (like the parental virulent strain) and the second was a rough and raised (R) phenotype. The *M. tuberculosis* ΔRD1 mutant was generated independently four times and consistently yielded a 20 to 50% mixture of two colonial morphotypes on Middlebrook medium without Tween 80 (FIG. 3b). The distinction of these two types of morphology could be noted even when the colonies were less than two weeks old, as the rough colonies were constricted and elevated with only a small portion of the base of the colony attached to the agar, while the smooth colonies tended to be flattened and spread out. When colonies grew older, e.g. 6 weeks old, the rough colonies remained more constricted compared to those of smooth colonies. The rough colonies exhibited large folds on the surface (FIG. 3f-g), as compared to those of the smooth colonies that exhibited small wrinkles (FIG. 3e).

The generation of two distinct colonial morphotypes must be a phenotypic change induced by the deletion of RD1. The morphotypes could not be cloned, as repeated subculturing of either the R or S colonies continued to yield both colonial morphotypes. Moreover, Southern analysis of R and S colonies revealed each morphotype had the same RD1-deleted genotype (FIG. 3d). Furthermore, complementation of *M. tuberculosis* ΔRD1 with the RD1 region restored the mutant phenotype back to the homogenous parental S phenotype (FIG. 3a-c). These results suggest that the variable morphotypes resulted directly from the RD1 deletion. It can therefore be postulated that a regulator of colonial morphology is affected by one or more of the deleted genes.

One of the hallmark characteristics of BCG is its ability to provide protection against aerosolized challenge with virulent *M. tuberculosis*. To test the potential of *M. tuberculosis* ΔRD1 to immunize and protect mice against tuberculous challenge, we used the model of subcutaneous immunization of C57BL/6 mice followed by an aerogenic challenge with virulent *M. tuberculosis* (McGuire et al., 2002). Groups of mice were vaccinated subcutaneously with either $1\times10^6$ BCG 9 or $1\times10^6$ *M. tuberculosis* ΔRD1. Eight months following vaccination, the mice were all healthy, thereby demonstrating attenuation in a third mouse strain. Vaccinated and unvaccinated mice were aerogenically challenged with 200 CFU of the acriflavin-resistant strain of *M. tuberculosis* Erdman. Twenty-eight days after the challenge, the mice were sacrificed and the bacterial burden in the lungs and spleens were determined (see Table 5). Naive mice served as controls. While the acriflavin-resistant *M. tuberculosis* grew to $6.61\pm0.13$ ($\log^{10}$ CFU) in lungs of naive mice, both the BCG-vaccinated and *M. tuberculosis* ΔRD1-vaccinated mice exhibited greater than 1 log protection in lungs with CFU values of $5.07\pm0.10$ ($p<0.001$ relative to controls) and $5.11\pm0.14$ ($p<0.001$), respectively, detected at the four week time point. The *M. tuberculosis* ΔRD1 also protected against hematogenous spread; CFU values in the spleen were $5.26\pm0.11$ for the controls, $4.00\pm0.33$ ($p<0.01$) for the *M. tuberculosis* ΔRD1 immunized mice, and $3.85\pm0.17$ ($p<0.01$) for the BCG vaccinated animals. Thus, the *M. tuberculosis* ΔRD1 shares long-term immunogenicity like BCG.

TABLE 5

Bacterial burden of virulent *M. tuberculosis* in uninoculated mice and mice inoculated with BCG and H37Rv ΔRD1.

| Vaccination strain | Lung ($\log_{10}$CFU) | Spleen (log10CFU) |
|---|---|---|
| — | $6.61 \pm 0.13$ | $5.26 \pm 0.11$ |
| BCG | $5.07 \pm 0.10$*** | $3.85 \pm 0.17$** |
| H37Rv ΔRD1 | $5.11 \pm 0.14$*** | $4.00 \pm 0.33$** |

**$p < 0.01$;
***$p < 0.001$.

Discussion

BCG is a mutant of *M. bovis* that was isolated over 94 years ago and characterized for its attenuation for virulence in animals. For over 80 years, BCG has been used as a *tuberculosis* vaccine having been given to 3 billion humans. It is currently the only anti-tuberculous vaccine available for use in humans, yet its precise attenuating mutations and mechanisms of attenuation have never been determined. Previous studies had identified regions of the *M. bovis* chromosome that were absent from BCG, but present in virulent *M. bovis* and *M. tuberculosis* strains (Mahairas et al., 1996; Gordon et al., 2001). An elegant microarray analysis has also demonstrated that there was only one deletion common to all BCG strains; the authors hypothesized this was the primary attenuating mutation in the original BCG strain isolated by Drs. Calmette and Guerin (Behr et al., 1999).

Using a combination of targeted deletion mutagenesis, virulence assays, and complementation analysis, we have been able to unambiguously prove that RD1 is required for virulence for *M. tuberculosis*, and by analogy for *M. bovis*, for the first time. Moreover, the combination of phenotypes associated with the early BCG strains: i) the attenuation for virulence, ii) the altered colonial morphotypes, and iii) the ability to confer long-term immunogenicity in animals allow us to conclude that the RD1 deletion was the primary attenuating mutation in the original BCG isolate.

With regards to the ΔRD1 mutant histology, at 22 weeks post infection, it was noted that the mutant was limited in the extent of the spread of infection, in contrast to the extensive damage caused by the parental strain. Interestingly, Pethe et al. (2001) determined that *M. tuberculosis* needs to bind and/or invade epithelial cells in order to disseminate and cause widespread destruction of the lung, whilst another study reported that pulmonary M cells can act as a portal of entry to the lung for the tubercle bacilli (Teitelbaum, 1999). In relation to in vitro analyses, studies utilizing a model of the alveolar barrier, consisting of pneumocytes and monocytes, described how *M. tuberculosis* infection of the pneumocytes resulted in cytolysis, which disrupted the barrier and allowed more efficient translocation of intracellular bacilli (Bermudez et al., 2002).

Notes

[1] The following four primers were used to amplify upstream and downstream flanking sequences (UFS and DFS, respectively) for the construction of the RD1 deletion mutants. UFS was amplified using TH201: GGGGGCG-CACCTCAAACC (SEQ ID NO:5) and TH202: ATGTGC-CAATCGTCGACCAGAA (SEQ ID NO:6). DFS was amplified using TH203: CACCCAGCCGCCCGGAT (SEQ ID NO:7), and TH204: TTCCTGATGCCGCCGTCTGA (SEQ ID NO:8). Recognition sequences for different restriction enzymes were included at the ends of each primer to enable easier manipulation.

[2] The unmarked deletion mutant of *M. tuberculosis* H37Rv, mc²4002, was generated by transformation using a sacB counterselection (Snapper et al., 1988; Pelicic et al., 1996; Pavelka et al., 1999). Specifically, the plasmid pJH508 was created by first cloning UFS into KpnI and XbaI sites, then cloning DFS into EcoRI and HindIII sites of pJH12, a pMV261-derived *E. coli-Mycobacteria* shuttle plasmid, to create pJH506 in which UFS and DFS flanked a green fluorescent protein gene (GFPuv, Clonetech) whose expression was driven by the *M. leprae* 18 Kd promoter. The UFS-gfp-DFS cassette was sub-cloned into the EcoRV site of plasmid pYUB657 to create pJH508. The first homologous recombination involved the identification of hygromycin resistant colonies, resulting from the transformation of *M. tuberculosis* with pJH508. Southern analysis of the NcoI-digested DNA isolated from hygromycin resistant colonies probed with UFS or DFS, confirmed the presence of a single copy of pJH508 inserted into the *M. tuberculosis* genome. The transformant (mc²4000) identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

[3] Specialized transduction is a mycobacteriophage-based method for the delivery of homologous DNA constructs using conditionally replicating shuttle phasmids (Jacobs et al., 1987; Bardarov et al., 1997; Carriere et al., 1997) has been used successfully for *M. tuberculosis* (Glickman et al., 2000, 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature-sensitive mycobacteriophage derived from TM4. The transduction was performed by growing *M. tuberculosis* to an O.D.$_{600}$ of 1.0, washing twice with MP buffer (50 mM Tris pH 7.6, 150 mM NaCl, 10 mM MgCL$_2$, 2 mM CaCl$_2$), resuspending into an equal volume of MP buffer and mixing with the transducing phage phAEKO1 at an MOI of 10. The mixtures were incubated at 37° C. overnight, then plated on 7H10 plates supplemented with hygromycin at 50 µg/ml. Hygromycin resistant colonies were analyzed by PCR and Southern analysis, as described above, to confirm the deletion of RD1.

[4] Complementation analyses was performed using the integration proficient cosmids (Skjot et al., 2000; van Pinxteren et al., 2000a) pYUB412 made by S. Bardarov, a library made by F. Bange, and cosmid identified and generously provided by S. T. Cole.

EXAMPLE 5

Vaccine Efficacy of a Lysine Auxotroph of *M. tuberculosis*

In this Example, we describe the in vivo growth phenotype and vaccine efficacy of a lysine auxotrophic mutant of *Mycobacterium tuberculosis* strain H37Rv. An immunization experiment using the mouse model with an aerosol challenge showed that two doses of the *M. tuberculosis* mutant were required to generate protection equivalent to that of the BCG vaccine.

Despite the existence of anti-microbial drugs and a widely used vaccine, *Mycobacterium tuberculosis* remains the primary cause of adult death due to a bacterial agent (Dolin et al., 1994). The emergence of multi-drug resistant strains of *M. tuberculosis*, the variable efficacy of the current vaccine, the bacille-Calmette and Geurin (BCG), and the HIV pandemic have all contributed to a growing global *tuberculosis* problem.

Several studies have described the development of attenuated auxotrophic strains of BCG and/or *M. tuberculosis* (Guleria et al., 1996; Hondalus et al., 2000; Jackson et al., 1999; Smith et al., 2001). All of these studies utilized single immunization protocols and demonstrated differences in the protective responses thus elicited. In this study, we describe the in vivo growth characteristics of a previously described lysine auxotroph of *M. tuberculosis* H37Rv (Pavelka and Jacobs, 1999), and evaluate the vaccine potential of this mutant by a multiple immunization protocol in a mouse model of the human disease, using an aerosol challenge.

Clearance of the *M. tuberculosis* lysine auxotroph in SCID mice. Female SCID mice were bred at the animal facility of the Albert Einstein College of Medicine. The animals were maintained under barrier conditions and fed sterilized commercial mouse chow and water ad libitum. The *M. tuberculosis* strains Erdman, mc²3026 (ΔlysA::res) (Id.), and mc²3026 bearing pYUB651 (expressing the wild-type lysA gene) were grown in Middlebrook 7H9 broth (Difco) supplemented with 0.05% Tween-80, 0.2% glycerol, 1×ADS (0.5% bovine serum albumin, fraction V (Roche); 0.2% dextrose; and 0.85% NaCl) or on Middlebrook 7H10 or 7H11 solid medium (Difco) supplemented with 0.2% glycerol and 10% OADC (Becton Dickinson). Culture media for the lysine auxotroph were supplemented with 1 mg/ml of L-lysine (for both liquid and solid media), and 0.05% Tween-80 was also added to solid medium. Liquid cultures were grown in 490 cm² roller bottles (Corning) at 4-6 rpm. Plates were incubated for 3-6 weeks in plate cans. All cultures were incubated at 37° C.

Titered frozen stocks of the bacteria were thawed and diluted appropriately in phosphate buffered saline containing 0.05% Tween-80 (PBST). The bacterial suspensions were plated at the time of injection to confirm the number of viable bacteria. Intravenous injections were given via a lateral tail vein. At various time points post-injection (24 hours, then once weekly), 3 mice were sacrificed, and the lungs, liver, and spleen removed and homogenized separately in PBST using a Stomacher 80 (Tekmar, Cincinnati, Ohio). The homogenates were diluted in PBST and plated to determine the number of CFU/organ. Note that mice were sacrificed at 24 hours post-injection in order to compare the bacterial colony forming units recovered from the mice with the colony forming units in the suspensions at the time of injection. Thus the bacterial counts reported at time zero actually represent the viable bacteria recovered from the mice at 24-hours post-injection.

Figure 14:
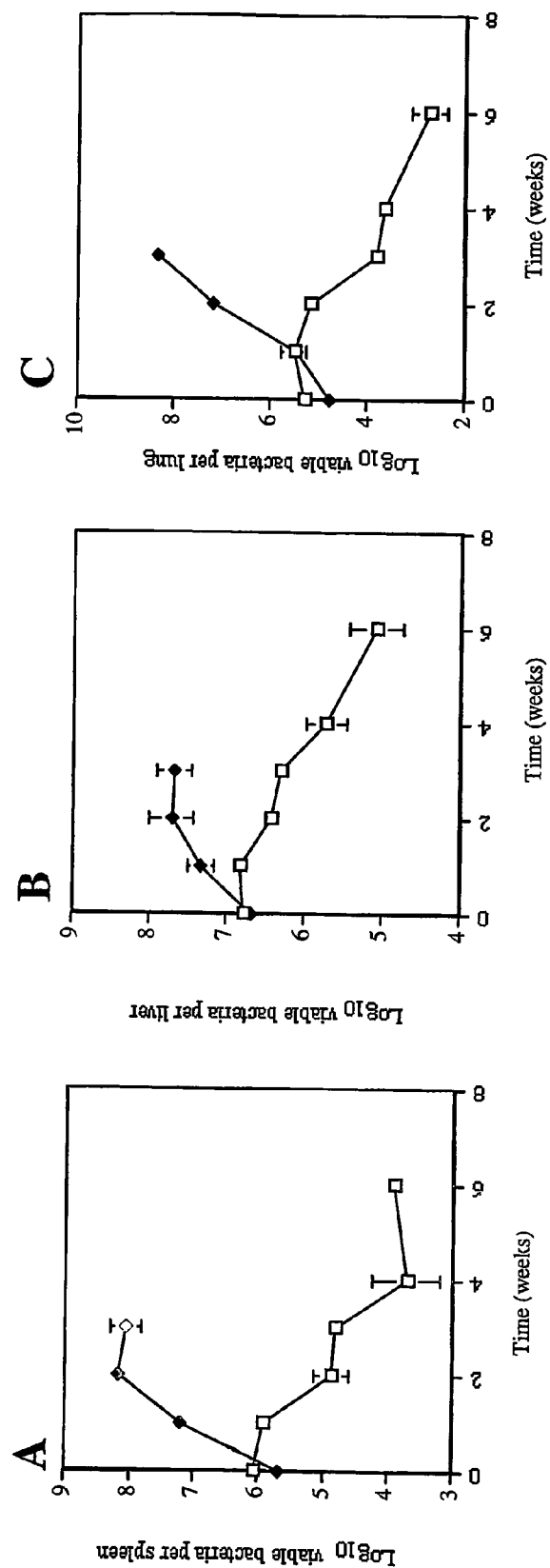
FIGS. 14A-14C are graphs summarizing experiments demonstrating the clearance of the lysine auxotroph in SCID mice. The viable bacterial counts are shown for the spleens, livers, and lungs of SCID mice injected intravenously with the lysine auxotroph strain and the prototrophic control strain. Three mice were assayed at each time point. The error bars indicate the standard deviations of the mean values. Note that the counts at time zero are the counts obtained at 24 hours post-injection, as described in Example 5. Panels A, B and C show the log of the viable bacteria in each organ after injection with 1×10⁷ CFU of the Lys⁻ *M. tuberculosis* mutant mc²3026 (□), or 1×10⁷ CFU of the complemented Lys⁺ *M. tuberculosis* strain mc²3026/pYUB651 (♦).
Figure 15:
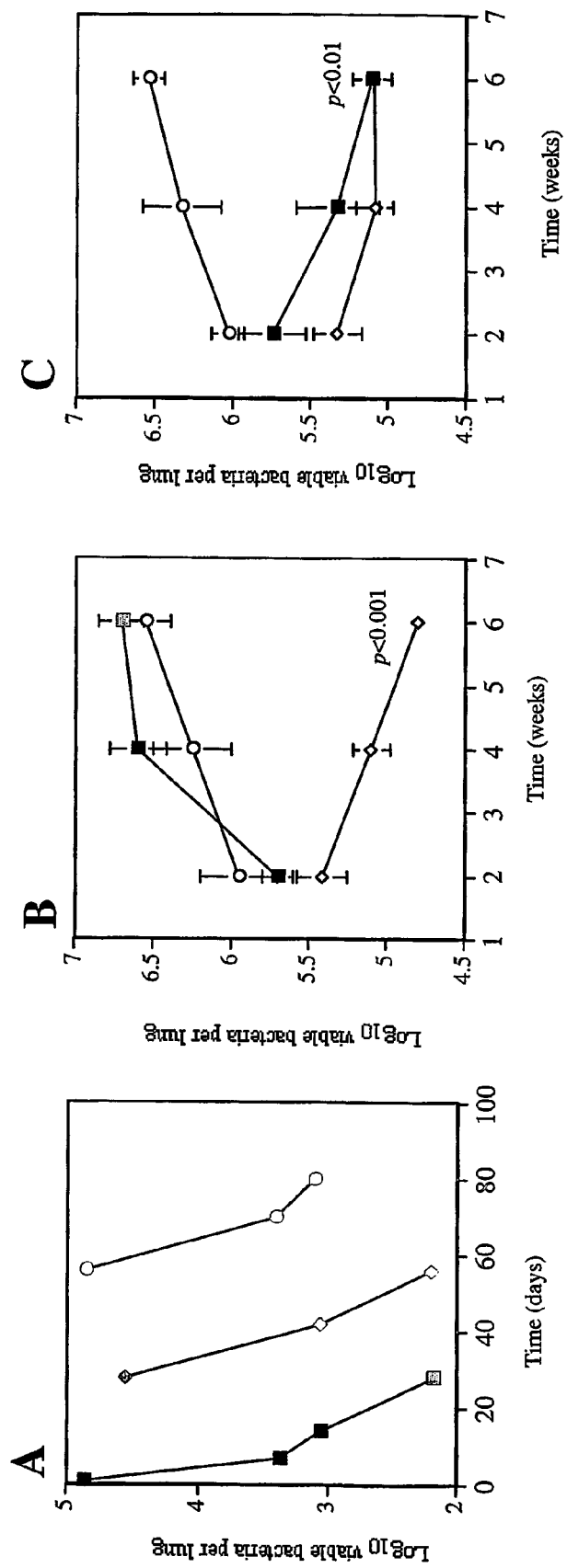
FIGS. 15A-15C are graphs summarizing experimental results of experiments that establish the vaccine efficacy of the *M. tuberculosis* lysine auxotroph mc²3026. C57Bl/6 mice were injected intravenously with 1×10⁶ CFU of the *M. tuberculosis* lysine auxotroph mc²3026, followed by one or two additional injections at 4 week intervals. Five mice were sacrificed weekly after each immunization and the viable bacteria counts of the auxotroph determined in the lungs and spleens. Control mice were given a similar amount of BCG-Pasteur or only PBST. Shown in Panel A is the clearance of the auxotroph from the lungs of the mice after each immunization period; one injection (■), two injections (◇), and three injections (○). Three months after the initial immunization the vaccinated and control mice were challenged with virulent *M. tuberculosis* Erdman by the aerosol route. Five challenge mice were sacrificed following the challenge period and the lung homogenates plated to check the viable counts of the challenge inoculum. Groups of vaccinated and control mice were sacrificed at 14, 28, and 42 days later and the lung and spleen homogenates plated to determine viable colony forming units. Shown in Panel B are the viable challenge bacteria per lung of mice given one dose of the *M. tuberculosis* lysine auxotroph, and in panel C, the viable challenge bacteria per lung of mice given two doses of the auxotroph. Key: Viable challenge bacteria per lung of mice given the *M. tuberculosis* lysine auxotroph mc²3026 (■), BCG-Pasteur (◇), or PBST (○). P values are indicated in the figure. Note that the results shown here are for the lungs. Similar results (not shown) were obtained from the spleens in all the experiments.
Figure 16:
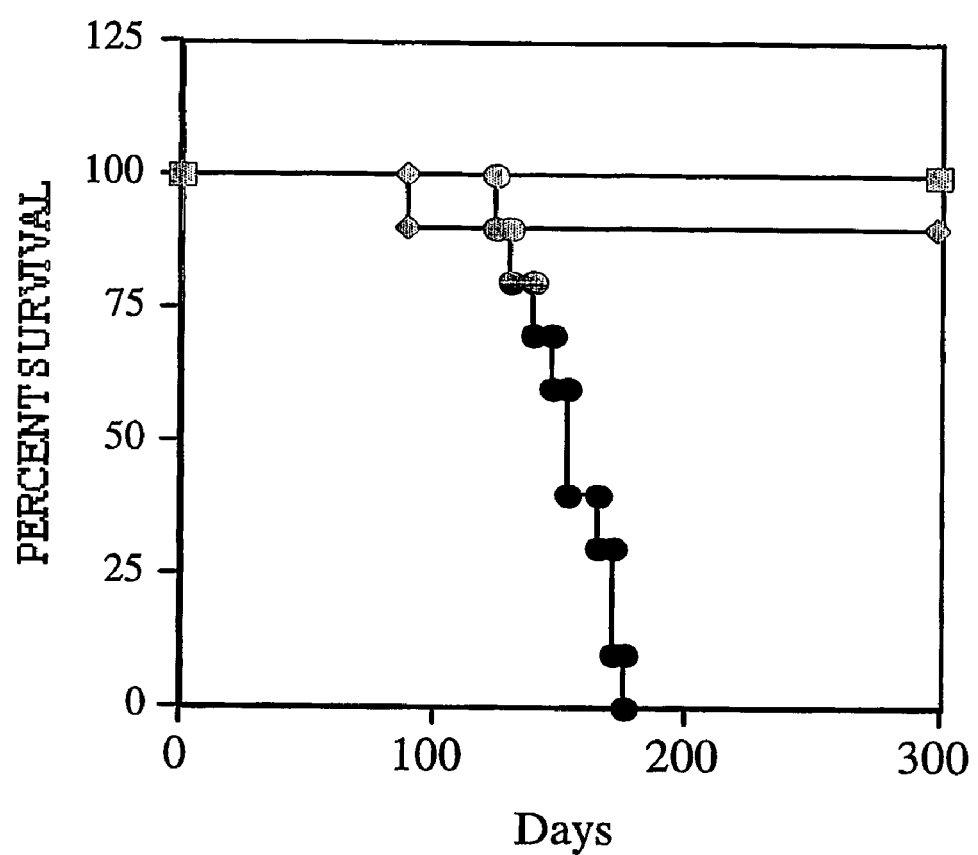
FIG. 16 shows a graph summarizing experiments establishing the survival curves of mice immunized three times with the *M. tuberculosis* lysine auxotroph mc²3026. C57Bl/6 mice were injected intravenously with 1×10⁶ CFU of the *M. tuberculosis* lysine auxotroph mc²3026, followed by two more injections at 4 week intervals, and challenged as described in Example 5. The percent survival is shown above for mice immunized thrice with the *M. tuberculosis* lysine auxotroph mc²3026 (■, 5 mice total), once with BCG-Pasteur (♦, 5 mice), and for the PBST controls (●, 10 mice).

The lysine auxotrophic strain was cleared from and did not appear to grow in the examined organs of the SCID mice, while the complemented strain multiplied extensively (FIG. 14). Interestingly, the auxotrophic inoculum was cleared from the spleens and lungs but persisted somewhat longer in the liver (FIG. 14B). The mice receiving the complemented *M. tuberculosis* mutant died within three weeks of challenge, while the mice given the auxotrophic *M. tuberculosis* mutant did not display any gross organ pathology and survived for at least the duration of the experiment.

Two immunizations with the *M. tuberculosis* lysine auxotroph $mc^2$3026 are required to match the efficacy of vaccination with BCG-Pasteur. We tested the vaccine potential of the lysine auxotroph $mc^2$3026 in the mouse model by means of a virulent aerosol challenge. Female, pathogen-free C57BL/6 mice (Jackson Laboratories, Bar Harbor, Me.) were vaccinated intravenously with ca. $1\times10^6$ CFU of the *M. tuberculosis* lysine auxotroph or BCG-Pasteur suspended in 0.2 ml PBST. Mice vaccinated with $mc^2$3026 were revaccinated at 4 week intervals and the number of viable organisms in the lungs and spleens determined weekly throughout the vaccination period, as described above for the SCID mouse experiments. Five mice were examined at each time point.

Immunized mice were challenged 3 months after the initial vaccination. A frozen aliquot of a *M. tuberculosis* Erdman stock was thawed and diluted in PBST to ca. $1\times10^6$ CFU/ml and 10 ml was introduced into the nebulizer of a Middlebrook aerosol chamber (Glas-Col, Terre Haute, Ind.). The mice were exposed to the infectious aerosol for 30 minutes, inhaling 50-100 CFU into their lungs over this period. Five mice were sacrificed immediately following the challenge period and the lung homogenates were plated to check the amount of the challenge inoculum actually reaching the lungs. Groups of vaccinated and control mice were sacrificed 14, 28, and 42 days later and the lung and spleen homogenates plated to determine the number of viable colony forming units of *M. tuberculosis* Erdman present. Data were analyzed using the Student's t-test and an analysis of variance between several independent means, using the In Stat Statistics program (GraphPad Software, San Diego).

A preliminary experiment demonstrated that a single intravenous immunization of immunocompetent C57BL/6 mice with the *M. tuberculosis* mutant did not generate a significant protective response to the subsequent aerosol challenge with virulent *M. tuberculosis* Erdman. In that experiment, the *M. tuberculosis* auxotroph was rapidly cleared from the mice (FIG. 15A), and the single immunization with the auxotroph was insufficient to reduce the bacterial burden in the lungs and spleens relative to a single immunization with BCG (FIG. 15B).

The failure of the auxotroph to confer protection might have been due to the inability of the mutant to persist long enough, or to synthesize enough antigen to induce an immune response that could significantly restrict the growth of the challenge organisms. One way to circumvent this problem is to give multiple doses of vaccine (Collins, 1991; Homchampa et al., 1992). To this end, mice were intravenously immunized two or three times at four-week intervals with the *M. tuberculosis* lysine auxotroph. In both cases, the vaccine strain was cleared from the lungs and spleens of all the mice at rates similar to that seen with the single immunization experiment (FIG. 15A). Three months after the first immunization the mice were challenged with *M. tuberculosis* Erdman by the aerosol route and the bacterial counts in the lungs and spleens were determined and compared to a BCG-Pasteur immunized control, as well as the sham immunized controls. As seen in FIG. 15C, double immunization with the *M. tuberculosis* lysine auxotroph induced a protective response that was equivalent to that of the BCG control. The reduction in counts in the lung and spleen was equivalent to a 100-fold reduction in bacterial counts compared to the unvaccinated control (FIG. 15C). The results from the triple immunization experiment were essentially similar as those from the double immunization experiment described above (data not shown). Furthermore, mice that were immunized with three doses of the *M. tuberculosis* lysine auxotroph and challenged with virulent *M. tuberculosis* Erdman survived at least as long as the BCG-immunized control mice (FIG. 16).

Several studies have described the development and vaccine efficacy of attenuated mutant strains of *M. tuberculosis* (Jackson et al., 1999; Hondalus et al., 2000; Smith et al., 2001). The first study reported that a purine auxotroph of *M. tuberculosis* was unable to grow in macrophages and was attenuated for growth in both mice and guinea pigs (Jackson et al., 1999). A guinea pig vaccination experiment determined that a single immunization with the auxotroph allowed the animals to restrict the growth of virulent *M. tuberculosis* in the lungs as well as a single immunization with wild-type BCG, following aerosol challenge. However, the reduction in growth of the challenge organism in the spleen afforded by the auxotroph was not as extensive as that afforded by BCG. Another study reported that a leucine auxotroph of *M. tuberculosis* Erdman cannot grow in macrophages and is avirulent to immunocompromised SCID mice (Hondalus et al., 2000). Immunocompetent mice vaccinated once with a *M. tuberculosis* leucine mutant did not significantly restrict the growth of the virulent challenge organism in the lungs or spleen as much as the control mice vaccinated with BCG (Id.). However, the mice immunized with the leucine auxotroph survived as long as the BCG immunized controls and exhibited a decreased histopathology relative to that seen in the non-immunized controls (Id.) A third study showed that *M. tuberculosis* proline and tryptophan auxotrophs were attenuated and a single immunization of mice with either of these mutants afforded protection against an intravenous challenge with virulent *M. tuberculosis*, comparable to that for BCG, as indicated by the mean survival times (Smith et al., 2001). In those experiments, mice immunized with pro or trp mutants could restrict the growth of the challenge organisms to the same extent as mice immunized with BCG, although the magnitude of protection in either case (*M. tuberculosis* auxotrophs or BCG) was not as extensive as that seen in the other studies (Id.).

In the present study we have demonstrated that a single immunization of mice with the avirulent *M. tuberculosis* lysine auxotroph did not generate an immune response capable of significantly restricting the growth of virulent *M. tuberculosis* Erdman following an aerogenic challenge. However, administration of a second or a third dose of this vaccine increased protection substantially, as measured by the number of viable bacteria per organ, to a level similar to that achieved with single dose of BCG-Pasteur. This level of protection did not seem to be greatly increased by a third dose of vaccine, although the triply immunized mice survived as long as the control mice immunized with a single dose of BCG-Pasteur. Mice that were immunized twice were not followed to determine mean survival time, but comparing the growth curves of the challenge bacteria following the double and triple immunizations, it seems likely that the survival time for the doubly immunized mice would be much the same as that for the triple-immunized mice.

The previous studies using *M. tuberculosis* auxotrophs as vaccine strains showed substantial variations in their effectiveness. This variability is likely to be due to a number of factors, including the different *M. tuberculosis* background strains used to construct the mutants, different mouse strains used in the various protection studies, and the different challenge organisms and challenge routes used. There was also considerable variation in the protective efficacy of the different vaccines compared to that observed in controls using BCG immunization. These differences pose a number of questions concerning the best indicators of protection, especially in the long term. Should viable bacterial counts or survival be the primary indicator of protection or should both be given equal weight? The results of this study indicate that more than one immunization with a *M. tuberculosis* lysine auxotroph did generate a significant protective response as indicated by both criteria. We believe it is important that multiple immunization protocols be considered in the further development of attenuated *M. tuberculosis* strains as potential human vaccines.

This is the first study demonstrating that a multiple immunization protocol using an auxotroph of *M. tuberculosis* can protect against a highly virulent aerosol challenge compared to that seen for BCG. Since BCG vaccines have shown variable efficacy when tested in humans, an auxotrophic *M. tuberculosis* vaccine might represent an attractive booster vaccine with which to augment childhood BCG immunization.

EXAMPLE 6

Mutants of *Mycobacterium tuberculosis* Having Two Attenuating Mutations are Safe and Provide Protection in Mammals Lacking CD4$^+$ Lymphocytes The experiments described in this Example employ materials and methods described in the other Examples.

Construction and characterization of *M. tuberculosis* ΔRD1ΔpanCD (mc$^2$6030). A pantothenate auxotroph of *M. tuberculosis* ΔRD1 was generated by specialized transduction and the strain designated mc$^2$6030. No CFU were detected on 7H11 when 5×10$^{10}$ CFU were plated (repeated twice), suggesting the reversion frequency to be below 10$^{-11}$.

Figure 17:
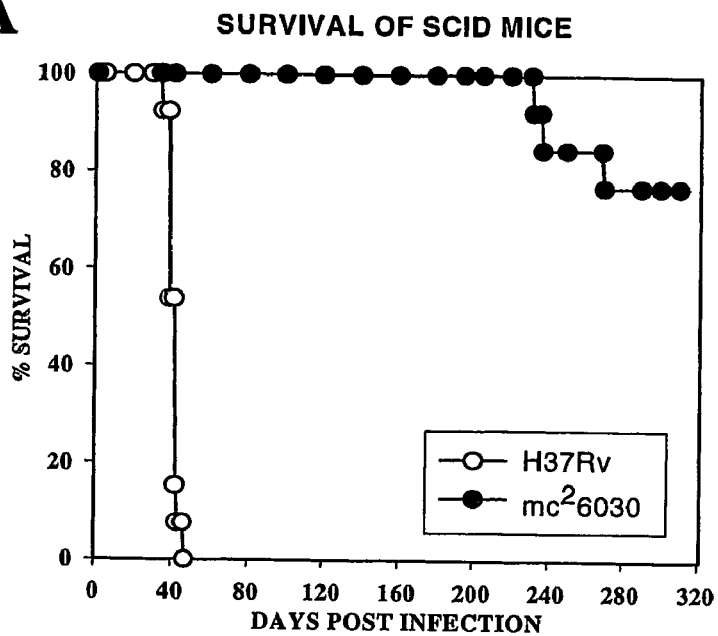
FIG. 17 shows graphs summarizing experimental results establishing that the virulence of strain mc²6030 is highly attenuated in SCID mice and BALB/c mice.
Figure 17:
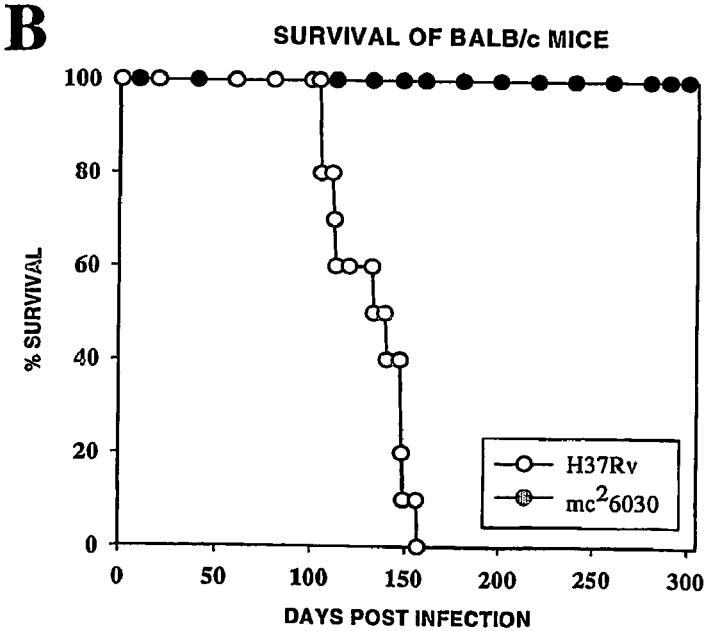
Figure 18:
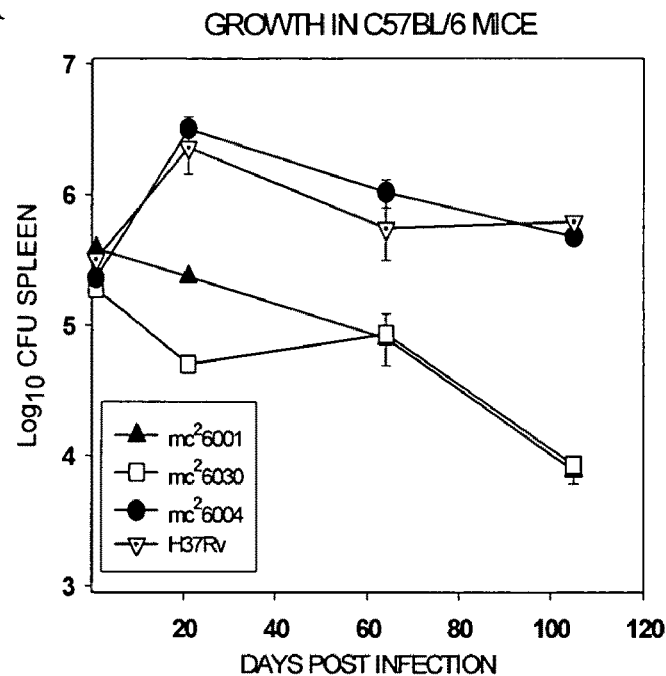
FIG. 18 shows graphs summarizing experimental results measuring growth of various strains of *M. tuberculosis* in spleen (Panel A) and lungs (Panel B) of C57BL/6 mice.
Figure 18:
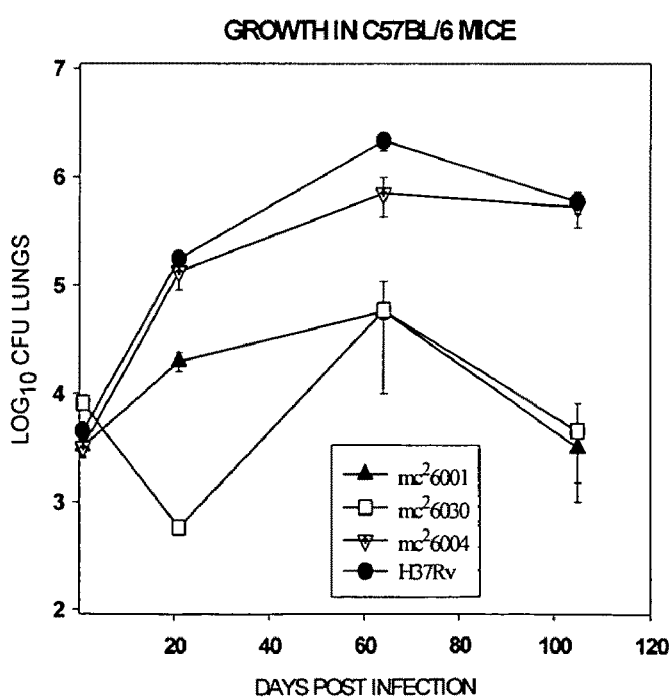

SCID mice infected with 1×10$^2$ CFU H37Rv succumbed to infection in 6 weeks, whereas the mice infected with 1×10$^6$ mc$^2$6030 survived significantly longer with more than 75% of mice surviving for more than 300 days (FIG. 17A). Bacteria isolated from mc$^2$6030-infected mice before they died were all auxotrophs, confirming that there were no revertants under in vivo conditions. In order to assess the safety of mc$^2$6030 in immunocompetent BALB/c mice, we infected mice intravenously with 1×10$^6$ mc$^2$6030 or 1×10$^6$ of wild-type H37Rv. All mice infected with H37Rv succumbed to infection by 150 days, whereas mice infected with mc$^2$6030 survived for more than 300 days (FIG. 17B). In an effort to understand the role of immune responses in controlling infection with the pantothenate mutants, we infected immunocompetent C57Bl/6 with 1×10$^6$ CFU of mc$^2$6001 (ΔRD1), mc$^2$6004 (complementing strain), mc$^2$6030 (ΔRD1ΔpanCD) or wild-type H37Rv. Mice infected with H37Rv and mc$^2$6004 showed progressive growth in all the three organs, whereas mice infected with mc$^2$6030 showed a drop in growth during the first 3 weeks in the lungs and spleen (FIG. 18). Following 3 weeks of infection, the growth pattern of both mc$^2$6001 and mc$^2$6030 were identical in the spleen and lungs. Mice immunized subcutaneously with one or two doses of mc$^2$6030 demonstrated protection against aerosol challenge with virulent *M. tuberculosis*, which was comparable to the protection afforded by BCG vaccination (Table 6). No pantothenate auxotrophs were recovered from spleen or lungs of mice at 1, 2 or 3 months following subcutaneous immunization.

TABLE 6

Bacterial burden of virulent *M. tuberculosis* in uninoculated mice and mice inoculated with BCG or one or two doses of ΔRD1ΔpanCD.

| Experimental Group | Lung CFUs (log$_{10}$) | Spleen CFUs (log10) |
|---|---|---|
| Naive | 5.99 ± 0.09 | 4.94 ± 0.06 |
| ΔRD1ΔpanCD (1 dose) sc | 5.22 ± 0.10* | 4.04 ± 0.15* |
| ΔRD1ΔpanCD (2 doses) sc | 4.86 ± 0.14** | 3.58 ± 0.11** |
| BCG (1 dose) sc | 4.79 ± 0.19** | 3.73 ± 0.27** |

*p < 0.01 relative to controls;
**p < 0.001 relative to controls

Figure 19:
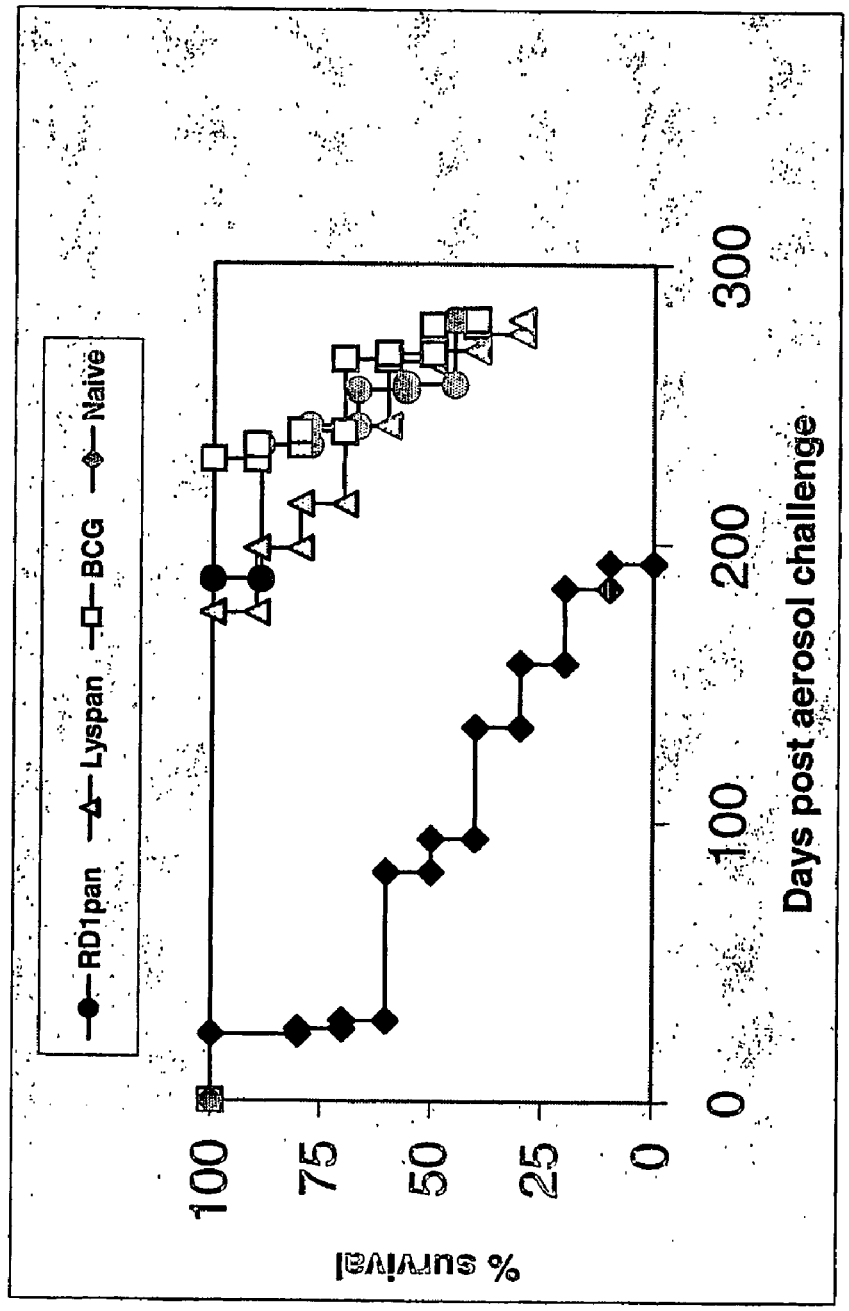
FIG. 19 is a graph summarizing experimental results establishing that immunization with mc²6020 and mc²6030 protects mice against TB as effectively as BCG. This graph shows the survival of C57Bl/6 mice challenged with virulent *M. tuberculosis* Erdman through the aerosol route three months after a single dose subcutaneous immunization with either BCG, mc²6020 (ΔlysAΔpanCD) or mc²6030 (ΔRD1ΔpanCD) and compared to non-immunized naive mice. There were 12 to 15 mice in each survival group.

Construction and characterization of *M. tuberculosis* ΔlysAΔpanCD (mc$^2$6020). A pantothenate auxotroph of *M. tuberculosis* ΔlysA was generated by specialized transduction and the strain designated mc$^2$6020. No CFU were detected on 7H11 when 5×10$^{10}$ CFU were plated, suggesting the reversion frequency to be below 10$^{-11}$. This double mutant is auxotrophic for both lysine and pantothenate. SCID mice infected with 1×10$^2$ CFU H37Rv succumbed to infection in 6 weeks, whereas the mice infected with 1×10$^6$ mc$^2$6020 survived for more than 400 days with no mortality. In order to assess the safety and growth kinetics of mc$^2$6020 in immunocompetent BALB/c mice, we infected mice intravenously with 1×10$^6$ mc$^2$6020 or 1×10$^6$ of wild-type H37Rv. All mice infected with H37Rv succumbed to infection by 150 days, whereas mice infected with mc$^2$6020 survived for more than 400 days. After 3 weeks following intravenous infection, no colonies of mc$^2$6020 could be recovered from spleen, liver or lungs of infected mice. Interestingly, mice immunized subcutaneously with one or two doses of mc$^2$6020 demonstrated protection against aerosol challenge with virulent *M. tuberculosis*, which was comparable to the protection afforded by BCG vaccination (Table 7). No pantothenate and lysine requiring auxotrophs were recovered from spleen or lungs of mice at 1, 2 or 3 months following subcutaneous immunization. Other studies established that both mc$^2$6020 and mc$^2$6030 protects the a level of protection of mice against TB equivalent to the protection afforded by BCG (FIG. 19).

TABLE 7

Bacterial burden of virulent *M. tuberculosis* in uninoculated mice and mice inoculated with BCG or one or two doses of mc$^2$6020 (ΔlysAΔpanCD) sc or one dose of mc$^2$6020 iv.

| Experimental group | Lung CFUs (log$_{10}$) | Spleen CFUs (log$_{10}$) |
|---|---|---|
| naive | 6.03 ± 0.05$^a$ | 4.84 ± 0.27 |
| BCG (1 dose) sc | 4.76 ± 0.19 *** | 3.95 ± 0.18 * |
| mc$^2$6020 (1 dose) sc | 5.05 ± 0.06 *** | 4.02 ± 0.11 * |
| mc$^2$6020 (2 doses) sc | 5.09 ± 0.05 *** | 4.06 ± 0.27 |
| mc$^2$6020 (1 dose) iv | 5.06 ± 0.11 *** | 4.00 ± 0.15 * |

$^a$Mean ± SEM
p < 0.001 = ***;
p < 0.05 = *

These data clearly demonstrate the safety and immunogenicity of these two double mutants of *M. tuberculosis* in mice.

The double deletion mutant mc$^2$6030 (ΔRD1ΔpanCD) immunizes and protects CD4$^{-/-}$ mice from aerosolized *M.*

Figure 20:
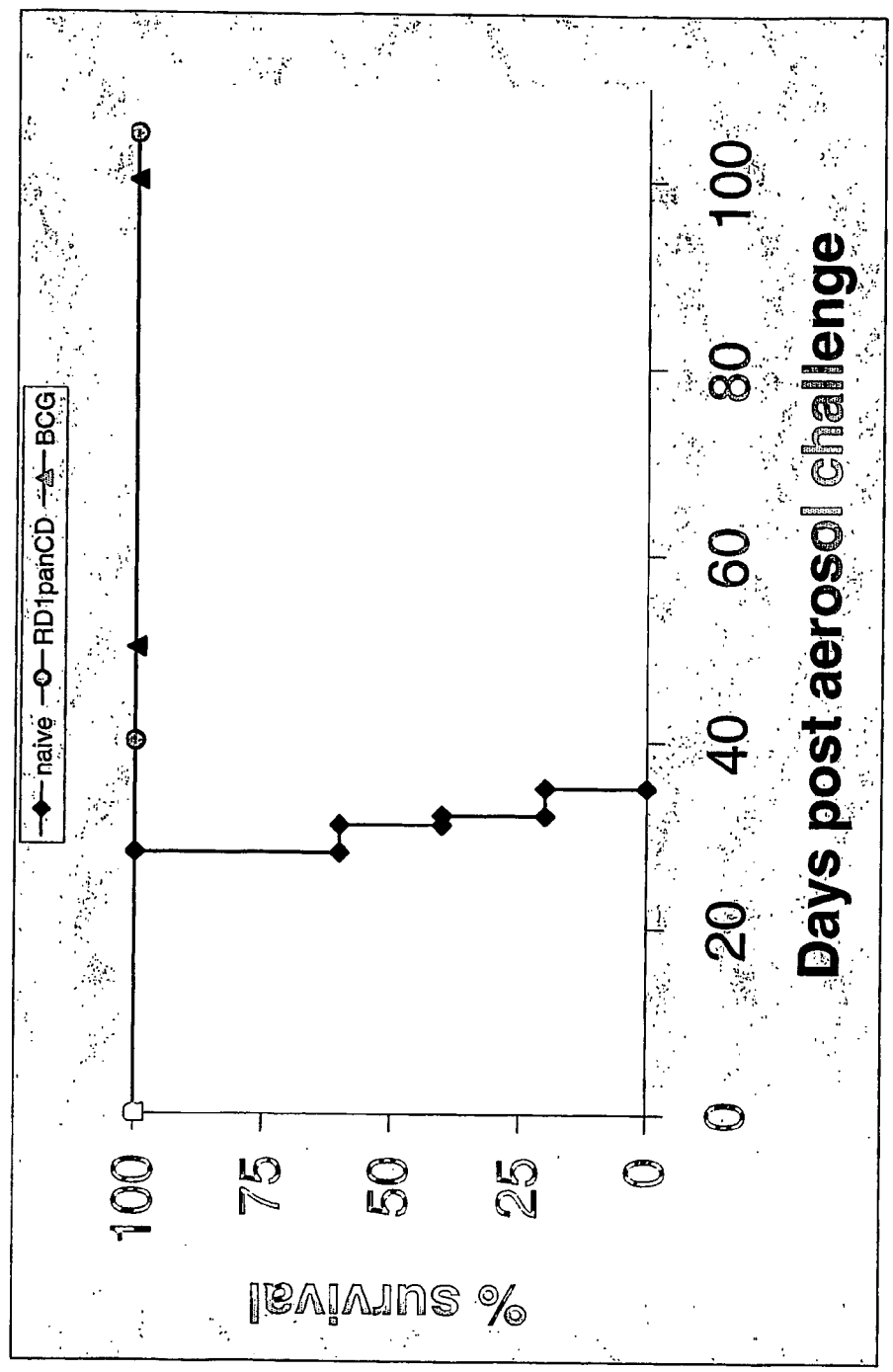
FIG. 20 is a graph summarizing experimental results establishing that immunization with mc²6030 protects CD4 deficient mice from TB. CD4⁻/⁻ mice were immunized by a single subcutaneous injection of 10⁶ CFU of either ΔRD1ΔpanCD (mc²6030) or BCG-P and three months later challenged with 100-200 CFU of virulent *M. tuberculosis* through the aerosol route and compared to non-immunized (naive) CD4⁻/⁻ controls. Each group consists of 10 mice.
Figure 21:
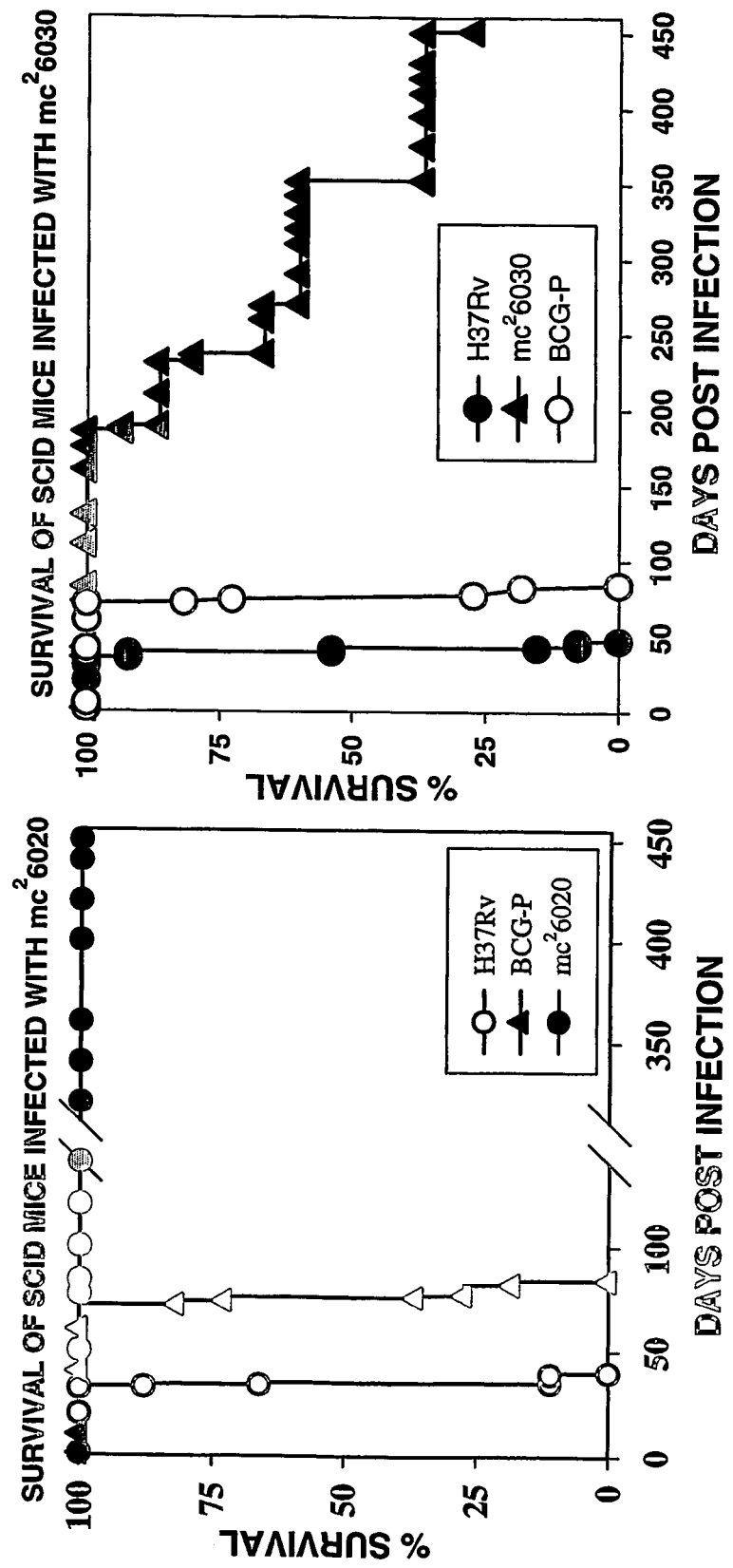
FIG. 21 shows graphs summarizing experimental results establishing that *M. tuberculosis* double deletion mutants are highly attenuated in SCID mice. A dose of 10⁵ mc²6020 or mc²6030 were intravenously inoculated into SCID mice (10 per group) and time to death assessments were performed. While the same dose of *M. tuberculosis* and BCG killed mice in 40 or 90 days, respectively, the mice infected with mc²6020 or mc²6030 survived over 400 or 250 days, respectively.

*tuberculosis* challenge. We tested the hypothesis that the attenuated double deletion mutants could protect CD4-deficient mice, a model of HIV-infected humans, from aerosolized *M. tuberculosis* challenge. The results of these tests are summarized in FIG. 20. While 100% of the non-immunized CD4$^{-/-}$ were dead by 38 days, 100% of the mice immunized with either BCG or mc$^2$6030 are alive at 120 days post challenge. After 120 days, none of the immunized mice had any outward sign of disease. The double deletion mutants were also safer than BCG in SCID mice, where all of the SCID mice died before 100 days when inoculated with BCG, 100% and 25% of the mice survived inoculation with mc$^2$6020 and mc$^2$6030, respectively (FIG. 21). This indicates that immunity against *M. tuberculosis* can be elicited in a CD4-independent manner. These results also support the notion that effective antibody or CD8-mediated vaccines to malaria and HIV could be developed in the context of these attenuated *M. tuberculosis* strains.

EXAMPLE 7

*Mycobacterum tuberculosis* RD1 panCD is Safe and Protects CD4-Deficient Mice Against *Tuberculosis* in the Absence of CD8 Cells Example Summary Tuberculosis (TB) remains a leading cause of death due to an infectious agent and is particularly devastating among HIV-infected individuals. The risk of disseminated BCG disease precludes the use of BCG vaccine in adults with known HIV infection or children with symptomatic AIDS. There is an urgent need for a safe and effective vaccine against *tuberculosis* for immunocompetent, as well as immunodeficient individuals. Here, we report that a mutant of *Mycobacterium tuberculosis* with two independent deletions, in the RD1 region and panCD genes, is severely attenuated in immunocompromised mice lacking T and B cells or mice lacking interferon-gamma and significantly safer than the BCG vaccine. A single subcutaneous immunization with the ΔRD1 ΔpanCD mutant induces significant protective immune responses that prolong the survival of immunocompetent mice following a challenge with virulent *M. tuberculosis*. As a model that reflects the loss of CD4-cells associated with HIV infection, we tested whether *M. tuberculosis* ΔRD1 ΔpanCD could immunize and protect CD4-deficient mice against aerosol challenge with virulent *M. tuberculosis*. Surprisingly, immunization with this mutant affords significantly enhanced post-challenge survival to CD4-deficient mice than BCG vaccine. Furthermore, treatment of ΔRD1 ΔpanCD vaccinated CD4$^{-/-}$ mice with anti-CD8 antibody did not eliminate the protection, suggesting the role of a novel class of CD4$^-$CD8$^-$ cells in mediating this protection. Our results highlight the feasibility of generating multiple deletion mutants of *M. tuberculosis* that are non-revertible, highly safe and yet retain the ability to induce strong protective immunity against TB in both immunocompetent and CD4-deficient mice.

Introduction

The global problem of *tuberculosis* (TB) is worsening, primarily as a result of the growing HIV pandemic (Corbett et al., 2003). TB is a leading cause of death due an infectious agent, claiming more than 2 million lives each year, with approximately 12% attributable to HIV. The global TB problem is further worsened by the emergence of multi-drug resistant strains of *Mycobacterium tuberculosis* (Pablos-Mendez et al., 1998). Clearly, novel interventions in the form of an effective vaccine are urgently needed to reduce the disease burden of TB, particularly for HIV-infected individuals.

Vaccination with bacille Calmette-Guérin (BCG), a live attenuated strain of *Mycobacterium bovis*, induces protective immunity in children against severe and fatal forms of TB (Bloom and Fine, 1994; Rodrigues et al., 1993). However, the protection afforded by BCG vaccine against the most prevalent pulmonary form of TB in adults is highly variable (0 to 80%) (Tuberculosis Prevention Trail, 1980; Fine, 1995). Although BCG has been administered to >3 billion people and has an overall excellent safety record (Lotte et al., 1988), there have been several cases of disseminated BCG disease in individuals with mutations of their IL-12, or IL-12R genes following vaccination or infection with BCG (Altare et al., 1998; Casanova et al., 1995; de Jong et al., 1998). Likewise, there have been numerous cases of disseminated BCG have been detected in vaccinated children who subsequently developed AIDS (Talbot et al., 1997; von Reyn et al., 1987; Weltman and Rose, 1993; Braun and Cauthen, 1992). Therefore, a safer and more effective vaccine than the currently used BCG vaccine is urgently needed to control TB in HIV-infected individuals.

The genetic basis for the primary attenuation of the widely used *M. bovis* derived BCG vaccine has been attributed to the loss of approximately 10 genes, named the region of difference, RD1 region (Lewis et al., 2003; Pym et al., 2002; Hsu et al., 2003). Comparative genomic studies have revealed at least 129 open reading frames to be missing from BCG strains in comparison to wild-type *M. tuberculosis* (Mahairas et al., 1996; Behr et al., 1999; Gordon et al., 1999). These missing regions may encode potential antigenic determinants that could increase the immunogenicity of a vaccine, if it were derived from an attenuated strain of *M. tuberculosis*. Several live, attenuated *M. tuberculosis* vaccine candidates have been constructed by deleting genes required for growth in mice (Hondalus et al., 2000; Jackson et al., 1999; Smith et al., 2001) and have shown to confer some degree of protection against challenge infection with virulent *M. tuberculosis*.

We had previously reported the significant safety and immunogenicity of a ΔpanCD mutant of *M. tuberculosis* in mice (Sambandamurthy et al., 2002). In an attempt to further enhance the safety of a *M. tuberculosis* derived vaccine, we deleted the panCD genes from the ΔRD1 mutant of *M. tuberculosis* that contains at least three attenuating mutations (Hsu et al., 2003). The resulting ΔRD1 ΔpanCD mutant has the safety features of two independent nonrevertible genomic deletions, which confer significant attenuation even in immunodeficient mice that lack T and B cells or mice that lack γ-interferon. In addition, the ΔRD1 ΔpanCD mutant undergoes limited replication in vivo; and thus confers significant long-term protection and survival in mice following a single dose vaccination. We also demonstrate that this attenuated TB vaccine is significantly better than BCG in prolonging the survival of CD4-deficient mice following an aerosol challenge with virulent *M. tuberculosis* and the protective immunity induced in these immunocompromised mice is largely mediated by a novel class of CD4$^-$CD8$^-$ cells.

Materials and Methods

Media and Strains. *M. tuberculosis* H37Rv, *M. tuberculosis* Erdman and *M. bovis* BCG Pasteur were obtained from the Trudeau Culture Collection (Saranac Lake, N.Y.) and cultured as described earlier (Sambandamurthy et al., 2002). When required, pantothenate (24 μg/ml) or hygromycin (50 μg/ml) was added. Stock strains were grown in Middlebrook 7H9 broth in roller bottles and harvested in mid-logarithmic growth phase, before being stored in 1 ml vials at −70° C.

Figure 22:
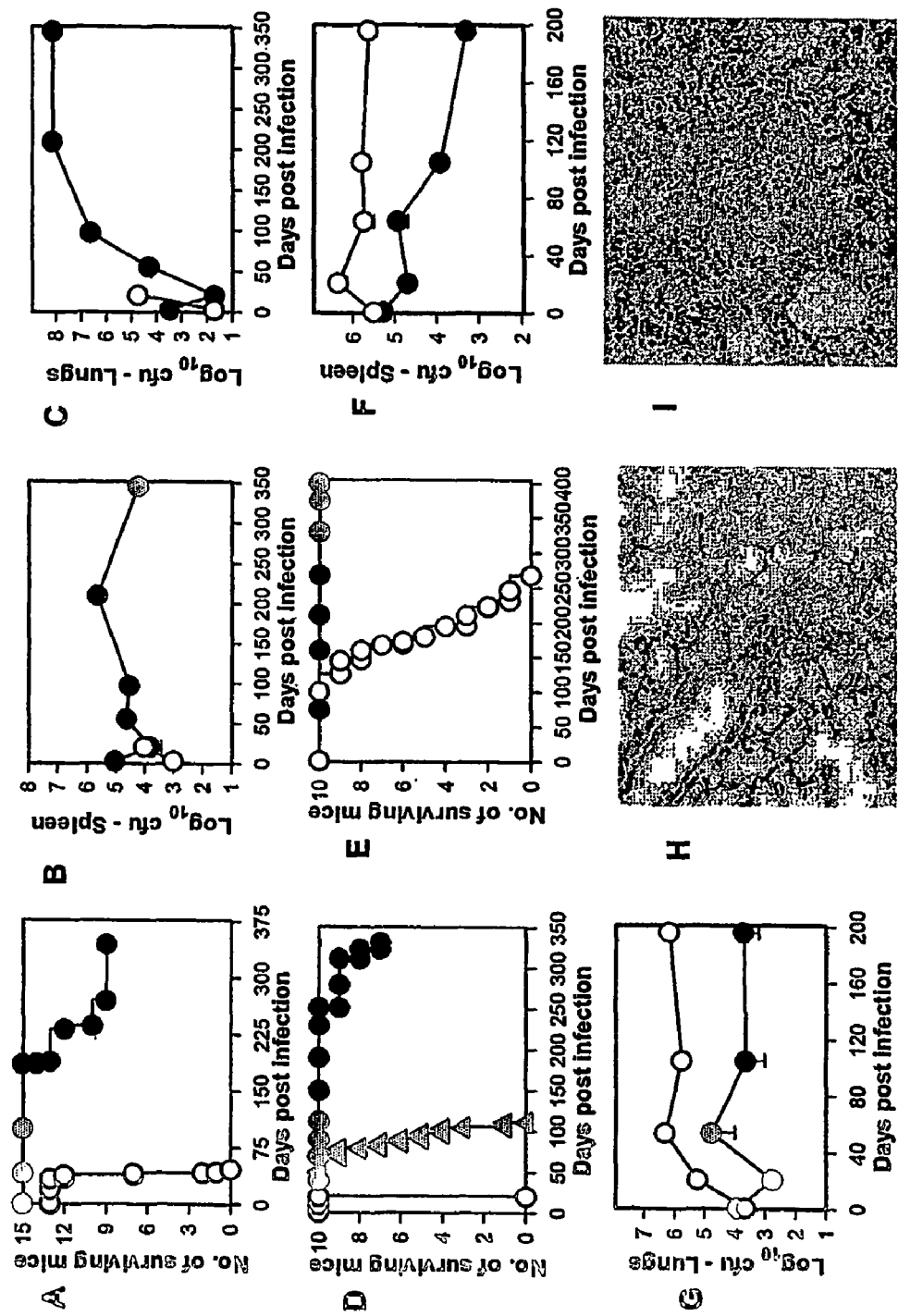
FIGS. 22A-22I are graphs and micrographs of experimental results showing that mc²6030 is severely attenuated in immunocompromised mice. A. Survival of SCID mice infected intravenously with 10² CFUs of H37Rv (○) or 10⁵ CFUs of mc²6030 (●). B, C. Bacterial numbers in the spleen (B), lungs (C), and of H37Rv (○) or mc²6030 (●) infected SCID mice. The results represent means±standard errors of four to five mice per group. D. Survival of gamma interferon gene-disrupted (GKO) C57BL/6 mice (n=10 mice) infected intravenously with 10⁵ CFUs of H37Rv (0) or mc²6030 mutant (●) or *M. bovis* BCG-P (▲). E. Survival of immunocompetent C57BL/6 mice (n=10 mice) infected intravenously with 106 CFUs of H37Rv (○) or mc²6030 (●). F, G. Bacterial numbers in spleen (E) and lungs (G) of C57BL/6 mice infected intravenously with H37Rv (○) or mc²6030 (●). The results represent means±standard errors of four to five mice per group. H. Mild perivascular, lymphocytic infiltrates caused by strain mc²6030 in C57BL/6 mice at 3 weeks post-infection. I. Severe granulomatous pneumonia in the lungs of C57BL/6 mice infected with H37Rv at 3 weeks post-infection.
Figure 23:
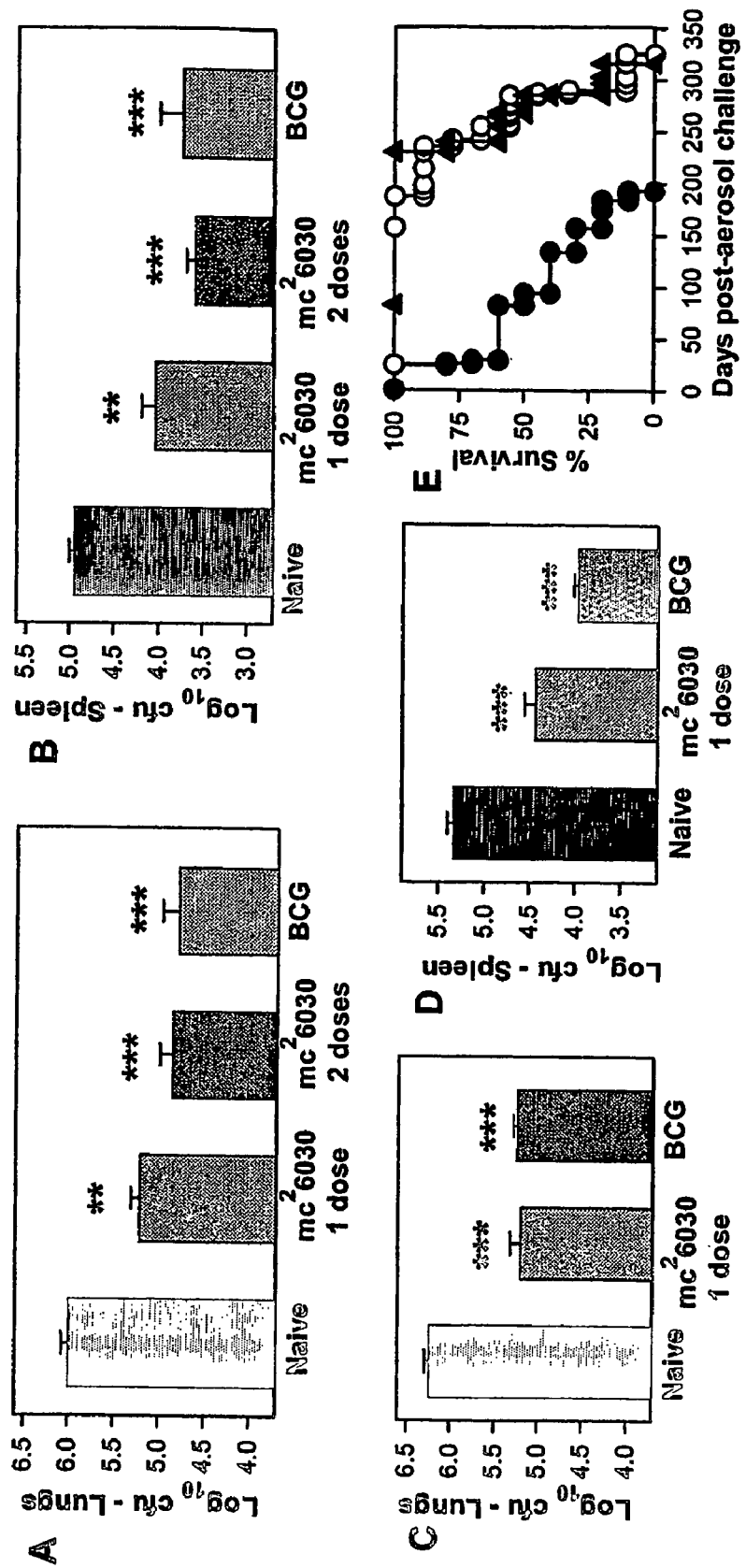
FIGS. 23A-23E are graphs of experimental results showing that vaccination with mc²6030 induces both short-term and long-term protection in C57BL/6 mice. A, B. Immunocompetent C57BL/6 mice were immunized subcutaneously (s.c) with mc²6030 or BCG-P and challenged with virulent *M. tuberculosis* Erdman through the aerosol route at 3 months after the initial immunization. The CFU numbers reflect the bacterial burden at 28 days post-aerosol challenge in the lungs and spleen of infected mice. C, D. Immunocompetent C57BL/6 mice were immunized subcutaneously (s.c) with mc²6030 or BCG-P and challenged with virulent *M. tuberculosis* Erdman through the aerosol route at 8 months after the initial immunization. The CFU numbers reflect the bacterial burden at 28 days post-aerosol challenge in the lungs and spleen of infected mice. The results represent means±standard errors of five mice per group. P<0.01, *P<0.001 indicate statistical differences between the experimental and unvaccinated control groups. E. Survival of immunocompetent C57BL/6 mice (n=10 mice) immunized subcutaneously with a single dose of mc²6030 (●) or BCG-P (▲) and challenged 3 months later with virulent *M. tuberculosis* Erdman through the aerosol route. Unvaccinated mice served as naive controls (○).

Construction of *M. tuberculosis* ΔRD1 ΔpanCD (mc26030) deletion mutant. Specialized transduction was employed to disrupt the chromosomal copy of the panCD genes from the unmarked *M. tuberculosis* ΔRD1 mutant (Hsu et al., 2003). The panCD and RD1 deletions were confirmed using PCR and Southern blotting as described earlier (Hsu et al., 2003; Sambandamurthy et al., 2002).

Animal infections. C57BL/6, BALB/c, BALB/c SCID, C57BL/6 GKO (6-8 weeks old) were purchased from Jackson Laboratories and were infected intravenously through the lateral tail vein. For time-to-death and mouse organ CFU assays, BALB/c SCID mice were infected intravenously with $10^2$ CFUs of *M. tuberculosis* H37Rv or $10^5$ CFUs of $mc^2$6030. For GKO survival experiments, mice were infected intravenously with $10^5$ CFUs of *M. tuberculosis* H37Rv, BCG-P or the $mc^2$6030 mutant. For mouse organ CFU assays, C57BL/6 mice were infected with $10^6$ CFUs of *M. tuberculosis* H37Rv or the $mc^2$6030 mutant. At appropriate time points, groups of 4 or 5 mice were sacrificed and the bacterial burden estimated as described earlier (Sambandamurthy et al., 2002). The survival data and the CFU results were statistically evaluated using either one-way analysis of variance or unpaired t-test analyses provided by the GraphPad InStat program. Pathologic examination was performed on tissues fixed in 10% buffered formalin. All animals were maintained in accordance with protocols approved by the Albert Einstein College of Medicine and the Center for Biologics Evaluation and Research Institutional Animal Care and Use Committee.

Vaccination Studies. Groups of C57BL/6 mice (5 mice per group) were vaccinated subcutaneously, either once or twice (6 weeks apart), with $10^6$ CFUs of $mc^2$6030. Control mice were vaccinated subcutaneously with $10^6$ CFUs of *M. bovis* BCG-Pasteur. At either 3 or 8 months after the initial immunization with $mc^2$6030 or BCG, the mice were aerogenically challenged with approximately 100-200 CFUs of *M. tuberculosis* Erdman strain. At 28 days following aerosol challenge, the challenged mice were sacrificed and the bacterial numbers in the lung and spleen were enumerated as described earlier (Sambandamurthy et al., 2002).

For immunization studies in $CD4^{-/-}$ mice (Jackson Laboratories), mice were vaccinated subcutaneously with a single dose of $10^6$ CFUs of $mc^2$6030 or BCG-P and challenged three months later through the aerosol route. For the survival studies, 5 to 6 mice per group were maintained until they became moribund and had to be euthanized. Five mice were sacrificed after 24 hours to confirm the size of the challenge dose following the aerosol challenge.

For the CD8 depletion studies, $CD4^4$ mice were immunized with a single subcutaneous dose of $mc^2$6030 and then treated intraperitoneally with anti-CD8 monoclonal antibody (clone 243, Harlan Bioproducts, Indianapolis Ind.) at two days before, the day of the tuberculous challenge, and then twice per week (0.2 mg/ml per dose) until the mice were sacrificed. The effectiveness of the anti-CD8 antibody treatment was confirmed by flow cytometry after staining peripheral blood and lung lymphocytes with Cy-Chrome-conjugated rat anti-mouse CD8a (ly-2) monoclonal antibody (Pharmingen, San Diego, Calif.).

To assess the role of IFN-γ in mediating protection, GKO mice (n=10) were vaccinated with $10^6$ CFU of $mc^2$6030 or BCG-P and challenged three months later through the aerosol route and followed for survival.

Results $mc^2$6030 is highly attenuated in immunodeficient mice. In an attempt to develop a safe and effective vaccine strain, the panCD genes (Sambandamurthy et al., 2002) were deleted from an unmarked ΔRD1 mutant of *M. tuberculosis* using specialized transduction (Bardarov et al., 2002). The deletions in the RD1 region and panCD genes were confirmed using PCR and Southern blotting (data not shown). Strain $mc^2$6030 is auxotrophic for pantothenate; no revertants were recovered when $10^{11}$ CFU of $mc^2$6030 strain were plated on minimal media, demonstrating the mutations to be highly stable and non-revertible.

An important pre-requisite for any live attenuated vaccine is their safe use even in immunodeficient hosts. To assess the attenuation of this mutant, severe combined immunodeficient (SCID) mice, a highly stringent model for safety, were infected intravenously with H37Rv or $mc^2$6030. Mice infected with $10^2$ CFU of *M. tuberculosis* H37Rv strain died within 4 weeks post-infection. Interestingly, 60% of SCID mice infected with $10^5$ CFU of $mc^2$6030 survived for over 350 days (FIG. 22A). Mice infected with H37Rv showed a rapid increase in bacterial numbers in the lungs, spleen and liver by 3 weeks. In contrast, the bacterial numbers in the spleen of $mc^2$6030-infected mice remained relatively constant throughout the course of infection (FIG. 22B). Bacterial numbers in the lungs of $mc^2$6030-infected SCID mice showed a decrease in the first 3 weeks of infection, but gradually increased to reach $10^8$ CFUs by 350 days (FIG. 22C). The bacterial titers were constant in the liver throughout the course of infection except for a sharp decline at 3 weeks (data not shown).

Overwhelming evidence from humans and animal models has implicated IFN-γ to be a key cytokine in the control of *M. tuberculosis* infection (Flynn and Chan, 2001). IFN-γ knockout (GKO) mice are extremely sensitive to tuberculous infection (Cooper et al., 1993; Flynn et al., 1993) and individuals defective in genes for IFN-γ receptors have increased susceptibility to disseminated mycobacterial disease (Ottenhoff et al., 1998). As an additional assessment of the safety of this attenuated mutant, GKO mice were infected intravenously with $10^5$ CFU of *M. tuberculosis* H37Rv, BCG Pasteur (BCG-P) or $mc^2$6030. All of the GKO mice infected with H37Rv (mean survival time, MST, 21 days) or BCG-P (MST, 93 days) succumbed to the tuberculous infection within 4 months, whereas >60% of mice infected with $mc^2$6030 were alive at 335 days (FIG. 22*d*). The extreme susceptibility of immunocompromised mice to *M. tuberculosis* and BCG infections is consistent with data from previous studies using SCID (Sambandamurthy et al., 2002; Weber et al., 2000) and GKO mice (Dalton et al., 1993). Overall, our data indicate that $mc^2$6030 is significantly more attenuated and less virulent in SCID and GKO mice than the widely used BCG vaccine strain.

$mc^2$6030 undergoes limited replication in mice. To evaluate the effect of the multiple mutations in strain $mc^2$6030 on bacterial growth in vivo, immunocompetent BALB/c or C57BL/6 mice were infected intravenously. All BALB/c mice infected with $10^5$ CFU of H37Rv succumbed to the resulting infection by 168 days (MST=134 days). In contrast, all mice infected with $10^5$ CFU of $mc^2$6030 survived for over 400 days (data not shown). Similarly, C57BL/6 mice infected with $10^6$ CFU of H37Rv succumbed to infection by 260 days (MST=196 days). All mice infected with $10^6$ CFUs of $mc^2$6030 survived over 400 days post-infection (FIG. 22E). Bacteriological culture results generally showed a decline in the numbers of H37Rv and $mc^2$6030 organisms in the spleen (FIG. 22F) and liver (data not shown) of C57BL/6 mice after infection. Interestingly, the pulmonary bacterial CFU numbers for both the virulent H37Rv strain and the attenuated mutant reached a constant level at 3 months post-infection (FIG. 22G). Importantly, the H37Rv CFU values were at least 100-fold higher than the mc²6030 CFUs in all organs tested at 200 days after the infection.

Figure 24:
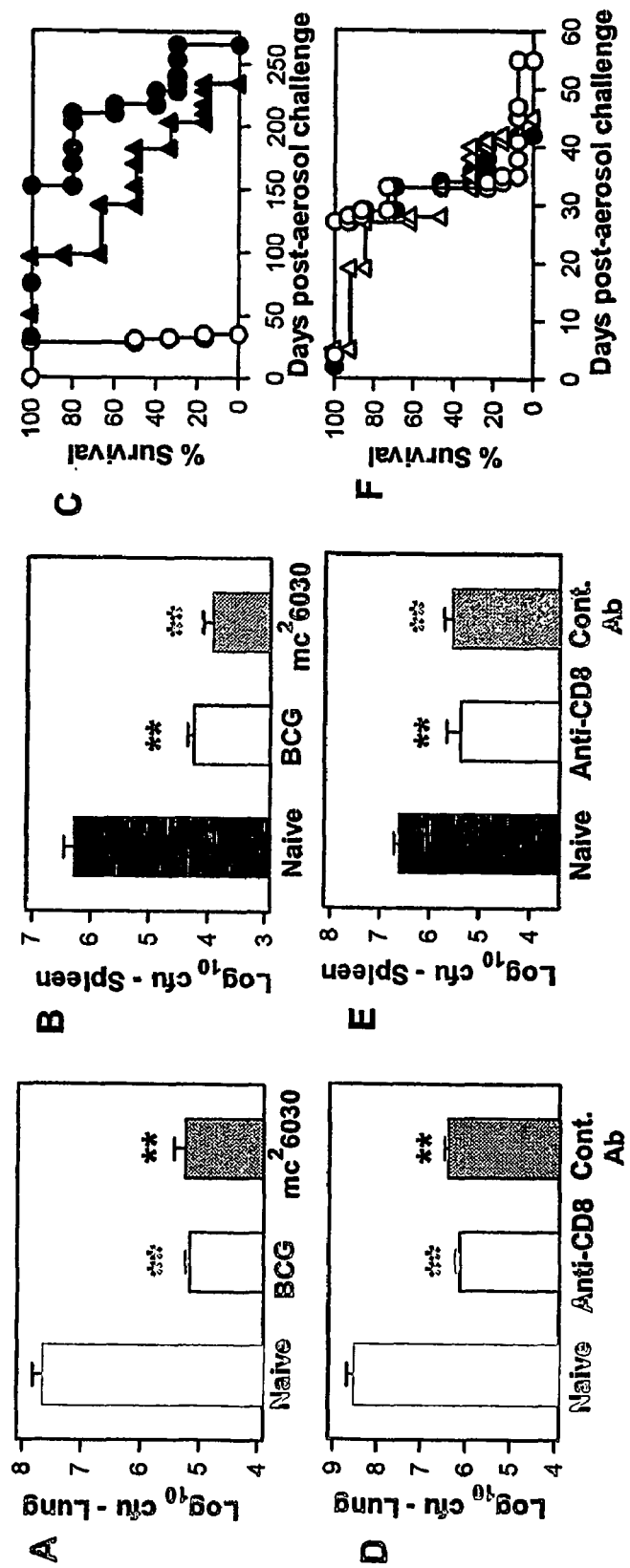
FIGS. 24A-24F are graphs of experimental results showing that vaccination with mc²6030 protects and confers greater survival advantage to CD4$^{-/-}$ mice from tuberculous challenge. A, B. Protection induced by a single dose of mc²6030 in CD4-deficient mice following aerosol challenge with virulent *M. tuberculosis* Erdman. The CFU numbers reflect the bacterial burden at 28 days post-aerosol challenge in the lungs (a) and spleen (b) from 5 mice per group. **P<0.001 indicate statistical differences between the experimental and unvaccinated control groups. C. Survival of CD4$^{-/-}$ mice (n=5 or 6 mice) immunized subcutaneously with a single dose of mc²6030 (●) or BCG-P (▲) and challenged 3 months later with virulent *M. tuberculosis* Erdman through the aerosol route. Unvaccinated mice served as naive controls (○). D, E. Treatment of mc²6030-vaccinated CD4$^{-/-}$ mice with anti-CD8 antibody does not abolish the protection seen in mc²6030-vaccinated control antibody treated CD4$^{-/-}$ mice. The CFU numbers reflect the bacterial burden at 28 days post-aerosol challenge in the lungs (D) and spleen (E) from 5 mice per group. **P<0.001 indicate statistical differences between the experimental and unvaccinated control groups. F. Survival of vaccinated GKO mice following an aerosol challenge with virulent *M. tuberculosis*.
Figure 25:
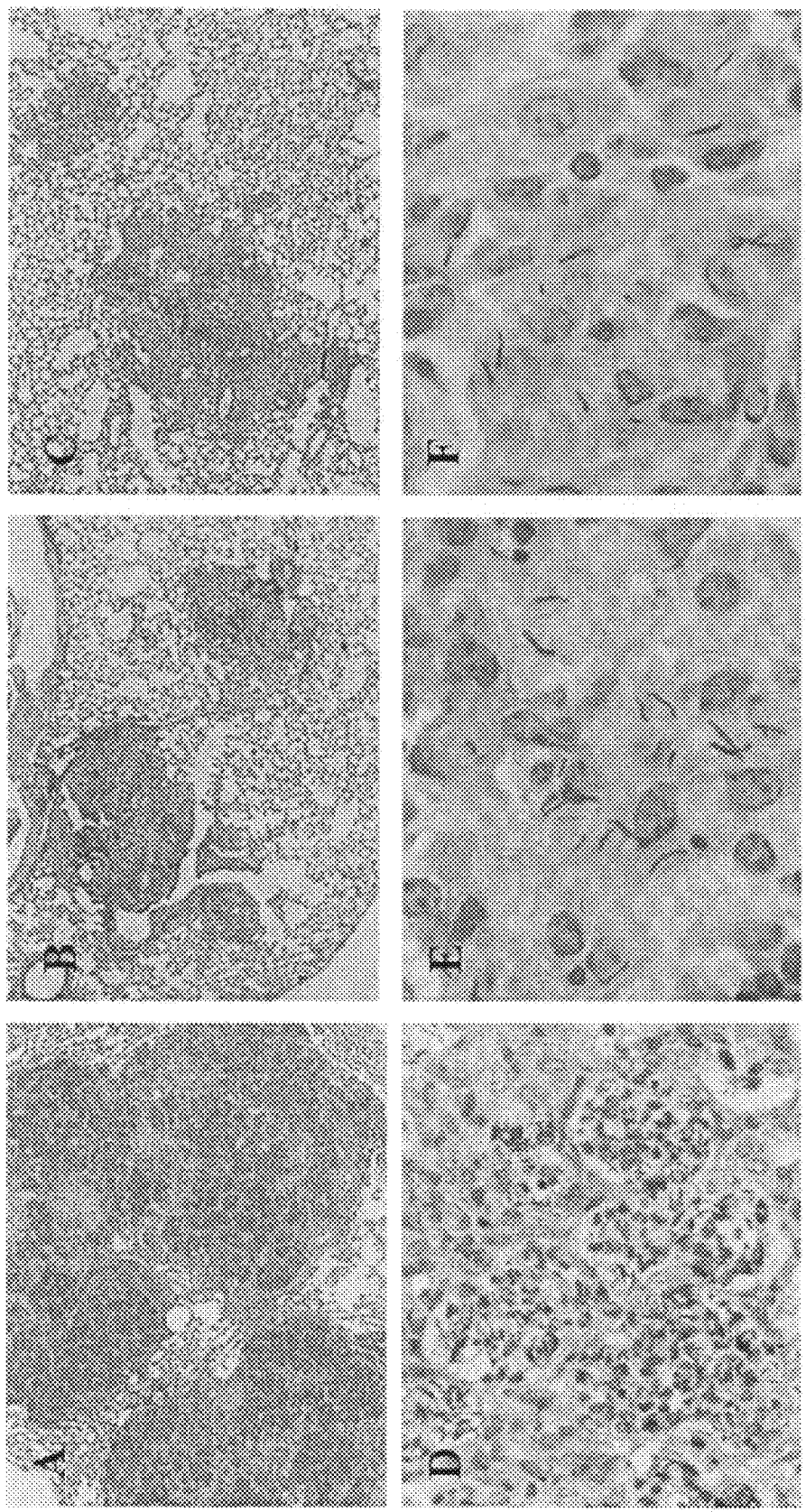
FIGS. 25A-25F are micrographs of experimental results showing that. mc²6030 vaccinated CD4$^{-/-}$ mice display improved lung pathology following challenge with virulent *M. tuberculosis*. A. Severe pneumonia in lung of unvaccinated mice at 28 days post-aerosol challenge, with D, large numbers of *M. tuberculosis* Erdman organisms demonstrated by acid-fast stain. B. Lung from mouse vaccinate with mc²6030 showing milder multifocal areas of pneumonia composed of macrophages and numerous lymphocytes, with E, lower number of *M. tuberculosis* Erdman organisms indicating protection following immunization. C. BCG vaccinated mouse. Similar localized areas of pneumonia adjacent to the airways post-aerosol challenge and F, reduced numbers of acid-fast organisms similar to mc²6030 vaccinated mice.

Histopathological examination of organs from infected mice confirmed the marked attenuation of the deletion mutant. At 3 weeks post-infection, an intravenous injection of mc²6030 (FIG. 22H) had caused only rare, mild perivascular, lymphocytic infiltrates. The spleens were slightly enlarged with mononuclear cell infiltration in the red pulp. Also, multifocal, mild infiltrations of macrophages and neutrophils were seen in the liver and no acid-fast bacilli were detected. This contrasted with the severe pneumonia (FIG. 22I), markedly enlarged spleens, severe diffuse granulomatous hepatitis, and the overwhelming bacterial burden seen in mice infected with the H37Rv strain.

mc²6030 induces short and long-term protection in immunocompetent mice. Having assessed the safety and growth kinetics of mc²6030 in both immunodeficient and immunocompetent mice, we evaluated the protective immune responses induced by this attenuated strain. As a test of its vaccine potential, C57BL/6 mice were immunized subcutaneously with $10^6$ CFUs of $mc^2$6030 and then were challenged 3 months later with a low dose of virulent *M. tuberculosis* Erdman by the aerosol route. Following subcutaneous immunization, the immunizing $mc^2$6030 mutant bacteria could not be cultured from the spleens or lungs of mice at 8 and 12 weeks postvaccination. At 28 days post-aerosol challenge, mice that were immunized 3 months earlier with a single dose of $mc^2$6030 showed a significant reduction in the lung ($P<0.01$) and spleen ($P<0.01$) bacterial CFU values as compared to naïve mice. Consistent with published results, mice vaccinated with $10^6$ CFUs of BCG showed similar CFU reductions in the lungs ($P<0.001$) and spleen ($P<0.001$) as compared to the naïve controls (FIG. 23A,B).

In order to assess the duration and persistence of the memory immune response, vaccinated and control mice were challenged through the aerosol route 8 months after a single dose vaccination. In the naïve controls at four weeks post-challenge, the bacterial numbers increased dramatically in the lung and substantial dissemination and growth in the spleen were also observed. Strikingly, mice vaccinated with a single dose of $mc^2$6030 or BCG-P displayed statistically significant reduction in bacterial numbers in the lungs ($P<0.001$) and spleen ($P<0.001$) relative to naïve controls (FIG. 23C D). Our data clearly demonstrate that a single dose of $mc^2$6030 induces a potent and long-lasting protective immune response that is effective in controlling a virulent *M. tuberculosis* challenge in the lungs and spleen of mice even after 8 months following the primary immunization.

Another relevant measure of vaccine effectiveness is the relative survival periods for immunized mice following a challenge with virulent organisms (33). To evaluate whether vaccination with $mc^2$6030 increased mean survival times, C57BL/6 mice that had been immunized subcutaneously with a single dose of $mc^2$6030 (or BCG-P) were challenged 3 months later with virulent *M. tuberculosis* Erdman by the aerosol route and followed for survival. All of the unvaccinated mice succumbed to the tuberculous infection (MST=95±22 days) following the aerosol challenge. In contrast, the survival periods of mice vaccinated with either $mc^2$6030 (MST, 267±14 days) or BCG-P (MST, 268±16 days) were significantly extended ($P<0.001$) relative to naïve mice (FIG. 23*e*).

$mc^2$6030 protects CD4-deficient mice significantly better than BCG against anaerosolized TB challenge. Tuberculosis remains the largest attributable cause of death in HIV-infected individuals (Whalen et al., 2000). HIV infection leads to a loss of $CD4^+$T cells and previous studies have demonstrated that mice deficient in $CD4^+$T cells are highly susceptible to *M. bovis* BCG (Ladel et al., 1995) and *M. tuberculosis* infection (Mogues et al., 2001; Caruso et al., 1999). Since BCG vaccination is contraindicated in HIV-infected individuals, we wanted to test if the more attenuated strain, $mc^2$6030, could protect CD4-deficient mice from experimental tuberculosis. CD4-deficient mice were vaccinated subcutaneously with a single dose of $10^6$ CFUs of either $mc^2$6030 or BCG-P and then aerogenically challenged with 100-200 CFUs of *M. tuberculosis* Erdman three months later. At 28 days post-aerosol challenge, the bacterial burden in the lungs ($P<0.001$) and spleen ($P<0.001$) of the $mc^2$6030 and BCG-P vaccinated mice was decreased by greater than 99% (>2 log CFU) relative to naïve controls (FIG. 24A,B).

To further evaluate the long-lived protection induced by $mc^2$6030, $CD4^{-/-}$ mice were vaccinated, challenged 3 months later with virulent *M. tuberculosis* Erdman through the aerosol route, and followed for survival. All of the naïve mice died within 29 days (MST=27±2 days) of the low dose tuberculous aerogenic challenge (FIG. 24C). Strikingly, the mean survival time for the $CD4^{-/-}$ mice vaccinated with a single dose of $mc^2$6030 was 214±18 days, a nearly eight-fold extension of the survival period compared to naïves. In contrast, the BCG vaccinated mice survived 158±23 days. The 56-day extension of the MST for the $mc^2$6030-immunized mice relative to BCG vaccinated animals represented a significantly improved outcome ($P<0.05$) for $CD4^{-/-}$ mice immunized with the *M. tuberculosis* mutant strain.

Histologically, significant differences were observed between the vaccinated groups and naïve $CD4^{-/-}$ controls. The unvaccinated mice developed severe lung lesions with multiple large inflammatory nodules; some coalescing and spreading to areas of extensive diffuse pneumonia. The inflammatory response consisted of macrophages, numerous neutrophils, accompanied by low numbers of lymphocytes. There were large numbers of acid-fast organisms in the lesions (FIG. 25A,D). In contrast, mice vaccinated with $mc^2$6030 (FIGS. 25B,E) or BCG (FIG. 25C,F) showed reduced severity of the lung lesions. These mice showed scattered distinct lesions, adjacent to airways and localized, which remained smaller in diameter than in unvaccinated mice. These multifocal areas were composed of macrophages and numerous lymphocytes. There was a marked reduction in the numbers of acid-fast organisms compared to naïve controls.

The ability of $mc^2$6030-vaccinated $CD4^{-/-}$ mice to control the tuberculous challenge suggests the potential role of $CD8^+$T cells in mediating this protection. In order to directly demonstrate the role of $CD8^+$T cells in this protective response, $CD4^{-/-}$ mice that were vaccinated with $mc^2$6030 were treated with anti-CD8 monoclonal antibody and subsequently challenged with virulent *M. tuberculosis* through the aerosol route. Flow cytometric analysis showed that the anti-CD8 antibody treatment had depleted >99% of $CD8^+$T cells from the lungs and peripheral blood. Surprisingly, repeated injections of the anti-CD8 antibody did not reduce the vaccine-mediated protective immune response. At 28 days post-aerosol challenge, the bacterial burdens in the lungs and spleens of the anti-CD8 antibody-treated immunized $CD4^{-/-}$ mice and nontreated vaccinated mice were similar; significant reductions in the pulmonary and splenic bacterial CFUs, relative to nonimmunized controls (>2 $\log_{10}$ in the lungs and >1 $\log_{10}$ in the spleen) were detected for each vaccine group (FIG. 24D,E).

To examine the role of IFN-γ in mediating the anti-tuberculous immunity evoked by the mutant *M. tuberculosis* strain, GKO mice were vaccinated with mc²6030 or BCG-P and challenged with *M. tuberculosis*. Immunization of GKO mice with mc²6030 or BCG-P did not significantly increase the survival period in comparison to unvaccinated controls with all mice in each of the three groups succumbing to the resulting infection within 30 days. Interestingly, 4 out of 10 BCG-vaccinated GKO mice died of disseminated BCG infection even before the aerosol challenge (FIG. 24F).

Discussion

Vaccination remains the most cost-effective and proven strategy to protect mankind against infectious agents (Bloom, 1989). The eradication of smallpox and the near elimination of poliomyelitis demonstrate the potential of one class of vaccines, the live attenuated vaccines. However, a major obstacle to the development of these vaccines is the difficulty in achieving a satisfactory level of attenuation without severely compromising the immunogenicity of the vaccine strain. Recent advances in the molecular biology of mycobacteria have been used to construct several attenuated mutants of *M. tuberculosis* as candidates for a vaccine (Hondalus et al., 2000; Jackson et al., 1999; Smith et al., 2001). An *M. tuberculosis*-derived vaccine may be more efficacious and induce a qualitatively better protective immune response than an *M. bovis*-derived BCG vaccine because the immunogenicity of BCG seem to have declined following extensive passage over the years (Behr and Small, 1997) and *M. tuberculosis* mutants should express an antigenic profile that is nearly identical to virulent TB.

The deletion of the RD1 region (the primary attenuating deletion in all BCG vaccine strains) from *M. tuberculosis* leads to attenuation of the resulting mutant strain (Lewis et al., 2003; Hsu et al., 2003). However, that strain is relatively more virulent than the currently used BCG vaccine in immunodeficient SCID mice. In contrast, a multiple deletion mutant of *M. tuberculosis* ($mc^2$6030) harboring deletions in the RD1 region and the panCD genes is severely attenuated in SCID mice. This mutant is considerably less virulent than the single ΔRD1 or ΔpanCD *M. tuberculosis* mutants or BCG in this mouse model. Interestingly, our data also show that the $mc^2$6030 mutant is markedly more attenuated than the widely used BCG vaccine in mice lacking IFN-γ.

While live strains must be attenuated, they should retain their capacity to undergo limited in vivo replication (McKenney et al., 1999; Kanai and Yanagisawa, 1955; Brant et al., 2002). The failure of earlier auxotrophs of *M. tuberculosis* to induce a potent protective immune response could be due to insufficient in vivo replication. The capacity of $mc^2$6030 mutant to undergo limited replication without causing detrimental pathology in the tissues of infected wild-type mice likely contributes to its ability to generate long-term immunity in mice. The hallmark of immunological memory and vaccination is the ability to mount an accelerated response to reinfection, which is achieved by the generation of long-lived memory T cells. The induction and long-term maintenance of cellular immune responses is the primary goal of a vaccine for an intracellular pathogen such as *Mycobacterium tuberculosis* (Seder and Hill, 2000). For the $mc^2$6030 strain, the protective response seen at 8 months following a single immunization reflects the generation of long-term memory response. An additional proof of this induction of immunological memory was demonstrated in the survival studies; mice vaccinated with $mc^2$6030 survived significantly longer than control mice following a tuberculous challenge.

HIV-infection is a major risk factor for both primary and reactivational disease with *M. tuberculosis* in humans. The annual risk of developing TB in individuals coinfected with TB and HIV is 10%, while immunocompetent individuals have only a 10% lifetime risk of developing disease following infection. Therefore, HIV-1 infected individuals remain a critical cohort of patients suitable for vaccination. However, candidate vaccines may not be sufficiently immunogenic to stimulate protective immunity in potentially immunodeficient HIV-1 infected patients with impaired or defective $CD4^+$ T cell responses. To test this principle, we explored whether immunedeficient mice lacking $CD4^+$ T cells could be protected against TB by vaccination with a safe mutant of *M. tuberculosis*. Interestingly, our study clearly demonstrates the ability of a single dose vaccination with $mc^2$6030 to confer significant protection in $CD4^{-/-}$ mice following an aerosol challenge with virulent *M. tuberculosis*. Reduced organ bacterial burdens, prolonged survival and a milder pulmonary histopathology were seen in vaccinated mice relative to naïve mice lacking $CD4^+$ T cells. Importantly, the $mc^2$6030 vaccinated $CD4^{-/-}$ mice survived significantly longer (56 days) post-challenge than BCG-vaccinated animals. The immunogenicty of this mutant and its reduced virulence likely contribute to the improved outcome in these immunocompromised mice. Overall, these data strongly suggest that further testing of this attenuated *M. tuberculosis* strain in other immunocompromised models is warranted with a goal of developing an effective TB vaccine in HIV-1 infected individuals.

The biological basis for the enhanced effectiveness of the $mc^2$6030 strain in mice lacking $CD4^+$ T cells has not been completely elucidated. Clearly, the specific immune mechanisms associated with protection after vaccination and challenge in $CD4^+$ deficient mice are of substantial interest because several studies have suggested that $CD4^+$ T cells are absolutely required to generate anti-*tuberculosis* protective immunity (Flynn and Chan, 2001). Since $CD8^+$ T cells have been shown to play an important role in the control of acute *tuberculosis* (Behar et al., 1999; Sousa et al., 2000; Serbina and Flynn, 2001) and persistent infection (van Pinxteren et al., 2000b), we hypothesized that CD8 cells mediated the protective immunity generated by vaccination of $CD4^{-/-}$ mice with the $mc^2$6030 strain. Although several studies have demonstrated that $CD4^+$ T cell help is important in the activation and differentiation of naïve $CD8^+$ T cells into cytotoxic effector cells (Cardin et al., 1996; van Herrath et al., 1996; Wild et al., 1999), recent evidence suggests that vaccine immunity can be generated in the absence of $CD4^+$ T cells (Buller et al., 1987; Stevenson et al., 1998; Wuthrich et al., 2003) and $CD8^+$ T cells can provide self-help when they are present at a sufficiently high precursor frequency (Wang et al., 2001; Mintern et al., 2002'). Consistent with this premise, potent CD8 mediated anti-mycobacterial protective immunity was generated following immunization with a DNA vaccine cocktail in CD4-deficient mice (Steven Derrick and Sheldon Morris, Infection and Immunity, in press). Surprisingly, treatment of vaccinated mice with an anti-CD8 antibody did not reduce the protective immune response in $CD4^{-/-}$ mice induced by immunization with the *M. tuberculosis* mutant. This result suggests that $CD4^-CD8^-$ cells may contribute to the anti-tuberculous protection. These anti-CD8 antibody data are consistent with the previously described role of double-negative T cells in protecting against infections with intracellular pathogens. In a *Listeria* model, Dunn and North showed the resolution of primary listeriosis and acquired resistance to secondary infection to be predominantly mediated by double-negative T cells (Dunn and North, 1991). More recently, Cowley and Elkins reported that secondary immunity to the *Francisella tularensis* live vaccine strain was partially mediated by a unique $CD4^-CD8^-$ T cell population (Cowley and Elkins, 2003). Further studies are currently in progress to directly determine whether double-negative T cells are mediating the ΔRD1 ΔpanCD vaccine strain-induced protective immunity in CD4-deficient mice and whether CD4⁻CD8⁻ T cells are generally involved in the protective responses elicited by live attenuated strains against intracellular pathogens.

Overall, our results demonstrate that it is possible to generate two independent unlinked deletions, each containing multiple attenuating mutations into *M. tuberculosis* to generate a safe mutant that can remain immunogenic and provide protective immunity against airborne infection with virulent *M. tuberculosis* in mice. The protection and safety data from immunocompromised and immunocompetent mice and the lack of reversion make this multiple deletion mutant a viable vaccine candidate for humans. The numerous advantages of BCG, i.e., affordability, safety, ability to be used in newborns, and its use as a recombinant vaccine delivery vector should be also applicable to the highly attenuated mc²6030 candidate. Since the mc²6030 strain is more attenuated than BCG and yet is more protective in immunocompromised mice, the evaluation of the mc²6030 mutant as a vaccine in other animal models of *tuberculosis*, including nonhuman primate models, is clearly warranted.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

SEQ ID NO:s

```
SEQ ID NO:1-An RD1 region of Mycobacterium tuberculosis H37Rv. Bases
4350263-4359716 of the genome of M. tuberculosis H37Rv, as provided
in GenBank Accession No. NC000962.
4350263 gatcgtgg gtgccgccgg ggggatgccg ccgatggcac 4350301 cgctggcccc gttattgccg gcggcggcag atatcgggtt gcacatcatt gtcacctgtc 4350361 agatgagcca ggcttacaag gcaaccatgg acaagttcgt cggcgccgca ttcgggtcgg 4350421 gcgctccgac aatgttcctt tcgggcgaga agcaggaatt cccatccagt gagttcaagg 4350481 tcaagcggcg ccccctggc caggcatttc tcgtctcgcc agacggcaaa gaggtcatcc 4350541 aggcccccta catcgagcct ccagaagaag tgttcgcagc accccaagc gccggttaag 4350601 attatttcat tgccggtgta gcaggacccg agctcagccc ggtaatcgag ttcgggcaat 4350661 gctgaccatc gggtttgttt ccggctataa ccgaacggtt tgtgtacggg atacaaatac 4350721 agggagggaa gaagtaggca aatggaaaaa atgtcacatg atccgatcgc tgccgacatt 4350781 ggcacgcaag tgagcgacaa cgctctgcac ggcgtgacgg ccggctcgac ggcgctgacg 4350841 tcggtgaccg ggctggttcc cgcggggcc gatgaggtct ccgcccaagc ggcgacggcg 4350901 ttcacatcgg agggcatcca attgctggct tccaatgcat cggcccaaga ccagctccac 4350961 cgtgcgggcg aagcggtcca ggacgtcgcc cgcacctatt cgcaaatcga cgacggcgcc 4351021 gccggcgtct tcgccgaata ggcccccaac acatcggagg gagtgatcac catgctgtgg 4351081 cacgcaatgc caccggagct aaataccgca cggctgatgg ccggcgcggg tccggctcca 4351141 atgcttgcgg cggccgcggg atggcagacg ctttcggcgg ctctggacgc tcaggccgtc 4351201 gagttgaccg cgcgcctgaa ctctctggga gaagcctgga ctggaggtgg cagcgacaag 4351261 gcgcttgcgg ctgcaacgcc gatggtggtc tggctacaaa ccgcgtcaac acaggccaag 4351321 acccgtgcga tgcaggcgac ggcgcaagcc gcggcataca cccaggccat ggccacgacg 4351381 ccgtcgctgc cggagatcgc cgccaaccac atcacccagg ccgtccttac ggccaccaac 4351441 ttcttcggta tcaacacgat cccgatcgcg ttgaccgaga tggattattt catccgtatg 4351501 tggaaccagg cagccctggc aatggaggtc taccaggccg agaccgcggt taacacgctt 4351561 ttcgagaagc tcgagccgat ggcgtcgatc cttgatcccg gcgcgagcca gagcacgacg 4351621 aacccgatct tcggaatgcc ctcccctggc agctcaacac cggttggcca gttgccgccg 4351681 gcggctaccc agaccctcgg ccaactgggt gagatgagcg gcccgatgca gcagctgacc 4351741 cagccgctgc agcaggtgac gtcgttgttc agccaggtgg gcggcaccgg cggcggcaac 4351801 ccagccgacg aggaagccgc gcagatgggc ctgctcggca ccagtccgct gtcgaaccat
```

-continued

```
4351861  ccgctggctg gtggatcagg ccccagcgcg ggcgcgggcc tgctgcgcgc ggagtcgcta
4351921  cctggcgcag gtgggtcgtt gacccgcacg ccgctgatgt ctcagctgat cgaaaagccg
4351981  gttgccccct cggtgatgcc ggcggctgct gccggatcgt cggcgacggg tggcgccgct
4352041  ccggtgggtg cgggagcgat gggccagggt gcgcaatccg gcggctccac caggccgggt
4352101  ctggtcgcgc cggcaccgct cgcgcaggag cgtgaagaag acgacgagga cgactgggac
4352161  gaagaggacg actggtgagc tcccgtaatg acaacagact ccccggccac ccgggccgga
4352221  agacttgcca acattttggc gaggaaggta aagagagaaa gtagtccagc atggcagaga
4352281  tgaagaccga tgccgctacc ctcgcgcagg aggcaggtaa tttcgagcgg atctccggcg
4352341  acctgaaaac ccagatcgac caggtggagt cgacggcagg ttcgttgcag ggccagtggc
4352401  gcgcgcggc ggggacggcc gcccaggccg cggtggtgcg cttccaagaa gcagccaata
4352461  agcagaagca ggaactcgac gagatctcga cgaatattcg tcaggccggc gtccaatact
4352521  cgagggccga cgaggagcag cagcaggcgc tgtcctcgca aatgggcttc tgacccgcta
4352581  atacgaaaag aaacggagca aaaacatgac agagcagcag tggaatttcg cgggtatcga
4352641  ggccgcggca agcgcaatcc agggaaatgt cacgtccatt cattccctcc ttgacgaggg
4352701  gaagcagtcc ctgaccaagc tcgcagcggc ctggggcggt agcggttcgg aggcgtacca
4352761  gggtgtccag caaaaatggg acgccacggc taccgagctg aacaacgcgc tgcagaacct
4352821  ggcgcggacg atcagcgaag ccggtcaggc aatggcttcg accgaaggca cgtcactgg
4352881  gatgttcgca tagggcaacg ccgagttcgc gtagaatagc gaaacacggg atcgggcgag
4352941  ttcgaccttc cgtcggtctc gcccttctc gtgtttatac gtttgagcgc actctgagag
4353001  gttgtcatgg cggccgacta cgacaagctc ttccggccgc acgaaggtat ggaagctccg
4353061  gacgatatgg cagcgcagcc gttcttcgac cccagtgctt cgtttccgcc ggcgcccgca
4353121  tcggcaaacc taccgaagcc caacggccag actccgcccc cgacgtccga cgacctgtcg
4353181  gagcggttcg tgtcggcccc gccgccgcca cccccacccc cacctccgcc tccgccaact
4353241  ccgatgccga tcgccgcagg agagccgccc tcgccggaac cggccgcatc taaaccaccc
4353301  acaccccca tgcccatcgc cggacccgaa ccggccccac ccaaaccacc cacacccccc
4353361  atgcccatcg ccggacccga accggcccca cccaaaccac ccacacctcc gatgcccatc
4353421  gccggacctg cacccacccc aaccgaatcc cagttggcgc ccccagacc accgacacca
4353481  caaacgccaa ccggagcgcc gcagcaaccg gaatcaccgg cgccccacgt accctcgcac
4353541  gggccacatc aacccccgcg caccgcacca gcaccgccct gggcaaagat gccaatcggc
4353601  gaaccccgc ccgctccgtc cagaccgtct gcgtccccgg ccgaaccacc gacccggcct
4353661  gccccccaac actcccgacg tgcgcgccgg ggtcaccgct atcgcacaga caccgaacga
4353721  aacgtcggga aggtagcaac tggtccatcc atccaggcgc ggctgcgggc agaggaagca
4353781  tccggcgcgc agctcgcccc cggaacggag ccctcgccag cgccgttggg ccaaccgaga
4353841  tcgtatctgg ctccgccacc cgccccgcg ccgacagaac ctcccccag cccctcgccg
4353901  cagcgcaact ccggtcggcg tgccgagcga cgcgtccacc ccgatttagc cgcccaacat
4353961  gccgcggcgc aacctgattc aattacggcc gcaaccactg gcggtcgtcg ccgcaagcgt
4354021  gcagcgccgg atctcgacgc gacacagaaa tccttaaggc cggcggccaa ggggccgaag
4354081  gtgaagaagg tgaagcccca gaaaccgaag gccacgaagc cgcccaaagt ggtgtcgcag
4354141  cgcggctggc gacattgggt gcatgcgttg acgcgaatca acctgggcct gtcacccgac
4354201  gagaagtacg agctggacct gcacgctcga gtccgccgca atcccgcgcg gtcgtatcag
```

```
-continued
4354261  atcgccgtcg tcggtctcaa aggtggggct ggcaaaacca cgctgacagc agcgttgggg
4354321  tcgacgttgg ctcaggtgcg ggccgaccgg atcctggctc tagacgcgga tccaggcgcc
4354381  ggaaacctcg ccgatcgggt agggcgacaa tcgggcgcga ccatcgctga tgtgcttgca
4354441  gaaaaagagc tgtcgcacta caacgacatc cgcgcacaca ctagcgtcaa tgccggtcaat
4354501  ctggaagtgc tgccggcacc ggaatacagc tcggcgcagc gcgcgctcag cgacgccgac
4354561  tggcatttca tcgccgatcc tgcgtcgagg ttttacaacc tcgtcttggc tgattgtggg
4354621  gccggcttct tcgacccgct gacccgcggc gtgctgtcca cggtgtccgg tgtcgtggtc
4354681  gtggcaagtg tctcaatcga cggcgcacaa caggcgtcgg tcgcgttgga ctggttgcgc
4354741  aacaacggtt accaagattt ggcgagccgc gcatgcgtgg tcatcaatca catcatgccg
4354801  ggagaaccca atgtcgcagt taaagacctg gtgcggcatt tcgaacagca agttcaaccc
4354861  ggccgggtcg tggtcatgcc gtgggacagg cacattgcgg ccggaaccga gatttcactc
4354921  gacttgctcg accctatcta caagcgcaag gtcctcgaat tggccgcagc gctatccgac
4354981  gatttcgaga gggctggacg tcgttgagcg cacctgctgt tgctgctggt cctaccgccg
4355041  cggggcaac cgctgcgcgg cctgccacca cccgggtgac gatcctgacc ggcagacgga
4355101  tgaccgattt ggtactgcca gcggcggtgc cgatggaaac ttatattgac gacaccgtcg
4355161  cggtgctttc cgaggtgttg aagacacgc cggctgatgt actcggcggc ttcgactta
4355221  ccgcgcaagg cgtgtgggcg ttcgctcgtc ccggatcgcc gccgctgaag ctcgaccagt
4355281  cactcgatga cgccggggtg gtcgacgggt cactgctgac tctggtgtca gtcagtcgca
4355341  ccgagcgcta ccgaccgttg gtcgaggatg tcatcgacgc gatcgccgtg cttgacgagt
4355401  cacctgagtt cgaccgcacg gcattgaatc gctttgtggg ggcggcgatc ccgcttttga
4355461  ccgcgcccgt catcgggatg gcgatgcggg cgtggtggga aactgggcgt agcttgtggt
4355521  ggccgttggc gattggcatc ctggggatcg ctgtgctggt aggcagcttc gtcgcgaaca
4355581  ggttctacca gagcggccac ctggccgagt gcctactggt cacgacgtat ctgctgatcg
4355641  caaccgccgc agcgctggcc gtgccgttgc cgcgcggggt caactcgttg ggggcgccac
4355701  aagttgccgg cgccgctacg gccgtgctgt ttttgacctt gatgacgcgg ggcggccctc
4355761  ggaagcgtca tgagttggcg tcgtttgccg tgatcaccgc tatcgcggtc atcgcggccg
4355821  ccgctgcctt cggctatgga taccaggact gggtccccgc gggggggatc gcattcgggc
4355881  tgttcattgt gacgaatgcg gccaagctga ccgtcgcgt cgcgcggatc gcgctgccgc
4355941  cgattccggt acccggcgaa accgtggaca acgaggagtt gctcgatccc gtcgcgaccc
4356001  cggaggctac cagcgaagaa ccccgacct ggcaggccat catcgcgtcg gtgcccgcgt
4356061  ccgcggtccg gctcaccgag cgcagcaaac tggccaagca acttctgatc ggatacgtca
4356121  cgtcgggcac cctgattctg gctgccggtg ccatcgcgt cgtggtgcgc gggcacttct
4356181  ttgtacacag cctggtggtc gcgggttga tcacgaccgt ctgcggattt cgctcgcggc
4356241  tttacgccga gcgctggtgt gcgtgggcgt tgctggcggc gacggtcgcg attccgacgg
4356301  gtctgacggc caaactcatc atctggtacc cgcactatgc ctggctgttg ttgagcgtct
4356361  acctcacggt agccctggtt gcgctcgtgg tggtcgggtc gatggctcac gtccggcgcg
4356421  tttcaccggt cgtaaaacga actctggaat tgatcgacgg cgccatgatc gctgccatca
4356481  ttcccatgct gctgtggatc accggggtgt acgacacggt ccgcaatatc cggttctgag
4356541  ccggatcggc tgattggcgg ttcctgacag aacatcgagg acacggcgca ggtttgcata
4356601  ccttcggcgc ccgacaaatt gctgcgattg agcgtgtggc gcgtccggta aaatttgctc
4356661  gatggggaac acgtatagga gatccggcaa tggctgaacc gttggccgtc gatcccaccg
```

-continued

```
4356721  gcttgagcgc agcggccgcg aaattggccg gcctcgtttt tccgcagcct ccggcgccga
4356781  tcgcggtcag cggaacggat tcggtggtag cagcaatcaa cgagaccatg ccaagcatcg
4356841  aatcgctggt cagtgacggg ctgcccggcg tgaaagccgc cctgactcga acagcatcca
4356901  acatgaacgc ggcggcggac gtctatgcga agaccgatca gtcactggga accagtttga
4356961  gccagtatgc attcggctcg tcgggcgaag gcctggctgg cgtcgcctcg gtcggtggtc
4357021  agccaagtca ggctacccag ctgctgagca cacccgtgtc acaggtcacg acccagctcg
4357081  gcgagacggc cgctgagctg gcaccccgtg ttgttgcgac ggtgccgcaa ctcgttcagc
4357141  tggctccgca cgccgttcag atgtcgcaaa acgcatcccc catcgctcag acgatcagtc
4357201  aaaccgccca acaggccgcc cagagcgcgc agggcggcag cggcccaatg cccgcacagc
4357261  ttgccagcgc tgaaaaaccg gccaccgagc aagcggagcc ggtccacgaa gtgacaaacg
4357321  acgatcaggg cgaccagggc gacgtgcagc cggccgaggt cgttgccgcg gcacgtgacg
4357381  aaggcgccgg cgcatcaccg ggccagcagc ccggcggggg cgttcccgcg caagccatgg
4357441  ataccggagc cggtgcccgc ccagcggcga gtccgctggc ggccccgtc gatccgtcga
4357501  ctccggcacc ctcaacaacc acaacgttgt agaccgggcc tgccagcggc tccgtctcgc
4357561  acgcagcgcc tgttgctgtc ctggcctcgt cagcatgcgg cggccagggc ccggtcgagc
4357621  aacccggtga cgtattgcca gtacagccag tccgcgacgg ccacacgctg gacggccgcg
4357681  tcagtcgcag tgtgcgcttg gtgcagggca atctcctgtg agtgggcagc gtaggcccgg
4357741  aacgcccgca gatgagcggc ctcgcggccg gtagcggtgc tggtcatggg cttcatcagc
4357801  tcgaaccaca gcatgtgccg ctcatcgccc ggtggattga catccaccgg cgccggcggc
4357861  aacaagtcga gcaaacgctg atcggtagtg tcggccagct gagccgccgc cgaggggtcg
4357921  acgacctcca gccgcgaccg gcccgtcatt ttgccgctct ccggaatgtc atctggctcc
4357981  agcacaatct tggccacacc gggatccgaa ctggccaact gctccgcggt accgatcacc
4358041  gcccgcagcg tcatgtcgtg gaaagccgcc caggcttgca cggccaaaac cgggtaggtg
4358101  gcacagcgtg caatttcgtc aaccgggatt gcgtgatccg cgctggccaa gtacaccta
4358161  ttcggcaatt ccatcccgtc gggtatgtag gccagcccat agctgttggc cacgacgatg
4358221  gaaccgtcgg tggtcaccgc ggtgatccag aagaacccgt agtcgcccgc gttgttgtcg
4358281  gacgcgttga gcgccgccgc gatgcgtcgc gccaaccgca gcgcatcacc gcggccacgc
4358341  tggcgggcgc tggcagctgc agtggcggcg tcgcgtgccg cccgagccgc cgacaccggg
4358401  atcatcgaca ccggcgtacc gtcatctgca gactcgctgc gatcgggttt gtcgatgtga
4358461  tcggtcgacg gcgggcgggc aggaggtgcc gtccgcgccg aggccgcccg cgtgctcggt
4358521  gccgccgcct tgtccgaggt agccaccggc gcccgcccag tggcagcatg cgacccgcgc
4358581  cccgaggccg cggccgtacc cacgctcgaa cgcgcgcccg ctcccacggc ggtaccgctc
4358641  ggcgcggcgg ccgccgcccg tgcgcccggg acaccggacg ccgcagccgg cgtcaccgac
4358701  gcggcggatt cgtccgcatg ggcaggcccc gactgcgtcc cccgcccgc atgctggccc
4358761  ggcacaccag gttgctccgc caacgccgcg ggtttgacgt gcggcgccgg ctcgccccct
4358821  ggggtgcccg gtgttgctgg accagacgga ccgggagtgg ccggtgtaac cggctggggc
4358881  ccaggcgatg gcgccggtgc cggagccggc tgcgggtgtg gagcgggagc tggggtaacg
4358941  ggcgtggccg gggttgccgg tgtggccggg gcgaccgggg gggtgaccgg cgtgatcggg
4359001  gttggctcgc ctggtgtgcc cggtttgacc ggggtcaccg gggtgaccgg cttgccgggg
4359061  gtcaccggcg tgacgggagt gccgggcgtt ggtgtgatcg gagttaccgg cgctcccggg
```

-continued

```
4359121 atgggtgtga ttggggttcc cggggtgatc ggggttcccg gggtgatcgg ggttcccggt
4359181 gtgcccggtg tgcccgggga tggcacgacc agggtaggca cgtctggggg tggcggcgac
4359241 ttctgctgaa gcaaatcctc gagtgcgttc ttcggaggtt tccaattctt ggattccagc
4359301 acccgctcag cggtctcggc gaccagactg acattggccc catgcgtcgc cgtgaccaat
4359361 gaattgatgg cggtatggcg ctcatcagca tccaggctag ggtcattctc caggatatcg
4359421 atctcccgtt gagcgccatc cacattattg ccgatatcgg atttagcttg ctcaatcaac
4359481 ccggcaatat gcctgtgcca ggtaatcacc gtggcgagat aatcctgcag cgtcatcaat
4359541 tgattgatgt ttgcacccag ggcgccgttg gcagcattgg cggcgccgcc ggaccatagg
4359601 ccgccttcga agacgtggcc tttctgctgg cggcaggtgt ccaatacatc ggtgaccctt
4359661 tgcaaaacct ggctatattc ctgggcccgg tcatagaaag tgtcttcatc ggcttc
```

SEQ ID NO:2-A panCD region of *Mycobacterium tuberculosis* H37Rv, deleted in the ΔpanCD strain of Example 2.

```
GGTCTAGCAGCTCGCCCGCGTTTTCGGGCACAAATGCCGGATCGTGGCCC
ATGTCGATCGGTTTGTTGTAAGCGTCGACAAACACGATCCGCGGCTGGTA
TGTGCGGGCCCGGGCGTCGTCCATCGTCGCGTACGCAATCAGAATCACCA
GATCCCCCGGATGCACCAAGTGCGCGGCGGCACCGTTGATGCCAATCACA
CCACTGCCGCGTTCGCCGGTGATCGCGTAGGTGACCAGTCGAGCACCGTT
GTCGATATCGACGATGGTTACCTGTTCGCCTTCCAGCAGGTCGGCGGCGT
CCATCAAGTCGGCATCGATGGTCACCGAGCCGACGTAGTGCAGGTCGGCG
CAGGTCACCGTGGCGCGGTGGATCTTCGACTTCAGCATCGTCCGTAACAT
CAGTTTCTCCAATGTGATTCGAGGATTGCCCGGTATCCGTCCGGGCGGTC
GGTGCCGGCGAAAGTTCCGATTTCAATCGCAATGTTGTCCAGCAGCCTGG
TGGTGCCAAGCCGGGCAGCAACCAGCAGCCGACCGGAACCGTTGAGCGGC
ATCCGGGCCAAGCCCGATATCGCGCAGCTCCAGGTAGTCGACCGCCACGC
CGGGTGCAGCGTCGAGCACCGCACGGGCGGCATCCAGCGCGGCGTGCGCG
CCAGCCGTTGCCGCATGCGCTGCGGCCGTTAGCGCCGCCGAGAGCGCGAC
GGCCGCCGCACGCTGGGCCGGGTCCAGGTAGCGGTTGCGCGACGACATCG
CCAGCCCGTCGGCTTCGCGCACGGTCGGCACGCCGACCACCGCGACATCG
AGGTTGAAGTCCGCGACCAGCTGCCGGATCAGCACCAGCTGCTGGTAGTC
CTTCTCACCGAAGAACACCCGATCCGGGCGCACGATCTGCAGCAGCTTTA
GCACGACCGTCAGCACGCCGGCGAAATGGGTTGGCCGCGGGCCGCCCTCG
AGTTCGGCGGCCAACGGACCGGGTTGCACGGTGGTGCGCAGGCCGTCGGG
ATACATCGCCGCGGTAGTTGGCGTGAAAGCGATTTCCACGCCTTCGGCCC
GCAGTTGCGCCAGGTCGTCGTCCGGGTGCGGGGATAGGCGTCGAGATCTT
CCCCGGCACCGAATTGCATCGGGTTGACGAAGATCGACACGACGACGACC
GATCCGGGCACCCGCTTGGCCGCACGCACCAACGCGAGGTGGCCTTCGTG
CAGCGCACCCATAGTAGGCACCAACATCACTCGCCGGCCGGTGAGTCGCA
GTGCGCGACTGACATCGGCGACATCCCCCGGTGCCGAGTACACATTGA
```

-continued

SEQ ID NO:3-A nadBC region of *Mycobacterium tuberculosis* H37Rv. Deleted in ΔnadBC strain of Example 2.

```
AACGGGCGATGAGCCGGGACGCGTCGATGTACCGCGCCGCCGCCGGGCTG
CACCGGCTGTGCGACAGCCTATCCGGAGCACAGGTTCGCGACGTGGCTTG
TCGCCGCGATTTCGAGGACGTGGCGCTCACGCTGGTCGCGCAGAGCGTGA
CCGCCGCCGCCTTGGCCCGCACCGAAAGCCGTGGCTGCCATCATCGCGCG
GAGTACCCGTGCACCGTGCCGGAGCAGGCAGGCAGCATCGTGGTCCGGGG
AGCCGACGACGCAAATGCGGTGTGTGTCCAGGCGCTAGTGGCGGTGTGCT
GATGGGGTTATCCGACTGGGAGCTGGCTGCGGCTCGAGCAGCAATCGCGC
GTGGGTCGACGAGGACCTCCGGTACGGCCCGGATGTCACCACATTGGCGA
CGGTGCCTGCCAGTGCGACGACCACCGCATCGCTGGTGACCCGGGAGGCC
GGTGTGGTTGCCGGATTGGATGTCGCGCTGCTGACGCTGAACGAAGTCCT
GGGCACCAACGGTTATCGGGTGCCGACCGCGTCGAGGACGGCGCCCGGGT
GCCGCCGGGAGAGGCACTTATGACGCTGGAAGCCCAAACGCGCGGAATTG
TTGACCGCCGAGCGCACCATGTTGAACCTGGTCGGTCACCTGTCGGGAAT
CGCCACCGCGACGGCCGCGTGGGTCGATGCTGTGCGCGGGACCAAAGCGA
AAATCCGCGATACCCGTAAGACGCTGCCCGGCCTGCGCGCGCTGCAAAAA
TACGCGGTGCGTACCGGTGG
```

SEQ ID NO:4-A lysA sequence deleted in ΔlysA s-trains

```
GTGAACGAGCTGCTGCACTTAGCGCCGAATGTGTGGCCGCGCAATACTAC
TCGCGATGAAGTCGGTGTGGTCTGCATCGCAGGAATTCCACTGACGCAGC
TCGCCCAGGAGTACGGGACCCCGCTGTTCGTCATCGACGAGGACGACTTT
CGCTCGCGCTCGAGAAACCGCCGCGGCCTTTGGAAGTGGGGCGAACGTGC
ACTATGCCGCCAAGGCGTTCCTGTGCAGCGAAGTAGCCCGGTGGATCAGC
GAAGAAGGGCTCTGTCTGGACGTTTGCACCGGTGGGGAGTTGGCGGTCGC
GCTGCACGCTAGCTTTCCGCCCGAGCGAATTACCTTGCACGGCAACAACA
AATCGGTCTCAGAGTTGACCGCTGCGGTCAAAGCCGGAGTCGGCCATATT
GTCGTCGATTCGATGACCGAGATCGAGCGCCTCGACGCCATCGCGGGCGA
GGCCGGAATCGTCCAGGATGTCCTGGTGCGTCTCACCGTCGGTGTCGAGG
CGCACACCCACGAGTTCATCTCCACCGCGCACGAGACGCGTCAGCCACAT
```

CGGTTCGCAGATCTTCGACGTGGACGGCTTCGAACTCGCCGCGCACCGTG

TCATCGGCCTGCTACGCGACGTCGTCGGCGAGTTCGGTCCCGAAAAGACG

GCACAGATCGCGACCGTCGATCTCGGTGGCGGCTTGGGCATCTCGTATTT

TGCCGTCCGACGACCCACCGCCGATAGCCGAGCTCGCGGCCAAGCTGGGT

ACCATCGTGAGCGACGAGTCAACGGCCGTGGGGCTGCCGACGCCCAAGCT

CGTTGTGGAGCCCGGACGCGCCATCGCCGGACCGGGCACCATCACGTGTA

TGAGGTCGGCACCGTTAAGGACGTCGATGTCAGCGCCACAGCGCATCGAC

GTTACGTCAGTGTCGACGGCGGCATGAGCGACAACATCCGCACCGCGCTC

TACGGCGCGCAGTATGACGTCCGGCTGGTGTCTCGAGTCAGCGACGCCCC

GCCGGTACCGGCCCGTCTGGTCGGAAAGCACTGCGAAAGTGGCGATATCA

TCGTGCGGGACACCTGGGTGCCCGACGATATTCGGCCCGGCGATCTGGTT

GCGGTTGCCGCCACCGGCGCTTACTGCTATTCGCTGTCGAGTCGTTACAA

CATGGTCGGCCGTCCCGCTGTGGTAGCGGTGCACGCGGGCAACGCTCGCC

TGGTCCTGCGTCGGGAGACGGTCGACGATTTGCTGAGTTTGGAAGTGAGG

TGA

SEQ ID NO:5-primer TH201
GGGGGCGCACCTCAAACC

SEQ ID NO:6-primer TH202
ATGTGCCAATCGTCGACCAGAA

SEQ ID NO:7-primer TH203
CACCCAGCCGCCCGGAT

SEQ ID NO:8-primer TH204
TTCCTGATGCCGCCGTCTGA

SEQ ID NO:9-primer Pan1
GTGCAGCGCCATCTCTCA

SEQ ID NO:10-primer Pan2
GTTCACCGGGATGGAACG

SEQ ID NO:11-primer Pan3
CCCGGCTCGGTGTGGGAT

SEQ ID NO:12-primer Pan4
GCGCGGTATGCCCGGTAG

---

What is claimed is:

1. A method for inoculating an immunocompromised mammal against *Mycobacterium tuberculosis*, wherein the mammal does not have severe combined immune deficiency but is deficient in CD4$^+$ lymphocytes or in CD8$^+$ lymphocytes, the method comprising administering to the immunocompromised mammal an amount of an attenuated *M. tuberculosis* or *M. bovis* mycobacterium effective to confer protection against *Mycobacterium tuberculosis* in the mammal, wherein the attenuated mycobacterium has (i) a deletion of RD1 and is auxotrophic for pantothenate, or (ii) is auxotrophic for both lysine and pantothenate.

2. The method of claim 1, wherein the attenuated mycobacterium is an *M. tuberculosis*.

3. The method of claim 1, wherein the attenuated mycobacterium is an *M. bovis*.

4. The method of claim 1, wherein the mammal is a human.

5. The method of claim 1, wherein the RD1 deletion is a ΔpanCD deletion.

6. The method of claim 1, wherein the mammal is deficient in CD8$^+$ lymphocytes.

7. The method of claim 1, wherein the mammal is deficient in CD4$^+$ lymphocytes.

8. The method of claim 1, wherein the attenuated mycobacterium has a deletion of RD1 and is auxotrophic for pantothenate.

9. The method of claim 1, wherein the attenuated mycobacterium is auxotrophic for both lysine and pantothenate.

* * * * *

UNITED STATES PATENT AND TRADEMARK OFFICE
CERTIFICATE OF CORRECTION

| | | |
|---|---|---|
| PATENT NO. | : 8,084,041 B2 | Page 1 of 1 |
| APPLICATION NO. | : 10/542958 | |
| DATED | : December 27, 2011 | |
| INVENTOR(S) | : William R. Jacobs, Jr. et al. | |

It is certified that error appears in the above-identified patent and that said Letters Patent is hereby corrected as shown below:

In the Specification

Column 1, lines 13-20, should read:

-- STATEMENT OF GOVERNMENT SUPPORT

This invention was made with government support under grant number AI26170 awarded by the National Institutes of Health. The government has certain rights in the invention. --

Signed and Sealed this
Third Day of November, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 9454
<212> TYPE: DNA
<213> ORGANISM: Mycobacterium tuberculosis

<400> SEQUENCE: 1
gatcgtgggt gccgccgggg ggatgccgcc gatggcaccg ctggccccgt tattgccggc      60
ggcggcagat atcgggttgc acatcattgt cacctgtcag atgagccagg cttacaaggc     120
aaccatggac aagttcgtcg gcgccgcatt cgggtcgggc gctccgacaa tgttcctttc     180
gggcgagaag caggaattcc catccagtga gttcaaggtc aagcggcgcc cccctggcca     240
ggcatttctc gtctcgccag acggcaaaga ggtcatccga gcccctaca tcgagcctcc     300 agaagaagtg ttcgcagcac ccccaagcgc cggttaagat tatttcattg ccggtgtagc     360
aggacccgag ctcagcccgg taatcgagtt cgggcaatgc tgaccatcgg gtttgtttcc     420
ggctataacc gaacggtttg tgtacgggat acaaatacag ggagggaaga agtaggcaaa     480
tggaaaaaat gtcacatgat ccgatcgctg ccgacattgg cacgcaagtg agcgacaacg     540
ctctgcacgg cgtgacggcc ggctcgacgg cgctgacgtc ggtgaccggg ctggttcccg     600 cggggccga tgaggtctcc gcccaagcgg cgacggcgtt cacatcggag ggcatccaat     660
tgctggcttc caatgcatcg gcccaagacc agctccaccg tgcgggcgaa gcggtccagg     720
acgtcgcccg cacctattcg caaatcgacg acggcgcgc cggcgtcttc gccgaatagg     780 ccccaacac atcggaggga gtgatcacca tgctgtggca cgcaatgcca ccggagctaa     840
ataccgcacg gctgatggcc ggcgcgggtc cggctccaat gcttgcggcg gccgcgggat     900
ggcagacgct ttcggcggct ctggacgctc aggccgtcga gttgaccgcg cgcctgaact     960
ctctgggaga agcctggact ggaggtggca gcgacaaggc gcttgcgggct gcaacgccga    1020 tggtggtctg gctacaaacc gcgtcaacac aggccaagac ccgtgcgatg caggcgacgg    1080
cgcaagccgc ggcatacacc caggccatgg ccacgacgcc gtcgctgccg gagatcgccg    1140

```
ccaaccacat cacccaggcc gtccttacgg ccaccaactt cttcggtatc aacacgatcc    1200
cgatcgcgtt gaccgagatg gattatttca tccgtatgtg aaccaggca gccctggcaa    1260 tggaggtcta ccaggccgag accgcggtta acacgctttt cgagaagctc gagccgatgg    1320
cgtcgatcct tgatcccggc gcgagccaga gcacgacgaa cccgatcttc ggaatgccct    1380
cccctggcag ctcaacaccg gttggccagt tgccgccggc ggctacccag accctcggcc    1440
aactgggtga gatgagcggc ccgatgcagc agctgaccca gccgctgcag caggtgacgt    1500
cgttgttcag ccaggtgggc ggcaccggcg gcggcaaccc agccgacgag gaagccgcgc    1560
agatgggcct gctcggcacc agtccgctgt cgaaccatcc gctggctggt ggatcaggcc    1620
ccagcgcggg cgcgggcctg ctgcgcgcgg agtcgctacc tggcgcaggt gggtcgttga    1680
cccgcacgcc gctgatgtct cagctgatcg aaaagccggt tgcccctcg gtgatgccgg     1740 cggctgctgc cggatcgtcg gcgacgggtg gcgccgctcc ggtgggtgcg ggagcgatgg    1800
gccagggtgc gcaatccggc ggctccacca ggccgggtct ggtcgcgccg gcaccgctcg    1860
cgcaggagcg tgaagaagac gacgaggacg actgggacga agaggacgac tggtgagctc    1920
ccgtaatgac aacagacttc ccggccaccc gggccggaag acttgccaac attttggcga    1980
ggaaggtaaa gagagaaagt agtccagcat ggcagagatg aagaccgatg ccgctaccct    2040
cgcgcaggag gcaggtaatt tcgagcggat ctccggcgac ctgaaaaccc agatcgacca    2100
ggtggagtcg acggcaggtt cgttgcaggg ccagtggcgc ggcgcggcgg gacggccgc    2160 ccaggccgcg gtggtgcgct tccaagaagc agccaataag cagaagcagg aactcgacga    2220
gatctcgacg aatattcgtc aggccggcgt ccaatactcg agggccgacg aggagcagca    2280
gcaggcgctg tcctcgcaaa tgggcttctg acccgctaat acgaaaagaa acggagcaaa    2340
aacatgacag agcagcagtg gaatttcgcg ggtatcgagg ccgcggcaag cgcaatccag    2400
ggaaatgtca cgtccattca ttccctcctt gacgagggga agcagtccct gaccaagctc    2460
gcagcggcct ggggcggtag cggttcggag gcgtaccagg gtgtccagca aaaatgggac    2520
gccacggcta ccgagctgaa caacgcgctg cagaacctgg cgcggacgat cagcgaagcc    2580
ggtcaggcaa tggcttcgac cgaaggcaac gtcactggga tgttcgcata gggcaacgcc    2640
gagttcgcgt agaatagcga aacacggat cgggcgagtt cgaccttccg tcggtctcgc     2700
cctttctcgt gtttatacgt ttgagcgcac tctgagaggt tgtcatggcg gccgactacg    2760
acaagctctt ccggccgcac gaaggtatgg aagctccgga cgatatggca gcgcagccgt    2820
tcttcgaccc cagtgcttcg tttccgccgg cgcccgcatc ggcaaaccta ccgaagccca    2880
acggccagac tccgccccg acgtccgacg acctgtcgga gcggttcgtg tcggccccgc     2940
cgccgccacc cccaccccca cctccgcctc cgccaactcc gatgccgatc gccgcaggag    3000
agccgccctc gccggaaccg gccgcatcta aaccacccac accccccatg cccatcgccg    3060
gacccgaacc ggccccaccc aaaccaccca caccccccat gccatcgcc ggacccgaac     3120 cggccccacc caaaccaccc acacctccga tgcccatcgc cggacctgca cccaccccaa    3180
ccgaatccca gttggcgccc cccagaccac cgacaccaca aacgcaacc ggagcgccgc     3240 agcaaccgga atcaccggcg ccccacgtac cctcgcacgg gccacatcaa ccccggcgca    3300
ccgcaccagc accgccctgg gcaaagatgc caatcgcga accccgccc gctcgtcca      3360 gaccgtctgc gtccccggcc gaaccaccga cccggcctgc cccccaacac tccgacgtg     3420 cgcgccgggg tcaccgctat cgcacagaca ccgaacgaaa cgtcgggaag gtagcaactg    3480
gtccatccat ccaggcgcgg ctgcgggcag aggaagcatc cggcgcgcag ctcgcccccg    3540
```

```
gaacggagcc ctcgccagcg ccgttgggcc aaccgagatc gtatctggct ccgcccaccc    3600
gccccgcgcc gacagaacct cccccagcc cctcgccgca gcgcaactcc ggtcggcgtg    3660
ccgagcgacg cgtccacccc gatttagccg cccaacatgc cgcggcgcaa cctgattcaa    3720
ttacggccgc aaccactggc ggtcgtcgcc gcaagcgtgc agcgccggat ctcgacgcga    3780
cacagaaatc cttaaggccg gcggccaagg ggccgaaggt gaagaaggtg aagcccccaga   3840 aaccgaaggc cacgaagccg cccaaagtgg tgtcgcagcg cggctggcga cattgggtgc    3900
atgcgttgac gcgaatcaac ctgggcctgt caccccgacga gaagtacgag ctggacctgc   3960
acgctcgagt ccgccgcaat ccccgcgggt cgtatcagat cgccgtcgtc ggtctcaaag    4020
gtggggctgg caaaaccacg ctgacagcag cgttggggtc gacgttggct caggtgcggg    4080
ccgaccggat cctggctcta gacgcggatc caggcgccgg aaacctcgcc gatcgggtag    4140
ggcgacaatc gggcgcgacc atcgctgatg tgcttgcaga aaagagctg tcgcactaca     4200 acgacatccg cgcacacact agcgtcaatg cggtcaatct ggaagtgctg ccggcaccgg    4260
aatacagctc ggcgcagcgc gcgctcagcg acgccgactg gcatttcatc gccgatcctg    4320
cgtcgaggtt ttacaacctc gtcttggctg attgtggggc cggcttcttc gacccgctga    4380
cccgcggcgt gctgtccacg gtgtccggtg tcgtggtcgt ggcaagtgtc tcaatcgacg    4440
gcgcacaaca ggcgtcggtc gcgttggact ggttgcgcaa caacggttac caagatttgg    4500
cgagccgcgc atgcgtggtc atcaatcaca tcatgccggg agaacccaat gtcgcagtta    4560
aagacctggt gcggcatttc gaacagcaag ttcaacccgg ccgggtcgtg gtcatgccgt    4620
gggacaggca cattgcggcc ggaaccgaga tttcactcga cttgctcgac cctatctaca    4680
agcgcaaggt cctcgaattg gccgcagcgc tatccgacga tttcgagagg gctggacgtc    4740
gttgagcgca cctgctgttg ctgctggtcc taccgccgcg ggggcaaccg ctgcgcggcc    4800
tgccaccacc cgggtgacga tcctgaccgg cagacggatg accgatttgg tactgccagc    4860
ggcggtgccg atggaaactt atattgacga caccgtcgcg gtgcttccg aggtgttgga     4920 agacacgccg gctgatgtac tcggcggctt cgactttacc gcgcaaggcg tgtgggcgtt    4980
cgctcgtccc ggatcgccgc cgctgaagct cgaccagtca ctcgatgacg ccggggtggt    5040
cgacgggtca ctgctgactc tggtgtcagt cagtcgcacc gagcgctacc gaccgttggt    5100
cgaggatgtc atcgacgcga tcgccgtgct tgacgagtca cctgagttcg accgcacggc    5160
attgaatcgc tttgtggggg cggcgatccc gcttttgacc gcgcccgtca tcgggatggc    5220
gatgcgggcg tggtgggaaa ctgggcgtag cttgtggtgg ccgttggcga ttggcatcct    5280
ggggatcgct gtgctggtag gcagcttcgt cgcgaacagg ttctaccaga gcggccacct    5340
ggccgagtgc ctactggtca cgacgtatct gctgatcgca accgccgcag cgctggccgt    5400
gccgttgccg cgcggggtca actcgttggg ggcgccacaa gttgccggcg ccgctacggc    5460
cgtgctgttt ttgaccttga tgacgcgggg cggccctcgg aagcgtcatg agttggcgtc    5520
gtttgccgtg atcaccgcta tcgcggtcat cgcggccgcc gctgccttcg gctatggata    5580
ccaggactgg gtccccgcgg gggggatcgc attcggctg ttcattgtga cgaatgcggc     5640
caagctgacc gtcgcggtcg cgcggatcgc gctgccgccg attccggtac ccggcgaaac    5700
cgtggacaac gaggagttgc tcgatcccgt cgcgaccccg gaggctacca gcgaagaaac    5760
cccgacctgg caggccatca tcgcgtcggt gcccgcgtcc gcggtccggc tcaccgagcg    5820
cagcaaactg gccaagcaac ttctgatcgg atacgtcacg tcgggcaccc tgattctggc    5880
tgccggtgcc atcgcggtcg tggtgcgcgg gcacttcttt gtacacagcc tggtggtcgc    5940
```

-continued

```
gggtttgatc acgaccgtct gcggatttcg ctcgcggctt tacgccgagc gctggtgtgc      6000
gtgggcgttg ctggcggcga cggtcgcgat tccgacgggt ctgacggcca aactcatcat      6060
ctggtacccg cactatgcct ggctgttgtt gagcgtctac ctcacggtag ccctggttgc      6120
gctcgtggtg gtcgggtcga tggctcacgt ccggcgcgtt tcaccggtcg taaaacgaac      6180
tctggaattg atcgacggcg ccatgatcgc tgccatcatt cccatgctgc tgtggatcac      6240
cggggtgtac gacacggtcc gcaatatccg gttctgagcc ggatcggctg attggcggtt      6300
cctgacagaa catcgaggac acggcgcagg tttgcatacc ttcggcgccc gacaaattgc      6360
tgcgattgag cgtgtggcgc gtccggtaaa atttgctcga tggggaacac gtataggaga      6420
tccggcaatg gctgaaccgt tggccgtcga tcccaccggc ttgagcgcag cggccgcgaa      6480
attggccggc ctcgtttttc cgcagcctcc ggcgccgatc gcggtcagcg gaacggattc      6540
ggtggtagca gcaatcaacg agaccatgcc aagcatcgaa tcgctggtca gtgacgggct      6600 gccccggcgtg aaagccgccc tgactcgaac agcatccaac atgaacgcgg cggcggacgt      6660
ctatgcgaag accgatcagt cactgggaac cagtttgagc cagtatgcat tcggctcgtc      6720
gggcgaaggc ctggctggcg tcgcctcggt cggtggtcag ccaagtcagg ctacccagct      6780
gctgagcaca cccgtgtcac aggtcacgac ccagctcggc gagacggccg ctgagctggc      6840
accccgtgtt gttgcgacgg tgccgcaact cgttcagctg gctccgcacg ccgttcagat      6900
gtcgcaaaac gcatccccca tcgctcagac gatcagtcaa accgcccaac aggccgccca      6960
gagcgcgcag ggcggcagcg gcccaatgcc cgcacagctt gccagcgctg aaaaaccggc      7020
caccgagcaa gcggagccgg tccacgaagt gacaaacgac gatcagggcg accagggcga      7080
cgtgcagccg gccgaggtcg ttgccgcggc acgtgacgaa ggcgccggcg catcaccggg      7140
ccagcagccc ggcgggggcg ttcccgcgca agccatggat accggagccg gtgcccgccc      7200
agcggcgagt ccgctggcgg cccccgtcga tccgtcgact ccggcaccct caacaaccac      7260
aacgttgtag accgggcctg ccagcggctc cgtctcgcac gcagcgcctg ttgctgtcct      7320
ggcctcgtca gcatgcggcg gccagggccc ggtcgagcaa cccggtgacg tattgccagt      7380
acagccagtc cgcgacggcc acacgctgga cggccgcgtc agtcgcagtg tgcgcttggt      7440
gcagggcaat ctcctgtgag tgggcagcgt aggcccggaa cgcccgcaga tgagcggcct      7500
cgcggccggt agcggtgctg gtcatgggct tcatcagctc gaaccacagc atgtgccgct      7560
catcgcccgg tggattgaca tccaccggcg ccggcggcaa caagtcgagc aaacgctgat      7620
cggtagtgtc ggccagctga ccgccgccg aggggtcgac gacctccagc cgcgaccggc      7680
ccgtcatttt gccgctctcc ggaatgtcat ctggctccag cacaatcttg cccacaccgg      7740
gatccgaact ggccaactgc tccgcggtac cgatcaccgc ccgcagcgtc atgtcgtgga      7800
aagccgccca ggcttgcacg gccaaaaccg ggtaggtggc acagcgtgca atttcgtcaa      7860
ccgggattgc gtgatccgcg ctggccaagt acaccttatt cggcaattcc atcccgtcgg      7920
gtatgtaggc cagcccatag ctgttggcca cgacgatgga accgtcggtg gtcaccgcgg      7980
tgatccgaga gaacccgtag tcgcccgcgt tgttgtcgga cgcgttgagc gccgccgcga      8040
tgcgtcgcgc caaccgcagc gcatcaccgc ggccacgctg gcgggcgctg gcagctgcag      8100
tggcggcgtc gcgtgccgcc cgagccgccg acaccggat catcgacacc ggcgtaccgt      8160
catctgcaga ctcgctgcga tcgggtttgt cgatgtgatc ggtcgacggc gggcgggcag      8220
gaggtgccgt ccgcgccgag gccgcccgcg tgctcggtgc cgccgccttg tccgaggtag      8280
ccaccggcgc ccgcccagtg gcagcatgcg accccgcgcc cgaggccgcg gccgtaccca      8340
```

```
cgctcgaacg cgcgcccgct cccacggcgg taccgctcgg cgcggcggcc gccgcccgtg      8400
cgcccgggac accggacgcc gcagccggcg tcaccgacgc ggcggattcg tccgcatggg      8460 caggcccga ctgcgtcccc ccgcccgcat gctggcccgg cacaccaggt tgctccgcca       8520
acgccgcggg tttgacgtgc ggcgccggct cgcccctgg ggtgcccggt gttgctggac       8580
cagacggacc gggagtggcc ggtgtaaccg gctggggccc aggcgatggc gccggtgccg      8640
gagccggctg cgggtgtgga gcgggagctg gggtaacggg cgtggccggg gttgccggtg      8700
tggccggggc gaccgggggg gtgaccggcg tgatcggggt tggctcgcct ggtgtgcccg      8760
gtttgaccgg ggtcaccggg gtgaccggct tgcccggggt caccggcgtg acgggagtgc     8820
cgggcgttgg tgtgatcgga gttaccggcg ctcccgggat gggtgtgatt ggggttcccg    8880
gggtgatcgg ggttcccggg gtgatcgggg ttcccggtgt gcccggtgtg cccggggatg     8940
gcacgaccag ggtaggcacg tctgggggtg gcggcgactt ctgctgaagc aaatcctcga     9000
gtgcgttctt cggaggtttc caattcttgg attccagcac ccgctcagcg gtctcggcga    9060
ccagactgac attggcccca tgcgtcgccg tgaccaatga attgatggcg gtatggcgct    9120
catcagcatc caggctaggg tcattctcca ggatatcgat ctcccgttga gcgccatcca    9180
cattattgcc gatatcggat ttagcttgct caatcaaccc ggcaatatgc ctgtgccagg    9240
taatcaccgt ggcgagataa tcctgcagcg tcatcaattg attgatgttt gcacccaggg   9300
cgccgttggc agcattggcg gcgccgccgg accataggcc gccttcgaag acgtggcctt    9360
tctgctggcg gcaggtgtcc aatacatcgg tgaccctttg caaaacctgg ctatattcct    9420
gggcccggtc atagaaagtg tcttcatcgg cttc                                9454
```

<210> SEQ ID NO 2
<211> LENGTH: 1298
<212> TYPE: DNA
<213> ORGANISM: Mycobacterium tuberculosis

<400> SEQUENCE: 2

```
ggtctagcag ctcgcccgcg ttttcgggca caaatgccgg atcgtggccc atgtcgatcg      60
gtttgttgta agcgtcgaca aacacgatcc gcggctggta tgtgcgggcc cgggcgtcgt    120
ccatcgtcgc gtacgcaatc agaatcacca gatcccccgg atgcaccaag tgcgcggcgg    180
caccgttgat gccaatcaca ccactgccgc gttcgccggt gatcgcgtag gtgaccagtc     240
gagcaccgtt gtcgatatcg acgatggtta cctgttcgcc ttccagcagg tcggcggcgt    300
ccatcaagtc ggcatcgatg gtcaccgagc cgacgtagtg caggtcggcg caggtcaccg    360
tggcgcggtg gatcttcgac ttcagcatcg tccgtaacat cagtttctcc aatgtgattc    420
gaggattgcc cggtatccgt ccgggcggtc ggtgccggcg aaagttccga tttcaatcgc    480
aatgttgtcc agcagcctgg tggtgccaag ccgggcagca accagcagcc gaccggaacc     540
gttgagcggc atcgggccaa gcccgatatc gcgcagctcc aggtagtcga ccgccacgcc    600
gggtgcagcg tcgagcaccg cacgggcggc atcagcgcg gcctgcgcgc cagccgttgc     660
cgcatgcgct gcggccgtta gcgccgccga gagcgcgacg gccgccgcac gctgggccgg    720
gtccaggtag cggttgcgcg acgacatcgc cagcccgtcg gcttcgcgca ggtcggcac    780 gccgaccacc gcgacatcga ggttgaagtc gcgaccagc tgccggatca gcaccagctg    840
ctggtagtcc ttctcaccga agaacacccg atccggggcg acgatctgca gcagctttag    900
cacgaccgtc agcacgccgg cgaaatgggt tggccgcggg ccgccctcga gttcggcggc    960
caacggaccg ggttgcacgg tggtgcgcag gccgtcggga tacatcgccg cggtagttgg   1020
```
cgtgaaagcg atttccacgc cttcggcccg cagttgcgcc aggtcgtcgt ccggggtgcg 1080
gggataggcg tcgagatctt ccccggcacc gaattgcatc gggttgacga agatcgacac 1140
gacgacgacc gatccgggca cccgcttggc cgcacgcacc aacgcgaggt ggccttcgtg 1200
cagcgcaccc atagtaggca ccaacatcac tcgccggccg gtgagtcgca gtgcgcgact 1260
gacatcggcg acatcccccg gtgccgagta cacattga 1298

<210> SEQ ID NO 3
<211> LENGTH: 771
<212> TYPE: DNA
<213> ORGANISM: Mycobacterium tuberculosis

<400> SEQUENCE: 3
aacgggcgat gagccgggac gcgtcgatgt accgcgccgc cgccgggctg caccggctgt 60
gcgacagcct atccggagca caggttcgcg acgtggcttg tcgccgcgat ttcgaggacg 120
tggcgctcac gctggtcgcg cagagcgtga ccgccgccgc cttggcccgc accgaaagcc 180
gtggctgcca tcatcgcgcg gagtacccgt gcaccgtgcc ggagcaggca cgcagcatcg 240
tggtccgggg agccgacgac gcaaatgcgg tgtgtgtcca ggcgctagtg gcggtgtgct 300
gatggggtta tccgactggg agctggctgc ggctcgagca gcaatcgcgc gtgggctcga 360
cgaggacctc cggtacggcc cggatgtcac cacattggcg acggtgcctg ccagtgcgac 420
gaccaccgca tcgctggtga cccgggaggc cggtgtggtt gccggattgg atgtcgcgct 480
gctgacgctg aacgaagtcc tgggcaccaa cggttatcgg gtgctcgacc gcgtcgagga 540
cggcgcccgg gtgccgccgg gagaggcact tatgacgctg gaagcccaaa cgcgcggatt 600
gttgaccgcc gagcgcacca tgttgaacct ggtcggtcac ctgtcgggaa tcgccaccgc 660
gacggccgcg tgggtcgatg ctgtgcgcgg gaccaaagcg aaaatccgcg atacccgtaa 720
gacgctgccc ggcctgcgcg cgctgcaaaa atacgcggtg cgtaccggtg g 771

<210> SEQ ID NO 4
<211> LENGTH: 1255
<212> TYPE: DNA
<213> ORGANISM: Mycobacterium tuberculosis

<400> SEQUENCE: 4
gtgaacgagc tgctgcactt agcgccgaat gtgtggccgc gcaatactac tcgcgatgaa 60
gtcggtgtgg tctgcatcgc aggaattcca ctgacgcagc tcgcccagga gtacgggacc 120
ccgctgttcg tcatcgacga ggacgacttt cgctcgcgct gccgagaaac cgccgcggcc 180
tttggaagtg gggcgaacgt gcactatgcc gccaaggcgt tcctgtgcag cgaagtagcc 240
cggtggatca gcgaagaagg gctctgtctg gacgtttgca ccggtgggga gttggcggtc 300
gcgctgcacg ctagctttcc gcccgagcga attaccttgc acggcaacaa caaatcggtc 360
tcagagttga ccgctgcggt caaagccgga gtcggccata ttgtcgtcga ttcgatgacc 420
gagatcgagc gcctcgacgc catcgcgggc gaggccggaa tcgtccagga tgtcctggtg 480
cgtctcaccg tcggtgtcga ggcgcacacc cacgagttca tctccaccgc gcacgagacg 540
cgtcagccac atcggttcgc agatcttcga cgtggacggc ttcgaactcg ccgcgcaccg 600
tgtcatcggc ctgctacgcg acgtcgtcgg cgagttcggt cccgaaaaga cggcacagat 660
cgcgaccgtc gatctcggtg gcggcttggg catctcgtat ttgccgtccg acgacccacc 720
gccgatagcc gagctcgcgg ccaagctggg taccatcgtg agcgacgagt caacggccgt 780
ggggctgccg acgcccaagc tcgttgtgga gcccggacgc gccatcgccg gaccgggcac 840

-continued

```
catcacgttg tatgaggtcg gcaccgttaa ggacgtcgat gtcagcgcca cagcgcatcg      900
acgttacgtc agtgtcgacg gcggcatgag cgacaacatc cgcaccgcgc tctacggcgc      960
gcagtatgac gtccggctgg tgtctcgagt cagcgacgcc ccgccggtac cggcccgtct     1020
ggtcggaaag cactgcgaaa gtggcgatat catcgtgcgg gacacctggg tgcccgacga     1080
tattcggccc ggcgatctgg ttgcggttgc cgccaccggc gcttactgct attcgctgtc     1140
gagtcgttac aacatggtcg gccgtcccgc tgtggtagcg gtgcacgcgg gcaacgctcg     1200
cctggtcctg cgtcgggaga cggtcgacga tttgctgagt ttggaagtga ggtga         1255
```

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
gggggcgcac ctcaaacc                                                    18

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
atgtgccaat cgtcgaccag aa                                               22

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
cacccagccg cccggat                                                     17

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttcctgatgc cgccgtctga                                                  20

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
gtgcagcgcc atctctca                                                    18

<210> SEQ ID NO 10
<211> LENGTH: 18
<212> TYPE: DNA
<213> ORGANISM: Artificial

```
<220> FEATURE:
<223> OTHER INFORMATION: primer

<400> SEQUENCE: 10
gttcaccggg atggaacg                                              18

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
cccggctcgg tgtgggat                                              18

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
gcgcggtatg cccggtag                                              18
```